(12) United States Patent
Curtiss, III et al.

(10) Patent No.: US 9,481,888 B2
(45) Date of Patent: Nov. 1, 2016

(54) RECOMBINANT BACTERIUM AND METHODS OF ANTIGEN AND NUCLEIC ACID DELIVERY

(75) Inventors: Roy Curtiss, III, Paradise Valley, AZ (US); Wei Kong, Phoenix, AZ (US)

(73) Assignee: The Arizona Board of Regents for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/302,575

(22) Filed: Nov. 22, 2011

(65) Prior Publication Data

US 2012/0087946 A1     Apr. 12, 2012

Related U.S. Application Data

(63) Continuation-in-part of application No. PCT/US2010/035630, filed on May 20, 2010.

(60) Provisional application No. 61/180,620, filed on May 22, 2009, provisional application No. 61/222,306, filed on Jul. 1, 2009.

(51) Int. Cl.
| | | |
|---|---|---|
| C12N 15/74 | (2006.01) | |
| C12N 1/36 | (2006.01) | |
| A61K 39/02 | (2006.01) | |
| C12N 9/10 | (2006.01) | |
| C07K 14/255 | (2006.01) | |
| A61K 39/112 | (2006.01) | |
| A61K 39/09 | (2006.01) | |

(52) U.S. Cl.
CPC ........... *C12N 15/74* (2013.01); *A61K 39/0275* (2013.01); *A61K 39/092* (2013.01); *C12N 1/36* (2013.01); *C12N 9/1048* (2013.01)

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |
| 5,294,441 A | 3/1994 | Curtiss, III |
| 5,387,744 A | 2/1995 | Curtiss, III |
| 5,389,368 A | 2/1995 | Gurtiss, III |
| 5,424,065 A | 6/1995 | Curtiss, III |
| 5,468,485 A | 11/1995 | Curtiss, III |
| 5,536,658 A | 7/1996 | Shotts, Jr. et al. |
| 5,654,184 A | 8/1997 | Curtiss, III |
| 5,656,488 A | 8/1997 | Curtiss, III |
| 5,672,345 A | 9/1997 | Curtiss, III |
| 5,679,880 A | 10/1997 | Curtiss, III |
| 5,686,079 A | 11/1997 | Curtiss, III |
| 5,817,317 A | 10/1998 | Titball |
| 5,827,705 A * | 10/1998 | Dean .............................. 435/458 |
| 5,840,483 A | 11/1998 | Curtiss, III |
| 5,855,879 A | 1/1999 | Curtiss, III |
| 5,855,880 A | 1/1999 | Curtiss, III |
| 5,961,983 A | 10/1999 | Brey et al. |
| 6,024,961 A | 2/2000 | Curtiss, III |
| 6,180,614 B1 | 1/2001 | Davis |
| 6,248,329 B1 | 6/2001 | Chandrashekar et al. |
| 6,350,454 B1 | 2/2002 | Thune |
| 6,383,496 B1 | 5/2002 | Curtiss, III |
| 6,399,074 B1 | 6/2002 | Roland |
| 6,403,094 B1 | 6/2002 | Titball |
| 6,610,529 B1 | 8/2003 | Curtiss, III |
| 6,780,405 B1 | 8/2004 | Curtiss, III |
| 6,872,547 B1 | 3/2005 | Curtiss, III |
| 6,969,513 B2 | 11/2005 | Galen |
| 7,083,794 B2 | 8/2006 | Curtiss, III |
| 7,195,757 B2 | 3/2007 | Curtiss, III |
| 7,205,125 B2 | 4/2007 | Castillo |
| 7,341,860 B2 | 3/2008 | Curtiss, III |
| 7,871,604 B1 | 1/2011 | Curtiss, III |
| 7,968,101 B2 | 6/2011 | Kawaoka |
| 8,133,493 B2 | 3/2012 | Curtiss, III |
| 8,445,254 B2 | 5/2013 | Curtiss, III et al. |
| 8,465,755 B2 | 6/2013 | Curtiss, III et al. |
| 2003/0031683 A1 | 2/2003 | Curtiss, III |
| 2003/0175772 A1 | 9/2003 | Wang |
| 2004/0077556 A1 | 4/2004 | Chinery |
| 2004/0101531 A1 | 5/2004 | Curtiss, III |
| 2004/0120962 A1 | 6/2004 | Curtiss, III |
| 2004/0137003 A1 | 7/2004 | Curtiss, III |
| 2004/0203039 A1 | 10/2004 | Hensel |
| 2005/0036987 A1 | 2/2005 | Pawelek |
| 2005/0106175 A1 | 5/2005 | Montanes |
| 2005/0106176 A1 | 5/2005 | Curtiss, III |

(Continued)

FOREIGN PATENT DOCUMENTS

| | | |
|---|---|---|
| EP | 0315682 B1 | 12/1993 |
| EP | 0381706 B1 | 4/1995 |
| EP | 0465560 B1 | 6/1996 |
| EP | 0500699 B1 | 6/1998 |
| EP | 0558631 B1 | 3/1999 |
| EP | 0433372 B1 | 6/2002 |
| EP | 1030690 B1 | 7/2002 |
| EP | 0556333 B1 | 3/2003 |
| EP | 1326960 B1 | 12/2004 |
| EP | 0832255 B1 | 12/2005 |

(Continued)

OTHER PUBLICATIONS

Rytkonen et al. PNAS vol. 104, No. 9, p. 3502-3507 Feb. 27, 2007.*

(Continued)

*Primary Examiner* — Oluwatosin Ogunbiyi
(74) *Attorney, Agent, or Firm* — McCarter & English, LLP; Elizabeth A. Hanley, Esq.; Marcie B. Clarke

(57) ABSTRACT

The present invention provides a recombinant bacterium and methods of using the recombinant bacterium to induce an immune response.

21 Claims, 30 Drawing Sheets

(56) References Cited

U.S. PATENT DOCUMENTS

| | | |
|---|---|---|
| 2005/0118193 A1* | 6/2005 | Andino-Pavlovsky et al. ............... 424/200.1 |
| 2006/0140975 A1* | 6/2006 | Curtiss et al. ............ 424/200.1 |
| 2006/0171917 A1 | 8/2006 | Campbell |
| 2006/0206961 A1 | 9/2006 | Cirpus |
| 2006/0233829 A1 | 10/2006 | Curtiss, II |
| 2006/0234346 A1 | 10/2006 | Retallack |
| 2006/0275255 A1 | 12/2006 | Gudkov |
| 2007/0025981 A1 | 2/2007 | Szalay |
| 2008/0096809 A1 | 4/2008 | Shai |
| 2008/0248066 A1 | 10/2008 | Dubensky, Jr. |
| 2009/0175829 A1 | 7/2009 | Forbes |
| 2010/0124558 A1 | 5/2010 | Curtiss, III |
| 2010/0154293 A1 | 6/2010 | Hom et al. |
| 2010/0255022 A1 | 10/2010 | Prescott et al. |
| 2010/0285592 A1 | 11/2010 | Curtiss, III |
| 2010/0317084 A1 | 12/2010 | Curtiss, II |
| 2011/0033501 A1 | 2/2011 | Curtiss, III et al. |
| 2011/0256181 A1 | 10/2011 | Curtiss, III |
| 2011/0287052 A1 | 11/2011 | Curtiss, III et al. |
| 2013/0004537 A1 | 1/2013 | Curtiss, III et al. |
| 2013/0171190 A1 | 7/2013 | Curtiss, III et al. |

FOREIGN PATENT DOCUMENTS

| | | |
|---|---|---|
| EP | 1537214 B1 | 3/2006 |
| EP | 1292687 B1 | 8/2006 |
| WO | 88/09669 A1 | 12/1988 |
| WO | 89/03427 A1 | 4/1989 |
| WO | 90/02484 A1 | 3/1990 |
| WO | 90/11687 A1 | 10/1990 |
| WO | 90/11688 A1 | 10/1990 |
| WO | 90/12086 A1 | 10/1990 |
| WO | 91/06317 A1 | 5/1991 |
| WO | 92/08486 A1 | 5/1992 |
| WO | 92/09684 A1 | 6/1992 |
| WO | 93/04202 A1 | 3/1993 |
| WO | 94/24291 A2 | 10/1994 |
| WO | 94/24291 A3 | 12/1994 |
| WO | 96/40947 A1 | 12/1996 |
| WO | 99/25387 A1 | 5/1999 |
| WO | 01/83785 A2 | 11/2001 |
| WO | 02/30457 A2 | 4/2002 |
| WO | 01/83785 A3 | 6/2002 |
| WO | 02/059292 A2 | 8/2002 |
| WO | 03/079792 A1 | 10/2002 |
| WO | 02/30457 A3 | 1/2003 |
| WO | 02/030457 A3 | 7/2003 |
| WO | 02/059292 A3 | 7/2003 |
| WO | 03/096812 A1 | 11/2003 |
| WO | 2004/020643 A2 | 3/2004 |
| WO | 2004/020643 A3 | 4/2004 |
| WO | 2005/001069 A1 | 1/2005 |
| WO | 2012087483 A1 | 6/2008 |
| WO | 2008/141226 A2 | 11/2008 |
| WO | 2009/025888 A2 | 2/2009 |
| WO | 2009/046449 A1 | 4/2009 |
| WO | 2009/046451 A1 | 4/2009 |
| WO | 2010/045620 A1 | 4/2010 |
| WO | 2010/078584 A1 | 8/2010 |
| WO | 2010/135563 A1 | 11/2010 |
| WO | 2011/091291 A1 | 7/2011 |
| WO | 2011/150421 A2 | 12/2011 |

OTHER PUBLICATIONS

Mesika et al. Molecular Therapy vol. 3 No. 5, May 2001 p. 653-657.*
Ribeiro et al. The Journal of Gene Medicine. 2004; 6:565-573.*
Wang et al. J. virol. 2006; 80(23):11628-11637.*
Kong et al. American Society for Microbiology General Meeting. Abstract No. T-010, Jun. 2, 2008; 108:668-EOA.*
Whitworth et al. Infect Immun. Oct. 2005: 73 (10):668-6673.*
Folkesson et al. Cellular Microbiology 2005, 7(1), 147-155.*
Baek et al. J. Bacteriol. 2009, 191(4):1278-1292 , Feb. 2009, published Dec. 12, 2008.*
Baek et al. Abstracts of the General Meeting of the American Society for Microbiology 108:99, 2008 (Conference date Jun. 1-5, 2008).*
Olekhnovich et al. J. Mol. Biol (2006) 357,373-386.*
Folkesson et al. Cellular Microbiology (2005) 7(1), 147-155.*
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of Bordetella pertussis using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from Yersinia pestis KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) Salmonella redirects phagosomal maturation. Curr Opin Microbiol, 2004, pp. 78-84, vol. 7.
Cárdenas et al., Oral immunization using live attenuated Salmonella spp. as carriers of foreign antigens. Clin. Microbiol. Rev., 1992, pp. 328-342, vol. 5, No. 3.
Charnetzky et al., RNA synthesis in Yersinia pestis during growth restriction in calcium-deficient medium. J Bacteriol, 1982, pp. 108-195, vol. 149.
Chatfield et al., Use of the nirB promoter to direct the stable expression of heterologous antigens in Salmonella oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC—PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of Yersinia pestis virulence. J Bacteriol, 2005, pp. 8172-8180, vol. 187.

(56) References Cited

OTHER PUBLICATIONS

Coombes et al., SseL is a Salmonella-Specific Translocated Effector Integrated into the SsrB-Controlled Salmonella Pathogenicity Island 2 Type III Secretion System. Infection and Immunity, 2007, pp. 574-580, vol. 75, No. 2.
Cornelis et al., The virulence plasmid of Yersinia, an antihost genome. Microbiol Mol Biol Rev, 1998, pp. 1315-1352, vol. 62.
Curtiss et al. Nonrecombinant and recombinant avirulent Salmonella vaccines for poultry. Vet Immunol Immunopathol, 1996, pp. 365-372, vol. 54.
Curtiss et al., Live oral avirulent Salmonella vaccines. Vet. Microbiol., 1993, pp. 397-405, vol. 37.
Curtiss et al., Recombinant Salmonella vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of Yersinia pestis KIM. J Bacteriol, 2002, pp. 4601-4611, vol. 184.
Doggett et al., Delivery of antigens by recombinant avirulent Salmonella strains. Adv. Exp. Med. Biol., 1992, pp. 165-173, vol. 327.
Doublet et al., The murI gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How Salmonella survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the Yersinia pestis Yfu ABC inorganic iron transport system. Infect Immun, 2001, pp. 2829-2837, vol. 69.
Gor et al., TH1-TH2: a Procrustean paradigm. Nat Immunol, 2003, p. 503-5, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Hess et al., Secretion of different listeriolysin cognates by recombinant attenuated *Salmonella typhimurium*: superior efficacy of haemolytic over non-haemolytic constructs after oral vaccination. Microbes Infect., 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., the inducible lac operator-repressor system is functional in mammalian cells. Cell, 1987, pp. 555-566, vol. 48, No. 4.
Hu et al., The inducible lac operator-repressor system is functional for control of expression of injected DNA in Xenopus oocytes. Gene, 1988, pp. 301-313, vol. 62, No. 2.
Huang et al., Genome-wide screen of Salmonella nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a Porphyromonas gingivalis hemagglutinin on the surface of a Salmonella vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of Yersinia pestis by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., Salmonella-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on Salmonella carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.

(56) References Cited

OTHER PUBLICATIONS

Marshall et al., Use of the stationary phase inducible promoters, spy and dps, to drive heterologous antigen expression in Salmonella vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in Yersinia pestis. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a Salmonella vaccine strain. BioTechnology, 1988, pp. 693-697, vol. 6.
Nedialkov et al., Resistance to lipopolysaccharide mediated by the Yersinia pestis V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of Yersinia pestis is posttranscriptional. J Bacteriol, 2004, pp. 1638-1647, vol. 186.
Petersen et al., Essential role for cyclic Amp and its receptor protein in Yersinia enterocolitica virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate Salmonella vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of Salmonella-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.

Schödel et al., Hybrid hepatitis B virus core antigen as a vaccine carrier moiety. II. Expression in avirulent Salmonella spp. For mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
PCT/US2011/061896—International Search Report and Written Opinion of the International Searching Authority, Apr. 5, 2012.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Byl et al, Sequence of the Genomore of Salmonella Bacteriophage P22. Journal of Bacteriology, 2000, pp. 6472-6484, vol. 182, 22.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in Salmonella spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infectimmun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.
U.S. Appl. No. 12/615,872, Office Action dated Mar. 14, 2012.
Collins et al, Mutation at rfc or pmi Attenuate *Salmonella typhimurium* Virulence for Mice. Infect and Immun, 1991, pp. 1079-1085, vol. 59, No. 3.

(56) References Cited

OTHER PUBLICATIONS

Curtiss et al., Stabilization of Recombinant Avirulent Vaccine Strains in vivo. Res. Microbiol., 1990, pp. 797-805, vol. 141.
Curtiss et al, Avirulent *Salmonell typhimurim* cyc crp oral vaccine strains expressing a streptococcal colonization and virulence antigen. Vaccine, 1988, pp. 155-160, vol. 6.
Darzins et al., Nucleotide sequence analysis of the phosphomannose isomerase gene (pmi) of Pseudomonas aeruginose and comparison with the corresponding *Escherichia coli* gene manA. Gene, 1986, pp. 293-302, vol. 42.
Doggett et al., Immune Responses to *Streptococcus sobrinus* Surface Protein Antigen a Expressed by Recombinant *Salmonella typhimurium*. Infect and Immun, 1993, pp. 1859-1866, vol. 61, No. 5.
Egan et al., A Regulatory Cascade in the Induction of rhaBAD. J. Mol. Biol., 1993, pp. 87-98, vol. 234.
Guzman et al., Tight regulations, Modulations, and High-Level Expression by Vectors Containing the Arabinose Pbad Promotor. Journal of Bacteriology, 1995, pp. 4121-4130, vol. 177, No. 14.
Kennedy et al., Attenuation and Immunogenicity of cya crp Derivatives of *Salmonella choleraeuis* in Pigs. Infect Immun, 1999, pp. 4628-4636, vol. 67, No. 9.
Nickerson et al., Role of Sigma Factor RpoS in Initial Stages of *Salmonella typhimurium* Infection. Infect Immun, 1997, p. 1814-1823, vol. 65, No. 5.
Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.
Schodel, Recombinant Avirulent Salmonellae as Oral Vaccine Carriers. Infection, 1992, pp. 5-12, No. 1.
Siegele et al., Gene Expression from plasmids containing the araBAD promoter at subsaturating inducer concentrations represents mixed populations. PNAS, 1997, pp. 8168-8172, vol. 94.
Song et al., Organization and Regulation of the d-Xylose Operons in *Escherichia coli* K-12: XylR Acts as a Transcriptional Activator. Journal of Bacteriology, 1997, pp. 7025-7032, vol. 197, No. 22.
Srinivasan et al., Oral Immunization with Attenuated Salmonella Expressing Human Sperm Antigen Induces Antibodies in Serum and the Reproductive Tract. Biology of Reproduction, 1995, p. 462-71 vol. 53.
PCT/US2008/063293 (WO 2009/025888)—International Search Report and Written Opinion of the International Searching Authority, Feb. 12, 2009.
CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
U.S. Appl. No. 13/006,072, Office Action dated Apr. 19, 2012.
Sun et al. Highly efficient method for introducing successive multiple scarless gene deletions and markerless gene insertions into the Yersinia pestis chromosome. Appl Environ Microbiol, 2008, pp. 4241-4245, vol. 74.
Curtiss et al., New technologies in using recombinant attenuated Salmonella vaccine vectors. Crit. Rev. Immunol., 2010, pp. 255-270, vol. 30.
Curtiss et al., Salmonella strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Waltman et al., Biochemical Characteristics of Edwardsiella ictaluri. Applied and Enviornmental Microbiology, 1986, pp. 101-104, vol. 51, No. 1.
Curtiss, Bacterial infectious disease control by vaccine development. J. Clin. Investig., 2002, pp. 1061-1066, vol. 110.

Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Takaya et al., The ATP-Dependent Lon Protease of *Salmonella enterica* Serovar Typhimurium Regulates Invasion and Expression of Genes Carried on Salmonella Pathogenicity Island 1. Journal of Bacteriology, 2002, pp. 224-232, vol. 184, No. 1.
Dean, 1997. Import of plasmid DNA into the nucleus is sequence specific. Exp. Cell Res., 1997, pp. 293-302, vol. 230.
Reed et al., The W-Beijing Lineage of Mycobacterium tuberculosis Overproduces Triglycerides and Has the DosR Dormancy Regulon Constitutively Upregulated. Journal of Bacteriology, 2007, pp. 2583-2589, vol. 189, No. 7.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned Porphyromonas gingivalis hemagglutinin. Infect Immun, 1994, pp. 1652-1657, vol. 62, No. 5.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of Shigella sonnei form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella typhimurium* to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella typhi* CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.
Gentschev et al., Delivery of the p67 sporozoite antigen of Theileria parva by using recombinant Salmonella dublin: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.
Greenwood, The epidemiology of pneumococcal infection in children in the developing world. Philos. Trans. R. Soc. Lond. B. Biol. Sci., 1999, pp. 777-785, vol. 354.
Gulig et al., Plasmid-associated virulence of *Salmonella typhimurium*. Infect Immun, 1987, pp. 2891-2901, vol. 55.
Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.

(56) References Cited

OTHER PUBLICATIONS

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant Salmonella vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among Salmonella lipopolysaccharide chemotypes in silver-stained polyacrylamide gels. J Bacteriol, 1983, pp. 269-277, vol. 154, No. 1.

Hoffmann et al., "Ambisense" approach for the generation of influenza A virus: vRNA and mRNA synthesis from one template. Virology, 2000, pp. 310-317, vol. 267.

Hohmann et al., Macrophage-inducible expression of a model antigen in Salmonella typhimurium enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect. Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.

Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.

Kang et al., Immune responses to recombinant pneumococcal PspA antigen delivered by live attenuated *Salmonella enterica* serovar typhimurium vaccine. Infect. Immun., 2002, pp. 1739-1749, vol. 70.

Kang et al., Transduction-mediated transfer of unmarked deletion and point mutations through use of counterselectable suicide vectors. J Bacteriol, 2002, pp. 307-312, vol. 184.

Katzman et al., Invertebrate connective tissue. Isolation of D-arabinose from sponge acidic polysaccharide. Biochem J, 1970, pp. 17-19, vol. 119, No. 1.

Hurme et al, A Proteinaceous Gene Regulator Thermameter in Salmonella. Cell, 1997, pp. 55-64, vol. 90.

Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.

Klumpp et al., Roles of the influenza virus polymerase and nucleoprotein in forming a functional RNP structure. EMBO J., 1997, pp. 1248-1257, vol. 16.

Kong et al, Regulated programmed lysis of recombinant Salmonella in host tissues to release protective antigens and confer biological containment. PNAS, 2008, pp. 9361-9366, vol. 105, No. 27.

Konjufca et al., A Recombinant Attenuated *Salmonella enterica* Serovar Typhimurium Vaccine Encoding Eimeria acervulina Antigen Offers Protection against E. acervulina Challenge. Infect. Immun., 2006, pp. 6785-6796, vol. 74.

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.

Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+ T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol., 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al., Complete genome sequence of *Salmonella enterica* serovar Typhimurium LT2. Nature, 2001, pp. 852-856, vol. 413, No. 6858.

McDaniel et al., Monoclonal antibodies against protease sensitive pneumococcal antigens can protect mice from fatal infection with *Streptococcus pneumoniae*. J. Exp. Med., 1984, pp. 368-397, vol. 160.

McDaniel et al., Use of insertional inactivation to facilitate studies of biological properties of pneumococcal surface protein A (PspA). J. Exp. Med., 1987, pp. 381-394, vol. 165.

Miller et al., A novel suicide vector and its use in construction of insertion mutations: osmoregulation of outer membrane proteins and virulence determinants in Vibrio cholerae requires toxR. J Bacteriol, 1988, pp. 2575-2583, vol. 170.

Miller et al., Bacteriophage T4 genome. Microbiol Mol Biol Rev, 2003, pp. 86-156, vol. 67, No. 1.

Molinari et al., The annual impact of seasonal influenza in the US: measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.

Nayak et al., A live recombinant avirulent oral Salmonella vaccine expressing pneumococcal surface protein A induces protective responses against *Streptococcus pneumoniae*. Infect Immun., 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs. Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

(56) References Cited

OTHER PUBLICATIONS

Noda et al., Architecture of ribonucleoprotein complexes in influenza A virus particles. Nature, 2006, pp. 490-492, vol. 439.
Oehler et al., The three operators of the lac operon cooperate in repression. EMBO J, 1990, pp. 973-979, vol. 9, No. 4.
Ogunniyi et al., Contributions of Pneumolysin, Pneumococcal Surface Protein A (PspA), and PspC to Pathogenicity of *Streptococcus pneumoniae* D39 in a Mouse Model. Infect. Immun., 2007, pp. 1843-1851, vol. 75.
Osterholm, Preparing for the next pandemic. N. Engl. J. Med., 2005, pp. 1839-1842, vol. 352.
Ozaki et al., Generation of high-yielding influenza A viruses in African green monkey kidney (Vero) cells by reverse genetics. J. Virol., 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.
Pashine et al., Th1 dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates Salmonella virulence nucleic acid sequence expression. Mol Microbiol, 2004, pp. 1827-1844, vol. 52, No. 6.
Prouty et al., *Salmonella enterica* serovar Typhimurium invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of Salmonella strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-560, vol. 183.
Hori et al, Constructionof selt-disruptive Bacillus megaterium in response to substrate exhaustion for polyhydroxybutryrate production. Appl Microbiol Biotechnol, 2002, pp. 211-216, vol. 59.
Houng et al., Expression of Vi antigen in *Escherichia coli* K-12: characterization of ViaB from Citrobacter freundii and identity of ViaA with RcsB. J.Bacterio, 1992, pp. 5910-5915, vol. 174, No. 18.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Simonsen et al., The impact of influenza epidemics on hospitalizations. J. Infect. Dis., 2000, pp. 831-837, vol. 181.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar Typhimurium. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydel Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.

(56) References Cited

OTHER PUBLICATIONS

Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for Salmonella virulence in mice. J. Clin. Invest., 1995, pp. 1047-1053, vol. 95.
Bumann, Regulated antigen expression in live recombinant *Salmonella enterica* serovar Typhimurium strongly affects colonization capabilities and specific CD4(+)-T-cell responses. Infect Immun, 2001. pp. 7493-7500, vol. 69, No. 12.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of Yersinia pestis is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in Yersinia pestis include structural genes for outer membrane proteins. Infect Immun, 1986, pp. 445-454, vol. 51.
Sun et al., The role of relA and spoT in Yersinia pestis KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of Salmonella. J Biol Chem, 2006, pp. 30112-30121, vol. 281.
Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in Salmonella. Proc Natl Acad Sci U S A, 2001, pp. 15264-15269, vol. 98.
Viboud et al., Yersinia outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in Yersinia pestis. Infect Immun, 1982, pp. 953-959, vol. 38.

Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in Rhodococcus opacus PD630 and Mycobacterium smegmatis mc2155, and provides an anchor to target other proteins. Microbiology, 2006, pp. 3271-3280, vol. 152.
Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.
Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.
Morita et al., Antibacterial Activity of Bacillus amyloliquefaciencs Phage Endolysin without Holin Conjugation. Journal of Biosciences and Bioengineering, 2001, pp. 469-473, vol. 91, No. 5.
Navasa et al, Temperature has reciprocal effects on colanic acid and polysialic acid biosynthesis in *E. coli* K92. Appl Microbiol Biotechnol, 2009, pp. 721-729, vol. 82.
Stevens, Immunization with the C-Domain of alpha-Toxin Prevents Lethal Infection, Localizes Tissue Injury, and Promotes Host Responses to Challenge with Clostridium perfringens. JID, 2004, pp. 767-773, vol. 190.
Verjan et al, Genetic Loci of Major Antigenic Protein Genes of Edwardsiella tarda. Applied and Environmental Microbiology, 2005, pp. 5654-5658, vol. 71, No. 9.
U.S. Appl. No. 12/599,655 Office Action dated Jul. 2, 2012.
U.S. Appl. No. 12/681,721, Office Action dated May 24, 2012.
U.S. Appl. No. 12/759,842, Office Action dated Jun. 7, 2012.
Ellis, New Technologies for Making Vaccines. Vaccines, 1988, pp. 568-574, Chapter 29, WB Saunders Company, United States.
Greenspan et al, Defining eptiopes: It's not as easy as it seems. Nature Biotechnology, 1999, pp. 936-937, vol. 17.
Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.
U.S. Appl. No. 12/615,872 Office Action dated Oct. 23, 2012.
PCT/US2008/063303 (WO 2008/141226)—International Search Report and Written Opinion of the International Searching Authority, Nov. 26, 2008.
U.S. Appl. No. 12/759,842, Office Action dated Oct. 4, 2011.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.

(56) References Cited

OTHER PUBLICATIONS

PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
U.S. Appl. No. 12/599,655, Office Action dated Mar. 12, 2013.
U.S. Appl. No. 12/681,711, Office Action dated Nov. 28, 2012.
U.S. Appl. No. 12/789,869, Office Action dated Jun. 3, 2014.
U.S. Appl. No. 13/088,141, Office Action dated Apr. 24, 2014.
U.S. Appl. No. 13/574,718, Office Action dated Sep. 6, 2013.
U.S. Appl. No. 13/574,718, Office Action dated Apr. 28, 2014.
U.S. Appl. No. 13/700,591, Office Action dated Apr. 2, 2014.
U.S. Appl. No. 13/898,241, Office Action dated Apr. 17, 2014.
Bittner et al., RpoS and RpoN are involved in the growth-dependent regulation of rtaH transcription and O antigen expression in *Salmonella enterica* serovar Typhi, Microbial Pathogenisis. vol. 36, 2004 (p. 19).
Liu et al., Nickel-inducible lysis system in Synechocystis sp. PCC 6803. PNAS, vol. 106, 2009, pp. 21550-21554.
Liu et al., CO2—limitation-inducible Green Recovery of fatty acids from cyanobacterial biomass. PNAS, vol. 108, 2011 pp. 6905-6908.
Moreno et al., Salmonella as Live Trojan Horse for Vaccine Development and Cancer Gene Therapy. Current Gene Therapy, 2010, 10, pp. 56-76.
Quenee, Lauriane E., et al., Yersinia pestis caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012.
U.S. Appl. No. 13/006,072, Office Action dated Dec. 11, 2012.

\* cited by examiner

A

Δ*relA*::TT *araC* P$_{BAD}$ *lacI*

B

ΔP$_{hilA}$::P$_{trc}$ Δ*lacO* *hilA*

A Δ*asd*::TT *araC* P$_{BAD}$ *c2*

B ΔP$_{murA}$::TT *araC* P$_{BAD}$ ATG *murA*

RECOMBINANT BACTERIUM AND METHODS OF ANTIGEN AND NUCLEIC ACID DELIVERY

CROSS REFERENCE TO RELATED APPLICATIONS

This application claims the priority of PCT Application PCT/US2010/35630, filed May 20, 2010, which claims priority to U.S. provisional application No. 61/180,620, filed May 22, 2009, and U.S. provisional application No. 61/222,306, filed Jul. 1, 2009, each of which is hereby incorporated by reference in its entirety.

GOVERNMENTAL RIGHTS

This invention was made with government support under NIH grant numbers R01 AI065779 and R01 AI056289. The government has certain rights in the invention.

FIELD OF THE INVENTION

The present invention provides a recombinant bacterium and methods of using the recombinant bacterium to deliver an antigen or a nucleic acid encoding an antigen to induce an immune response.

BACKGROUND OF THE INVENTION

Recombinant microorganisms have widespread utility and importance. One use of these microorganisms is as live vaccines to produce an immune response. When the recombinant microorganism is used as a vertebrate live vaccine, certain considerations must be taken into account. To provide a benefit beyond that of a nonliving vaccine, the live vaccine microorganism must attach to, invade, and survive in lymphoid tissues of the vertebrate and expose these immune effector sites to antigen for an extended period of time. Through this continual stimulation, the vertebrate's immune system becomes more highly reactive to the antigen than with a nonliving vaccine. Therefore, preferred live vaccines are attenuated pathogens of the vertebrate, particularly pathogens that colonize the gut-associated lymphoid tissue (GALT), nasopharynx-associated lymphoid tissue (NALT) or bronchial-associated lymphoid tissue (BALT). An additional advantage of these attenuated pathogens over nonliving vaccines is that these pathogens have elaborate mechanisms to gain access to lymphoid tissues, and thus efficient exposure to the vertebrate's immune system can be expected. In contrast, nonliving vaccines will only provide an immune stimulus if the vaccine is passively exposed to the immune system, or if host mechanisms bring the vaccine to the immune system.

Appropriate attenuation and biocontainment of a live recombinant vaccine is essential. Additionally, a live recombinant vaccine should be capable of delivering antigen to the cytosol of a host cell, if necessary for the appropriate immune response (i.e. cellular vs. humoral). Consequently, there is a need in the art for a recombinant bacterium that may be used as a live vaccine that is attenuated, capable of biocontainment, capable of expressing and/or synthesizing antigen, and capable of delivering antigen or a nucleic acid encoding an antigen to a host cell.

SUMMARY OF THE INVENTION

One aspect of the present invention is a recombinant bacterium. The bacterium is capable of increased invasion into a host cell.

Another aspect of the present invention is a recombinant bacterium capable of reduced bacterium-induced host programmed cell death compared to a wild-type bacterium of the same strain.

Yet another aspect of the present invention is a recombinant bacterium capable of hyper-invasion, regulated escape from a host endosomal compartment, regulated attenuation, regulated lysis, and reduced bacterium-induced host programmed cell death.

Still another aspect of the present invention encompasses a recombinant bacterium capable of regulated lysis within a host cell and capable of delivering a DNA vaccine to the cytosol of a host cell.

A further aspect of the invention encompasses a recombinant bacterium capable of regulated lysis within a host cell. The bacterium also comprises a vector that comprises a promoter for expression of a nucleic acid sequence encoding an antigen in *Salmonella* and a promoter for expression of a nucleic acid sequence encoding an antigen in a host cell.

Still a further aspect of the invention encompasses a recombinant bacterium capable of delivering antigen to a host cell by a secretion system, regulated lysis, and a nucleic acid vaccine vector.

An additional aspect of the invention encompasses a nucleic acid vaccine vector, wherein the vector comprises a DNA nuclear targeting sequence and is resistant to eukaryotic nuclease attack.

Yet another additional aspect of the invention encompasses a vaccine comprising a recombinant bacterium described herein.

Still another aspect of the invention encompasses a vaccine comprising a recombinant bacterium with the ability to maintain multiple plasmids and deliver multiple antigens.

Some aspects encompasses a vaccine comprising a recombinant bacterium capable of: hyper-invasion, regulated escape from a host endosomal compartment, regulated attenuation, regulated lysis, and reduced bacterium-induced host programmed cell death.

Other aspects and iterations of the invention are described more thoroughly below.

deletion of 570 bp (hilA-13 to hilA-583) and inserted 94 bp of artificial $P_{trc\Delta lacO}$ (lacO was replaced by 28 bp random sequence) promoter.

Figure 5:
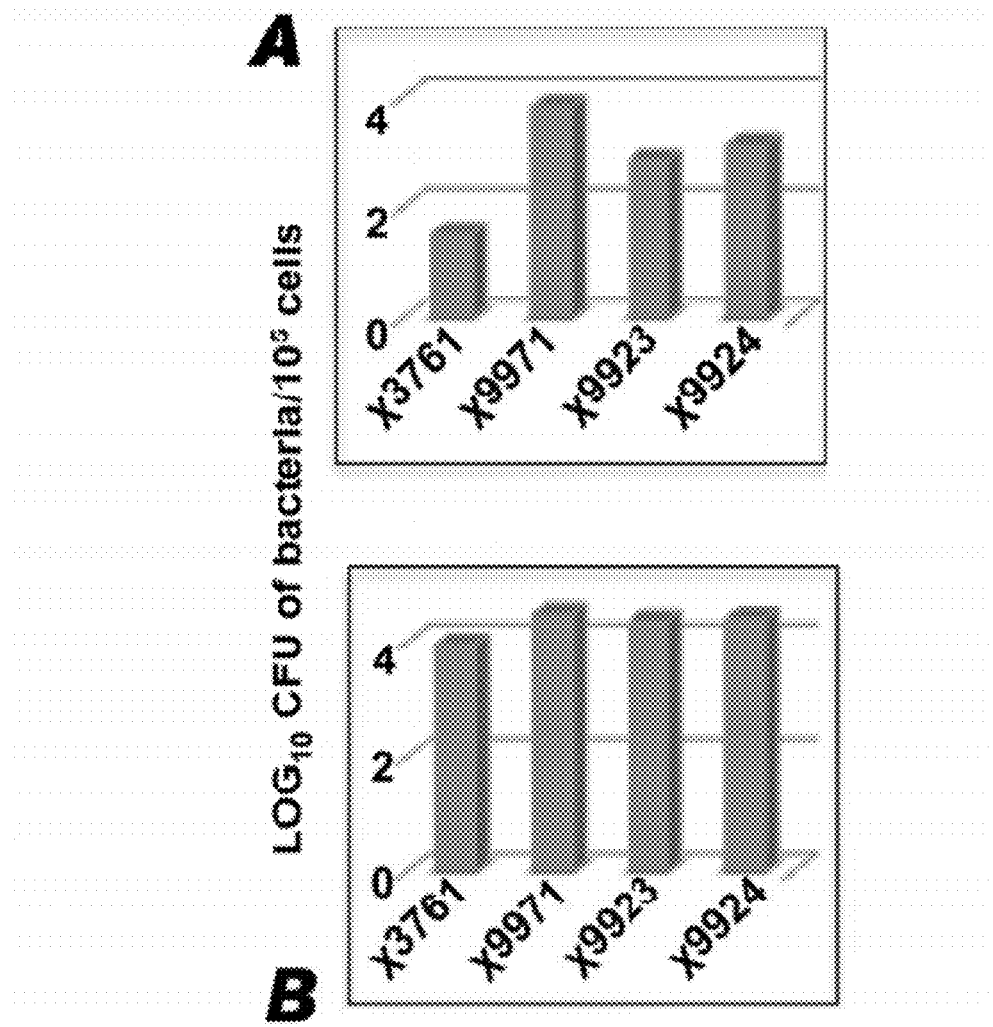

FIG. 5 depicts two graphs showing the (A) invasion (1 hr post infection and (B) replication (18 hr post infenction) of S. Typhimurium strains in the Int-407 cell line.

Figure 6:
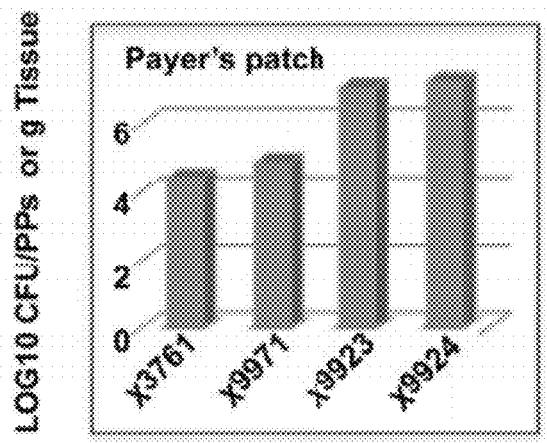
Figure 6:
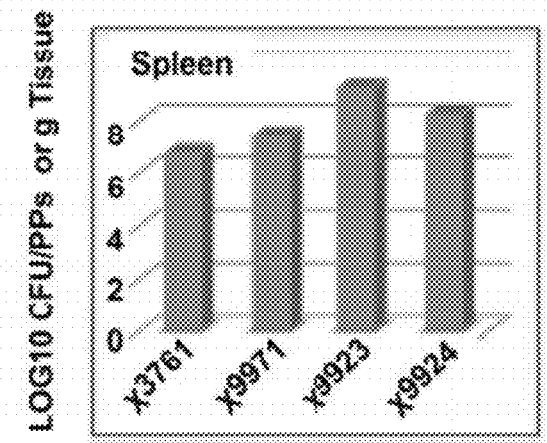
Figure 6:
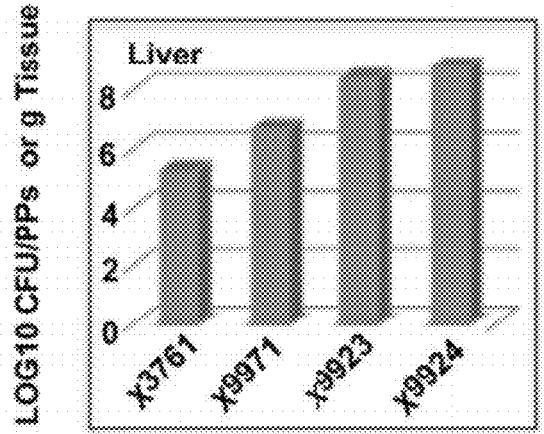

FIG. 6 depicts three graphs showing the colonization of mice with S. Typhimurium strains at Day 6 post-inoculation in the (A) Peyer's patches, (B) spleen, and (C) liver.

Figure 7:
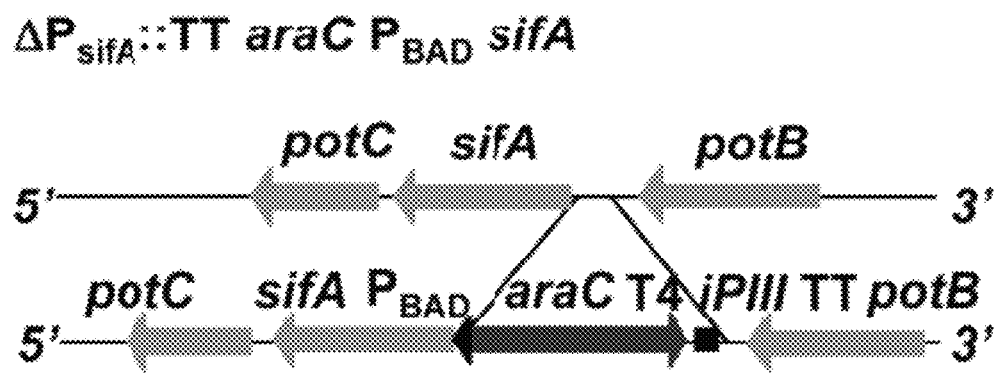

FIG. 7 depicts an illustration of chromosomal deletion-insertion mutations. The sifA promoter region (−1 to −198) was deleted and the 1344 bp $P_{BAD}$ araC TT was inserted.

Figure 8:
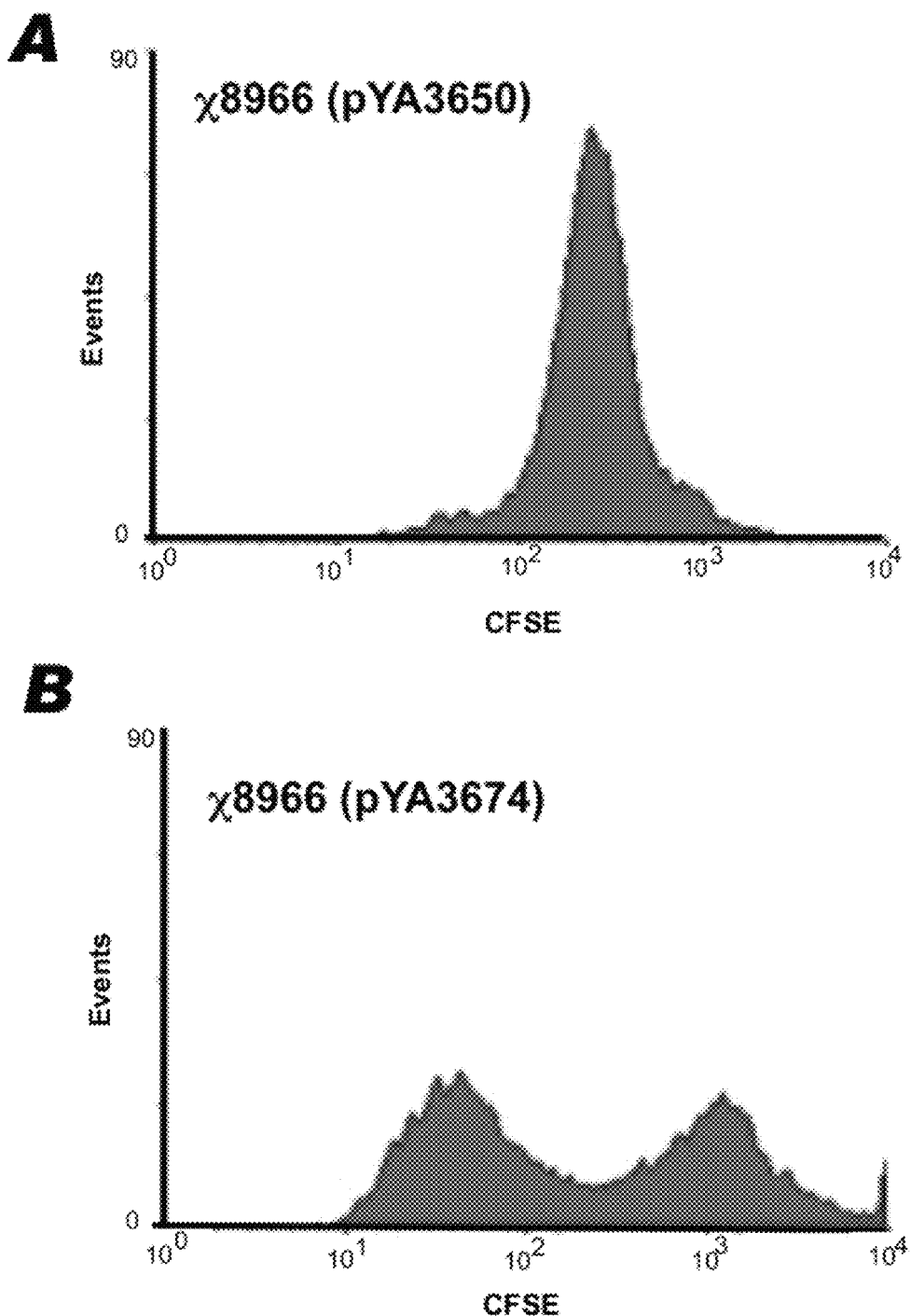

FIG. 8 depicts two graphs showing the proliferation of splenic lymphocytes from immunized chicken to Eimeria antigen EASZ-240. (A) pYA3650, (B) pYA3674.

Figure 9:
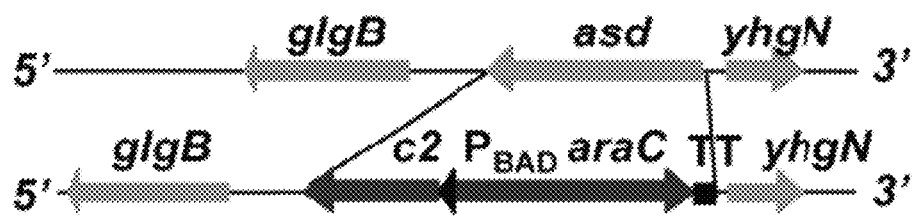
Figure 9:
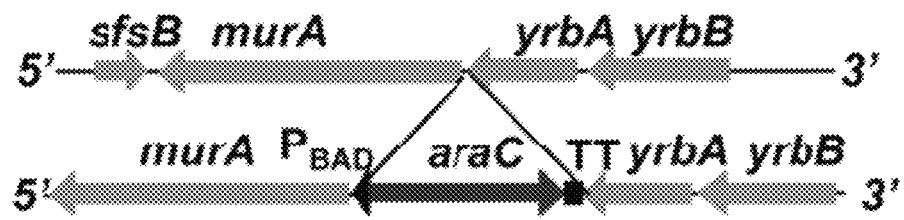

FIG. 9 depicts an illustration of chromosomal deletion-insertion mutations. (A) 2 kb TT araC $P_{BAD}$c2 fragment inserted into the deletion of entire asd gene. (B) deletion of 41 bp from murA-12 to −53 and inserted 1344 bp $P_{BA-D}$araC::TT with ATG-murA.

Figure 10:
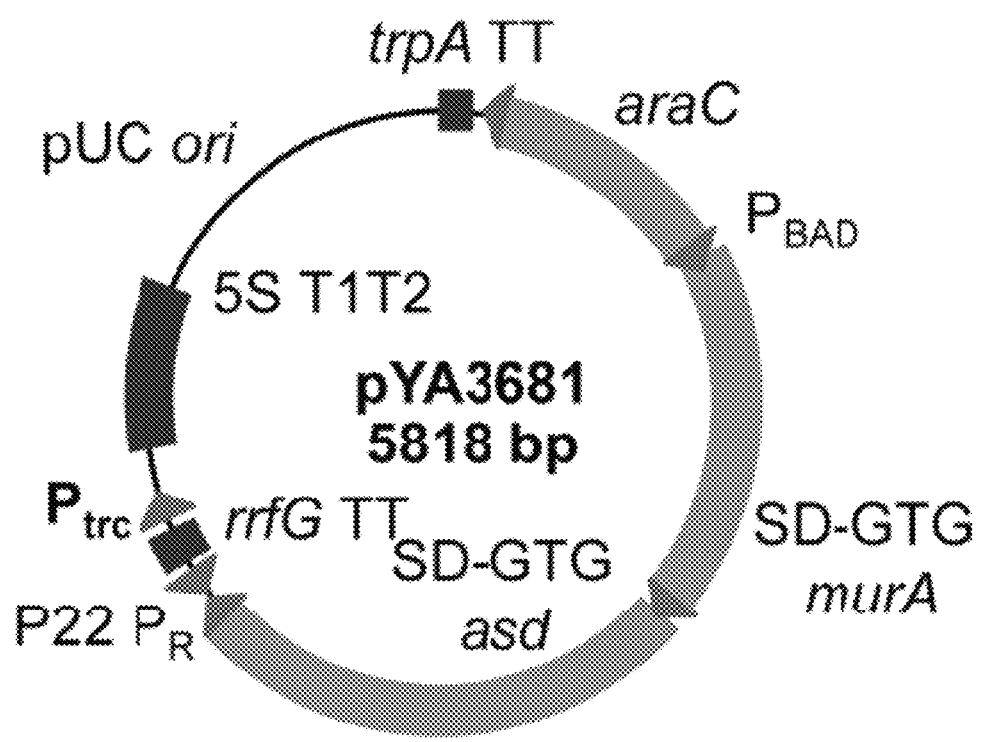

FIG. 10 depicts an illustration of plasmid pYA3681. P: promoter, TT:transcriptional terminator.

Figure 11:
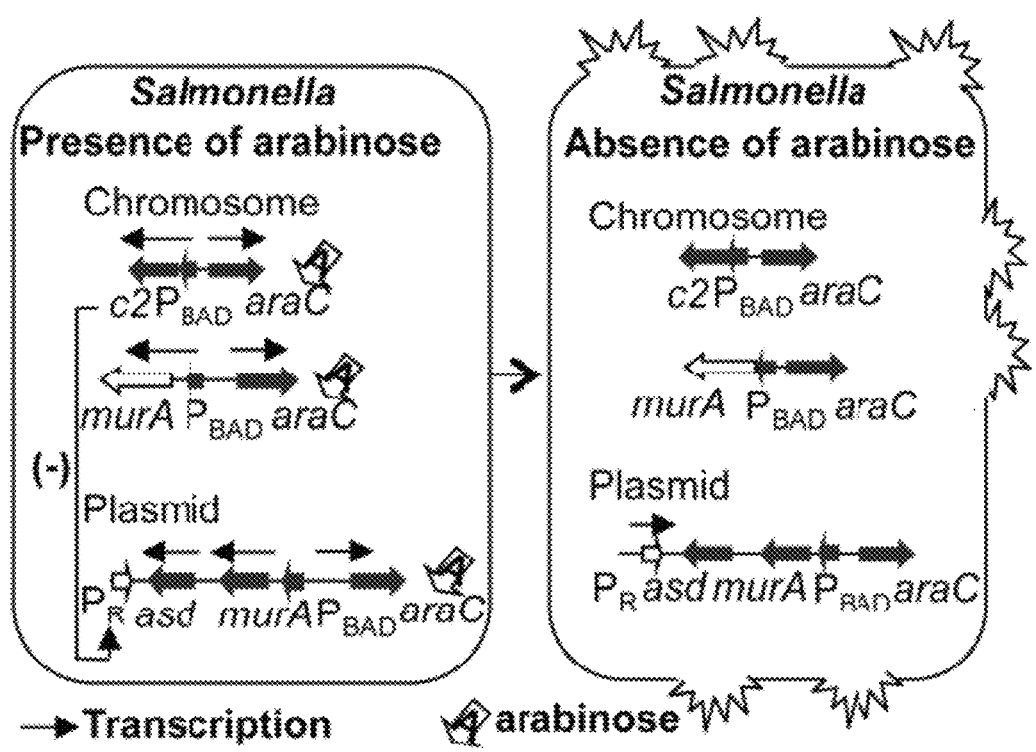

FIG. 11 depicts a diagram of a model illustrating the regulatory interactions in the lysis system.

Figure 12:
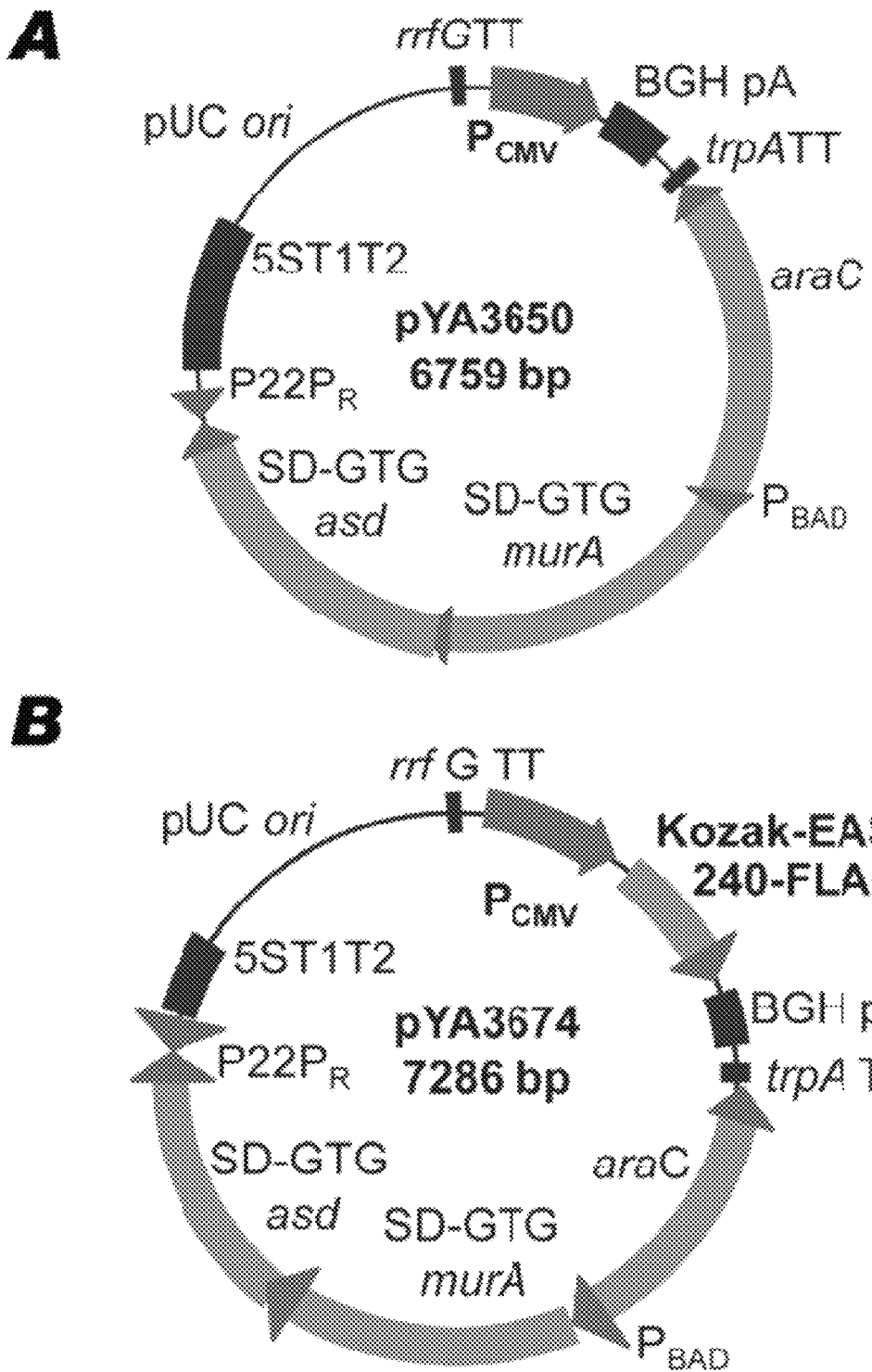

FIG. 12 depicts an illustration of plasmids (A) pYA3650 and (B) pYA3674 (pYA3650 specifying EASZ240-FLAG).

Figure 13:
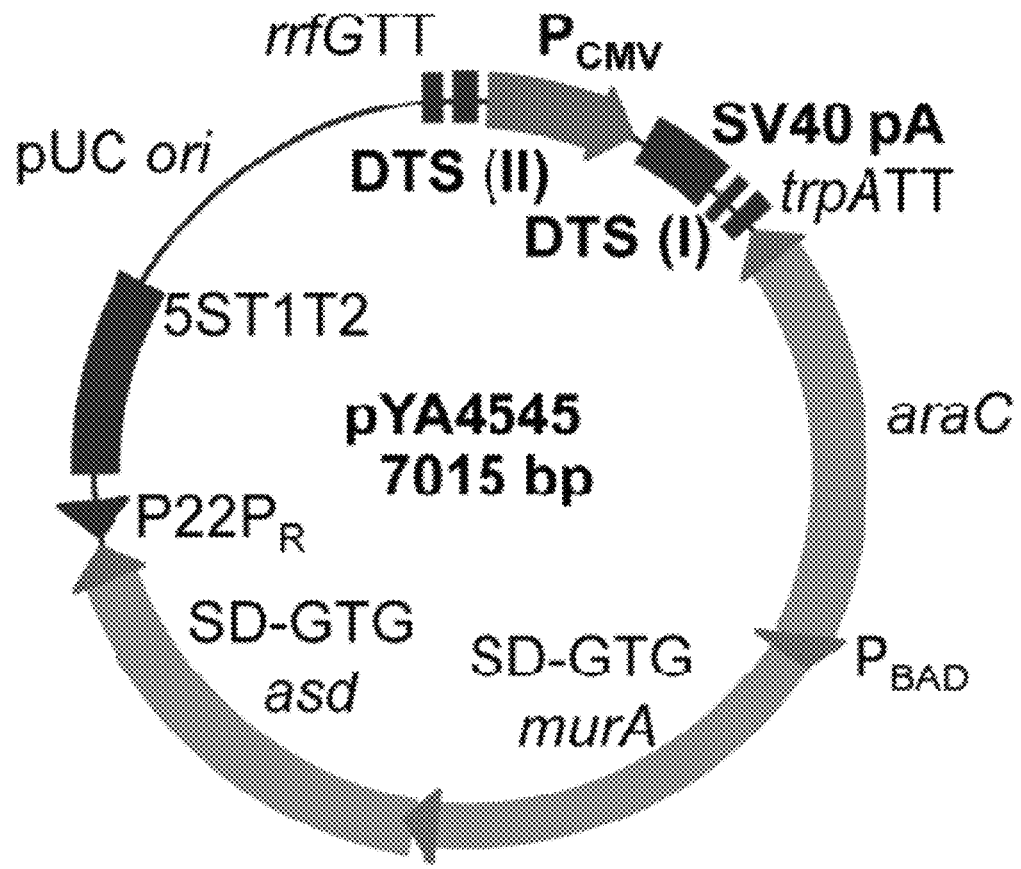

FIG. 13 depicts a diagram of DNA vaccine vector pYA4545 (pYA3650 with DTS (I, II) and SV40 polyA).

Figure 14:
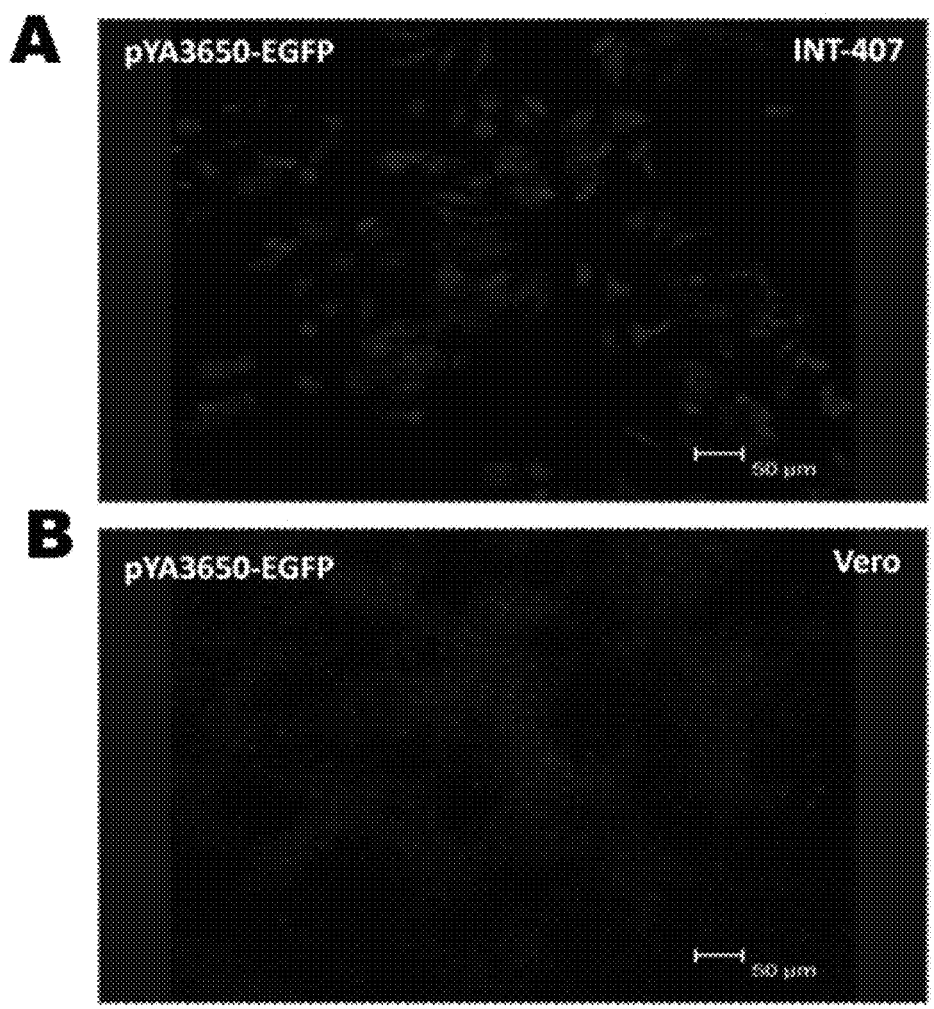
Figure 14:
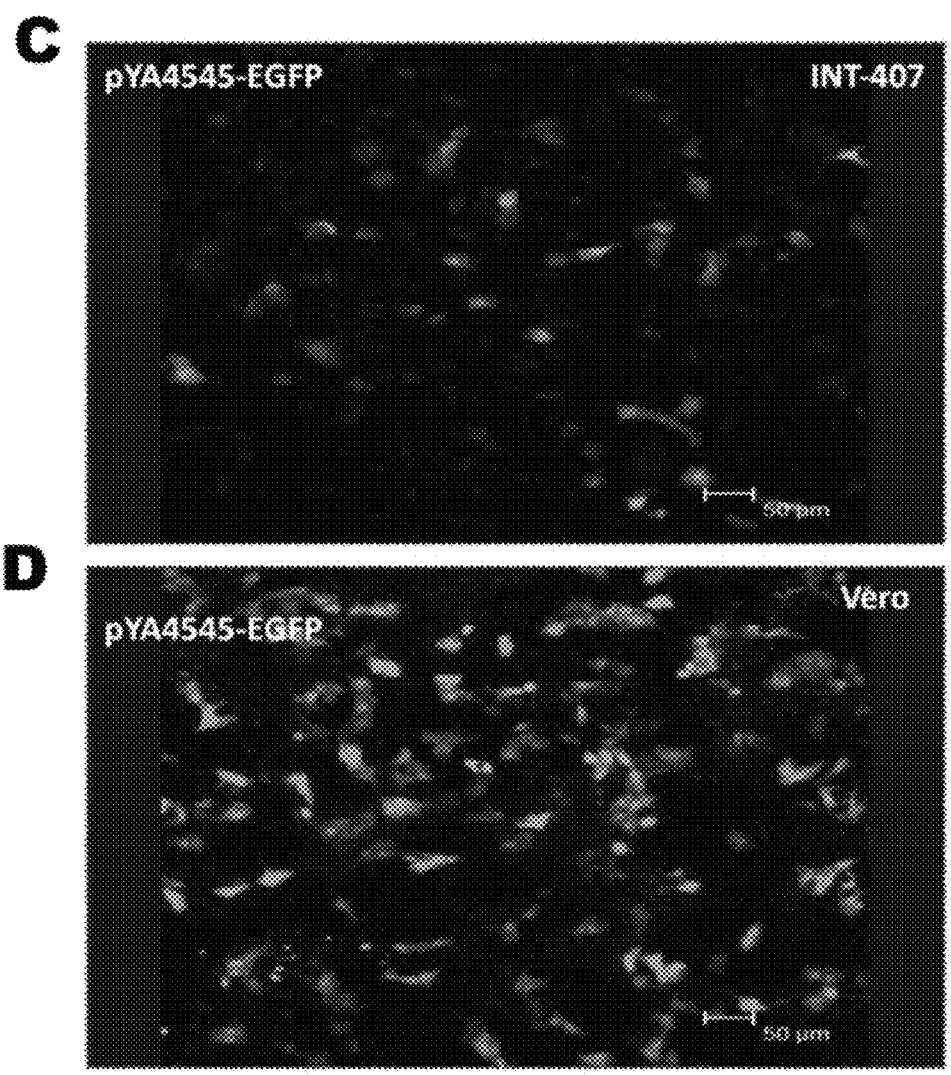

FIG. 14 depicts two photographs showing the synthesis of EGFP from pYA4545 harboring EGFP gene in the INT-407 and Vero cell lines. Transfection of 1 µg DNA, fluorescence of GFP were visualized in the microscope 20 hours post-transfections (ZEISS Axioskop 40, Objective 10×). (A) pYA3650-EGFP in INT-407, (B) pYA3650-EGFP in Vero, (C) pYA4545-EGFP in INT-407, (D) pYA4545-EGFP in Vero.

Figure 15:
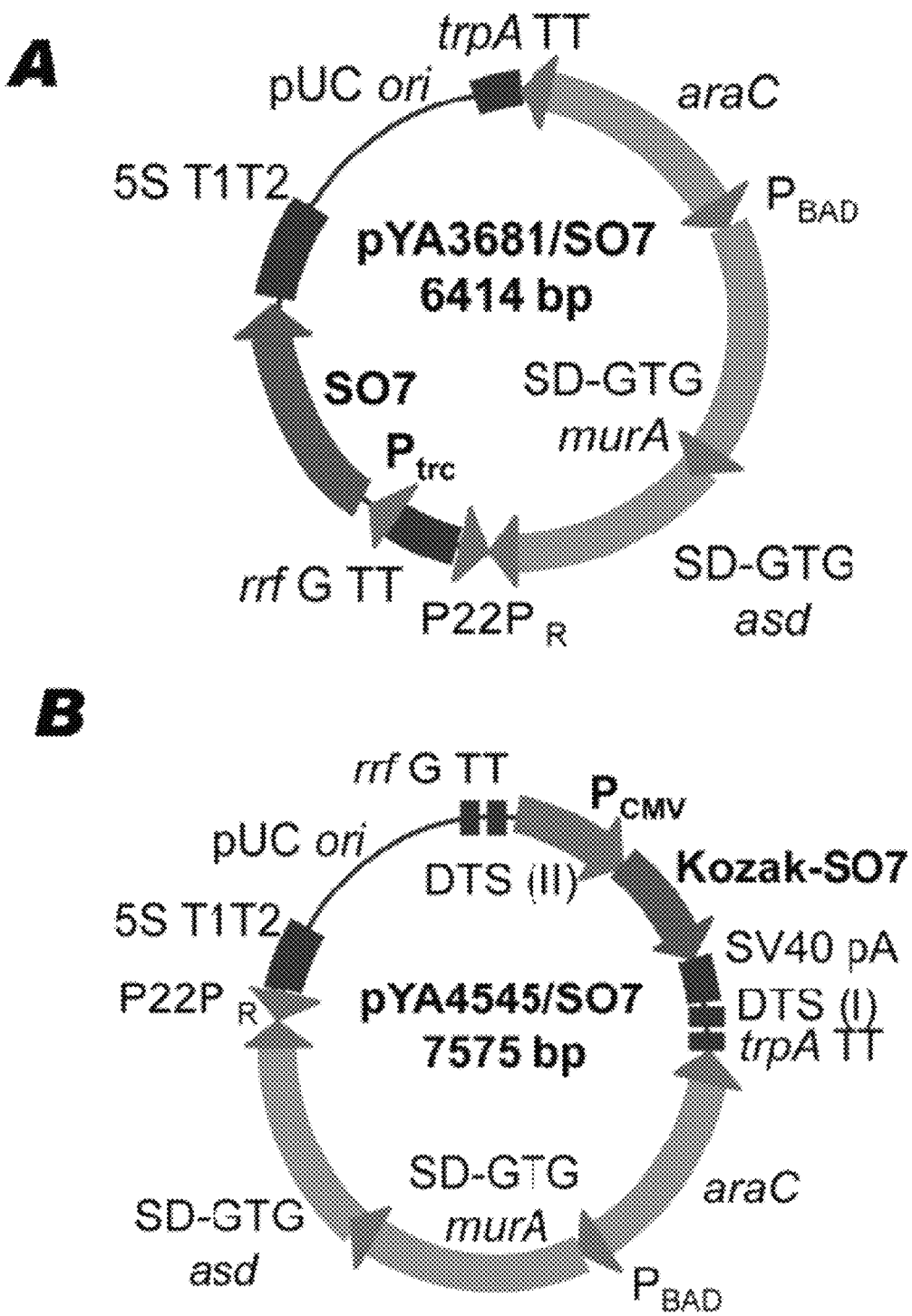
Figure 15:
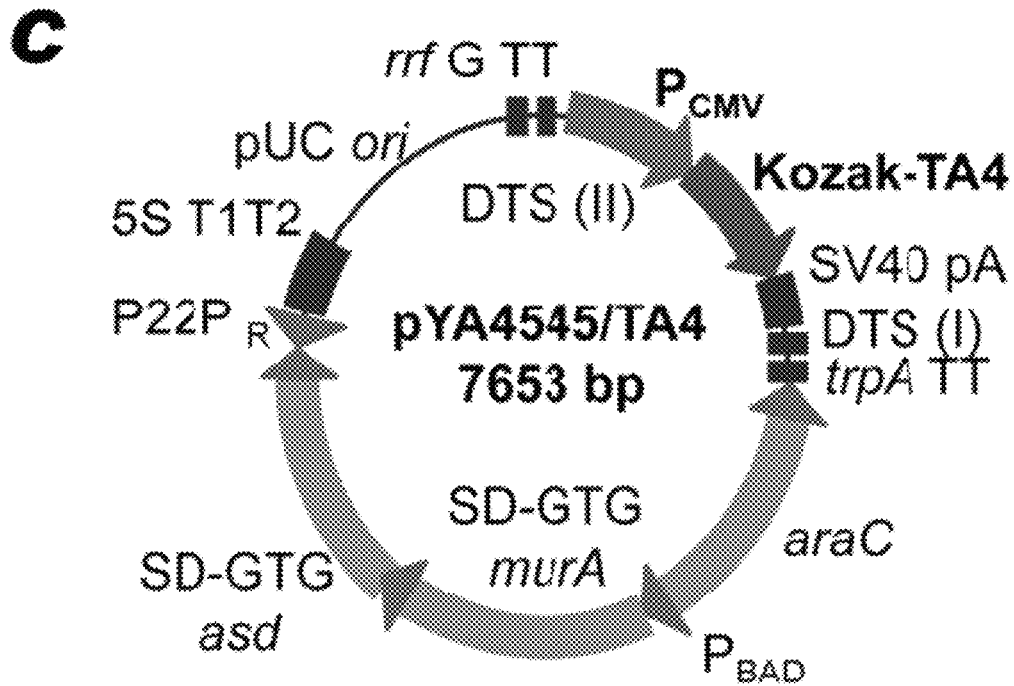
Figure 15:
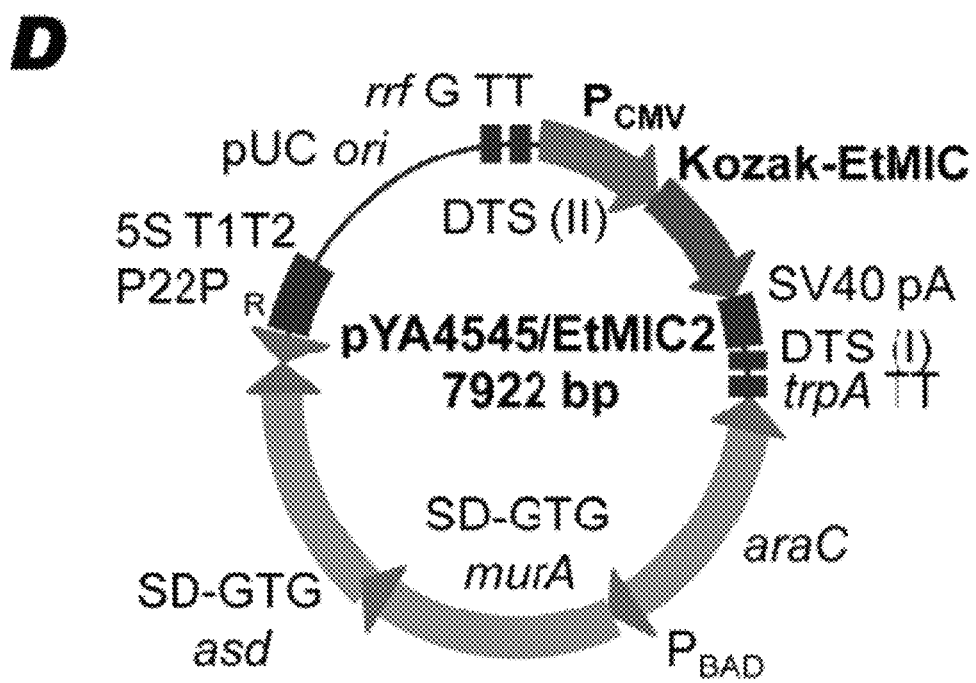

FIG. 15 depicts four vaccine vectors specifying Eimeria antigens. (A) pYA3681 specifying SO7 antigen, (B) pYA4545 specifying SO7 antigen, (C) pYA4545 specifying TA4 antigen, and (D) pYA4545 specifying EfMIC2 antigen.

Figure 16:
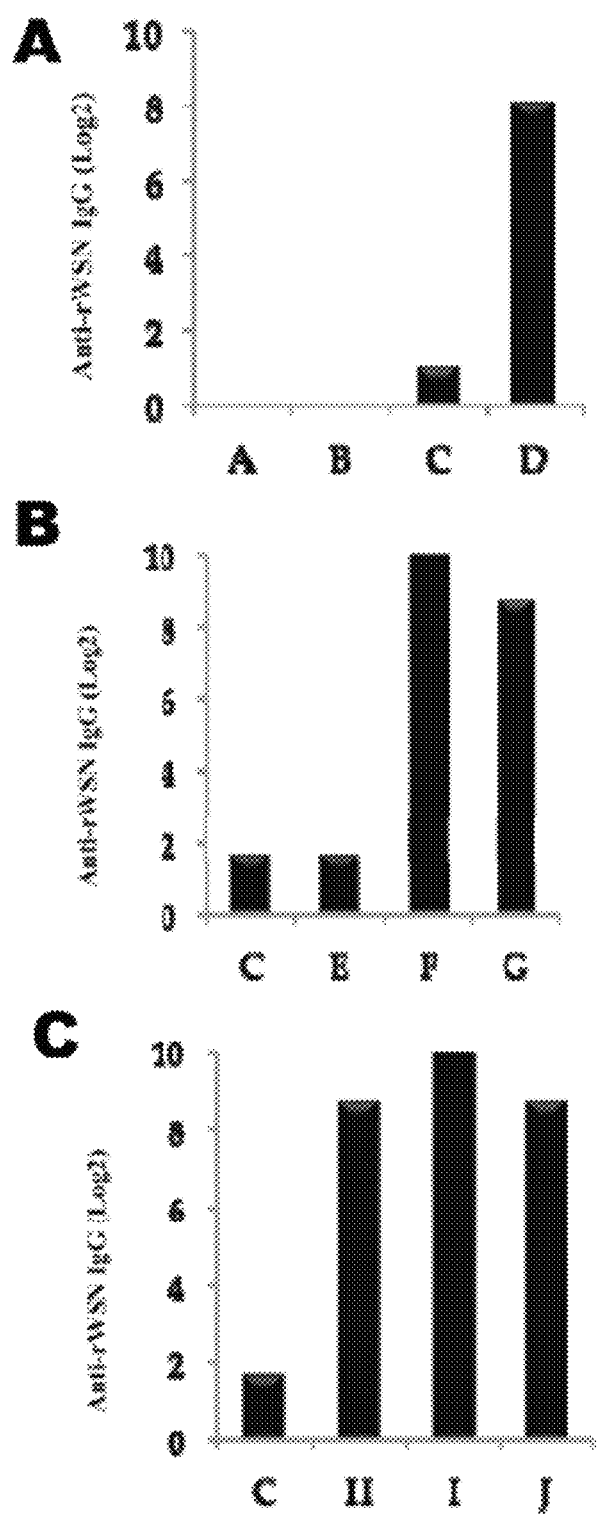

FIG. 16 depicts graphs showing Induction of serum IgG to rWSN at 5 weeks post oral immunization of mice. p<0.05 (A) A. BSG, B. χ9354 (pYA4545), C. χ9354 (pYA4859), D. χ11214 (pYA4859) ($\Delta P_{hilA}::P_{trc\ \Delta lacO}$ hilA); (B) C. χ9354 (pYA4859), E. χ11212 (pYA4859)(ΔtlpA), F. χ11213 (pYA4859)(ΔsseL), G. χ11215 (pYA4859)(ΔtlpA and ΔsseL); (C) C. χ9354 (pYA4859), H. χ11216 (pYA4859) (ΔtlpA, $\Delta P_{hilA}::P_{trc\ \Delta lacO}$ hilA), I. χ11217 (pYA4859) (ΔsseL, $\Delta P_{hilA}::P_{trc\ \Delta lacO}$ hilA), J. χ11218 (pYA4859) (ΔtlpA, ΔsseL, $\Delta P_{hilA}::P_{trc\ \Delta lacO}$ hilA).

Figure 17:
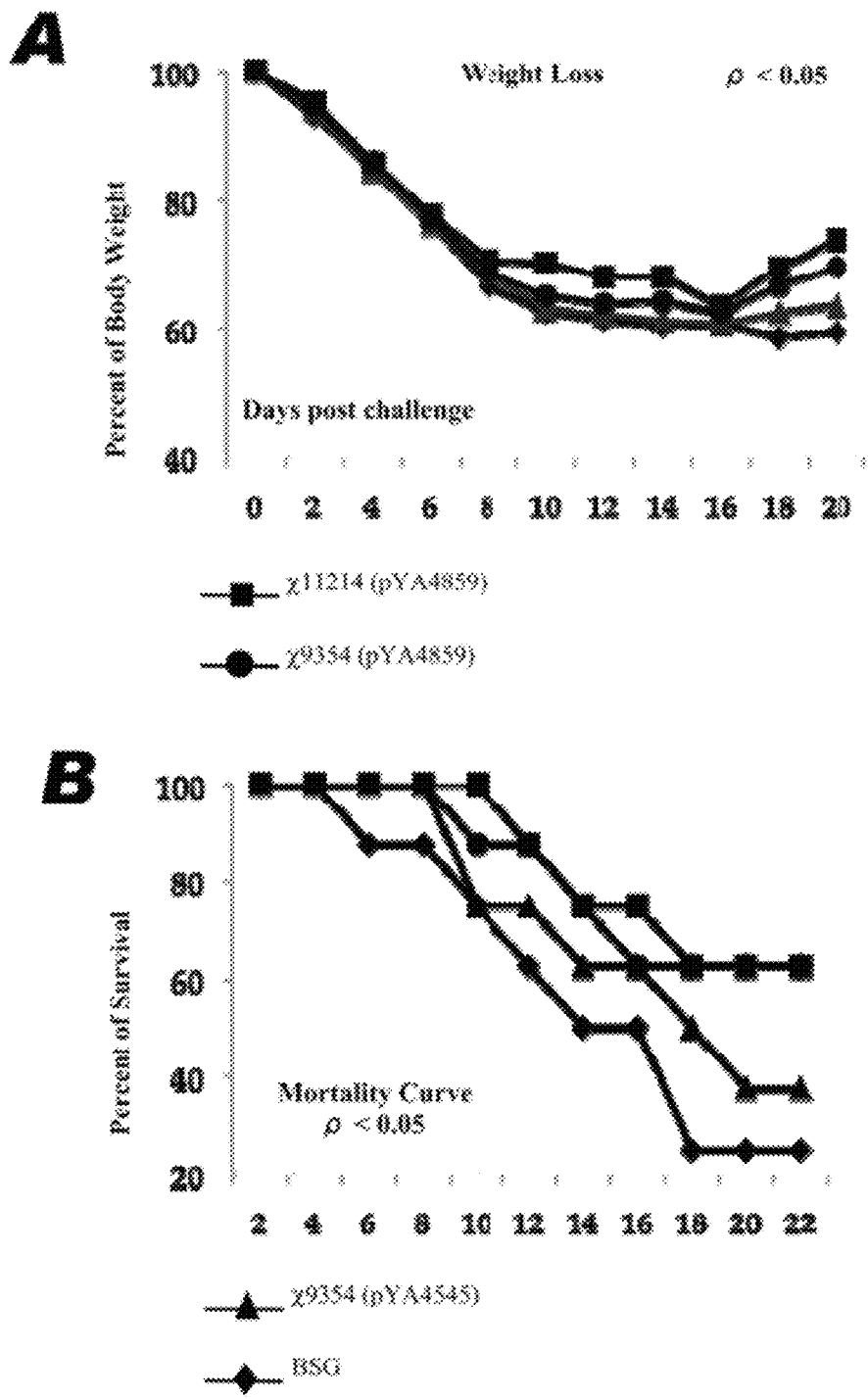

FIG. 17 depicts graphs of (A) Weight loss and (B) mortality curve after challenge of immunized mice with 1×10$^5$ TCID$_{50}$ rWSN. χ9354 (ΔasdA::TT araC $P_{BAD}$ c2 $\Delta P_{murA}$::TT araC $P_{BAD}$ murA ΔaraBAD ΔaraE ΔrelA Δ(gmd-fcl) ΔendA ΔsifA); χ11214 (χ9354 with $\Delta P_{hilA}::P_{trc\ \Delta lacO}$ hilA).

Figure 18:
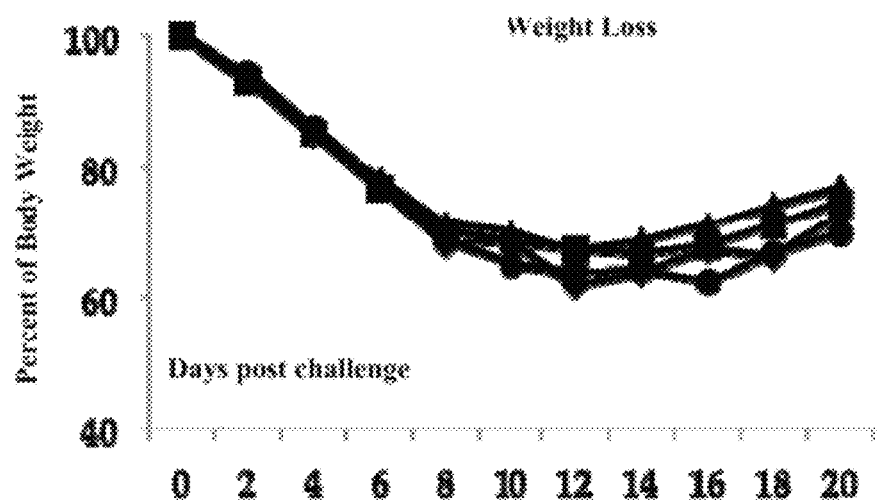
Figure 18:
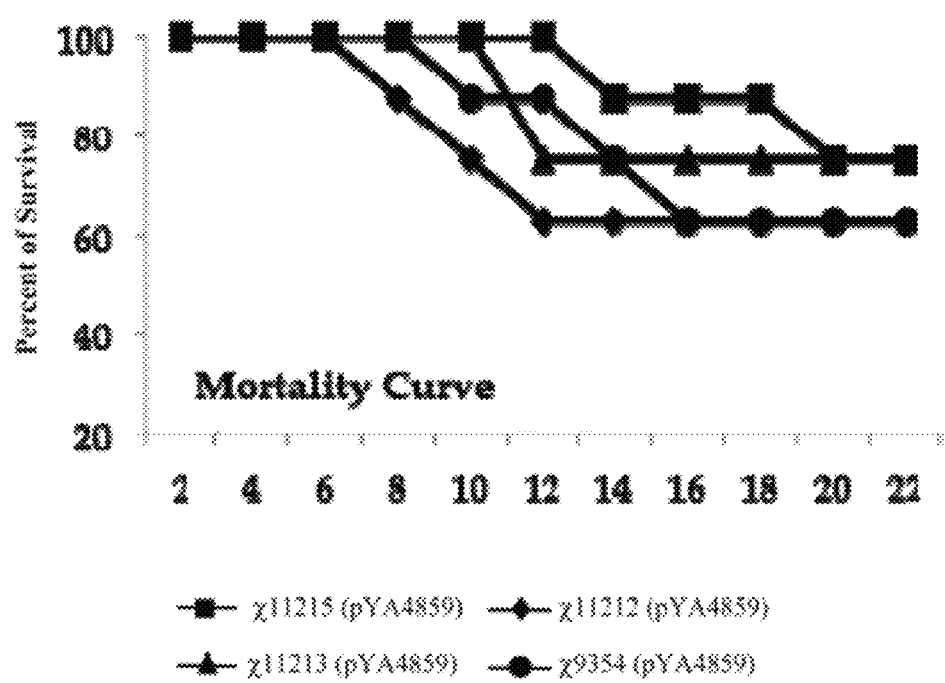

FIG. 18 depicts graphs of (A) Weight loss and (B) mortality curve after challenge of immunized mice with 1×10$^5$ TCID$_{50}$ rWSN. χ9354 (ΔasdA::TT araC $P_{BAD}$ c2 $\Delta P_{murA}$::TT araC $P_{BAD}$ murA ΔaraBAD ΔaraE ΔrelA Δ(gmd-fcl) ΔendA ΔsifA); χ11212 (χ9354 with ΔtlpA); χ11213 (χ9354 with ΔsseL); χ11215 (χ9354 with ΔtlpA and ΔsseL).

Figure 19:
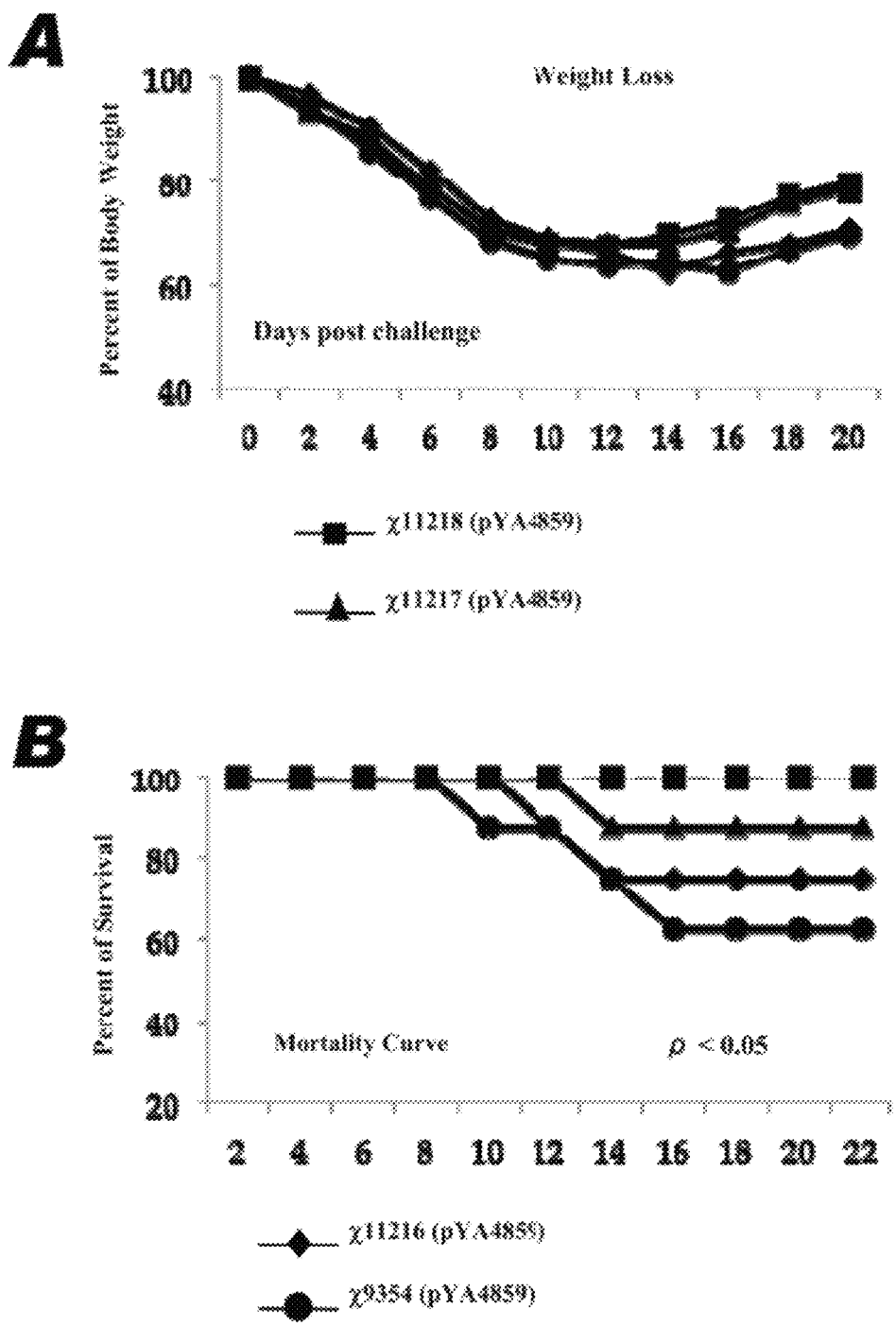

FIG. 19 depicts graphs of (A) Weight loss and (B) mortality curve after challenge of immunized mice with 1×10$^5$ TCID$_{50}$ rWSN. χ9354 (ΔasdA::TT araC $P_{BAD}$ c2 $\Delta P_{murA}$::TT araC $P_{BAD}$ murA ΔaraBAD ΔaraE ΔrelA Δ(gmd-fcl) ΔendA ΔsifA); χ11216 (χ9354 with ΔtlpA, $\Delta P_{hilA}::$ $P_{trc\ \Delta lacO}$ hilA); χ11217 (χ9354 with ΔsseL, $\Delta P_{hilA}::P_{trc\ \Delta lacO}$ hilA); χ11218 (χ9354 with ΔtlpA, Δsse, $\Delta PhilA::P_{trc\ \Delta lacO}$ hilA).

Figure 20:
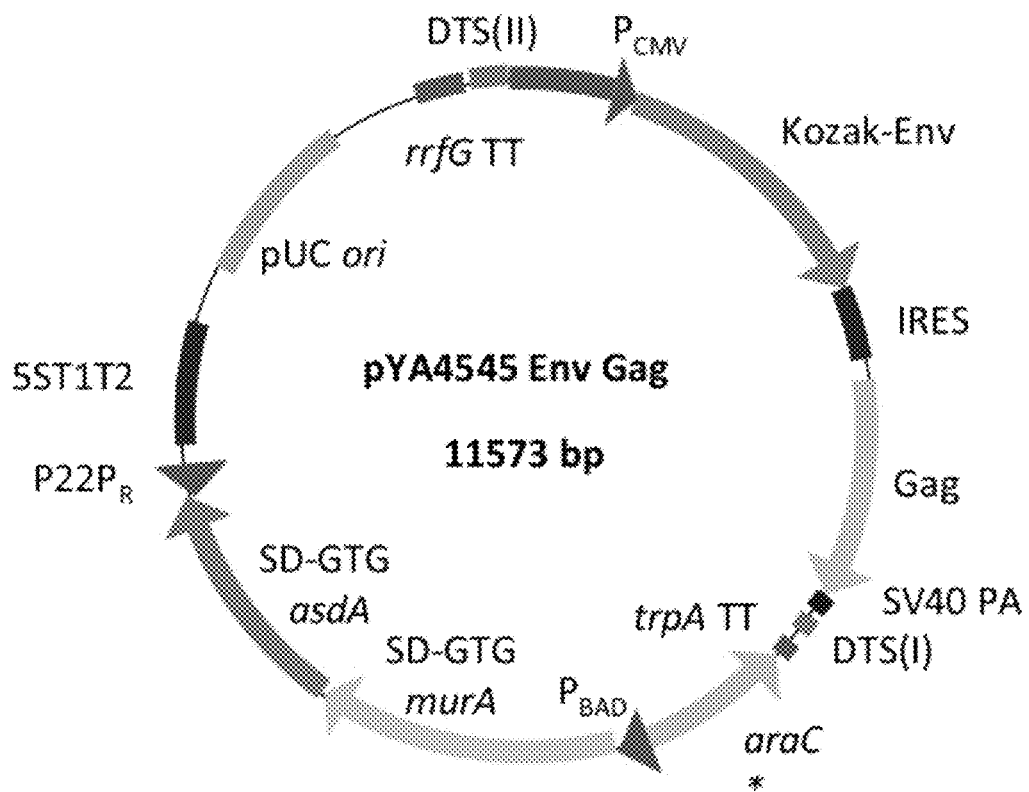

FIG. 20 depicts a map of pYA4545 Env Gag (DNA vaccine vector pYA4545 encoding the optimized HIV-1 Clade B env and gag).

Figure 21:
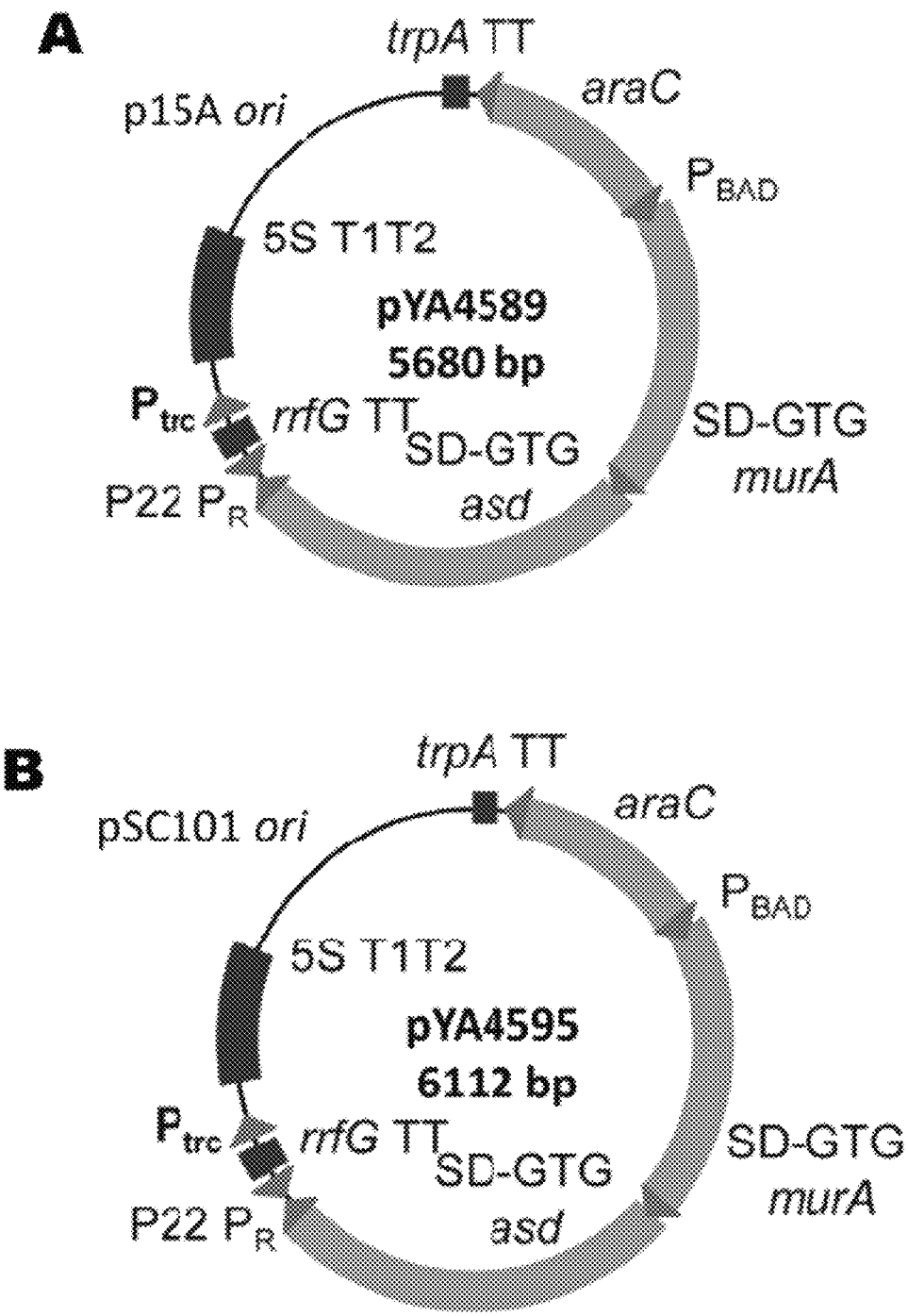
Figure 21:
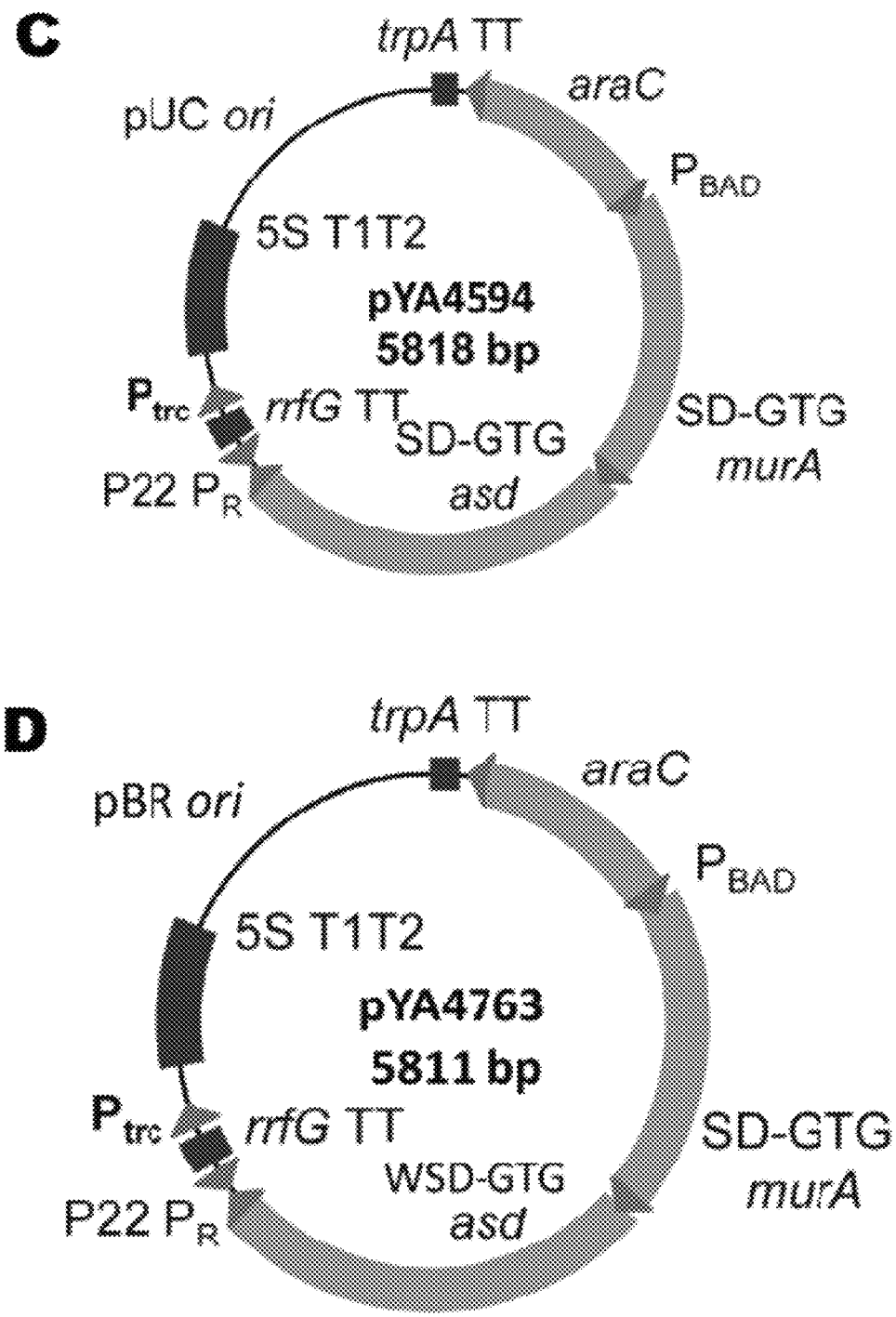

FIG. 21 depicts plasmid maps of pYA3681 derivatives (A) pYA4589, (B) pYA4595, (C) pYA4594, and (D) pYA4763.

Figure 22:
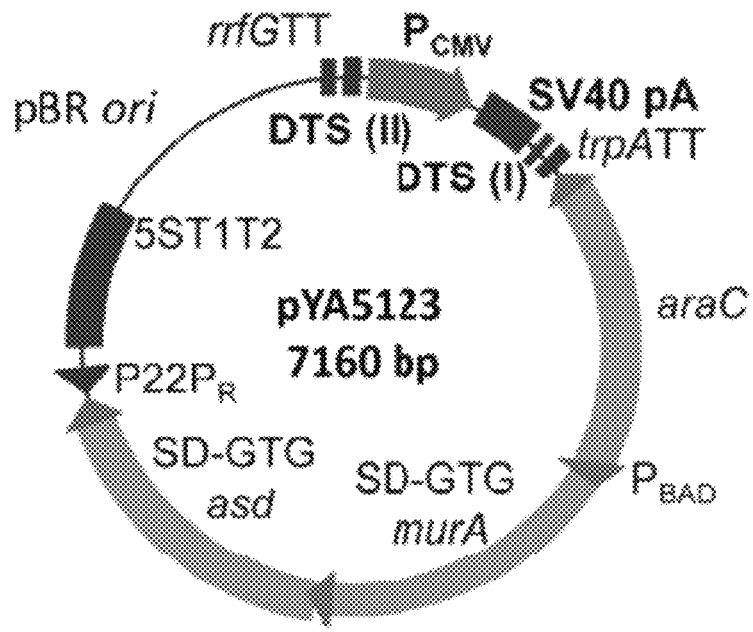
Figure 22:
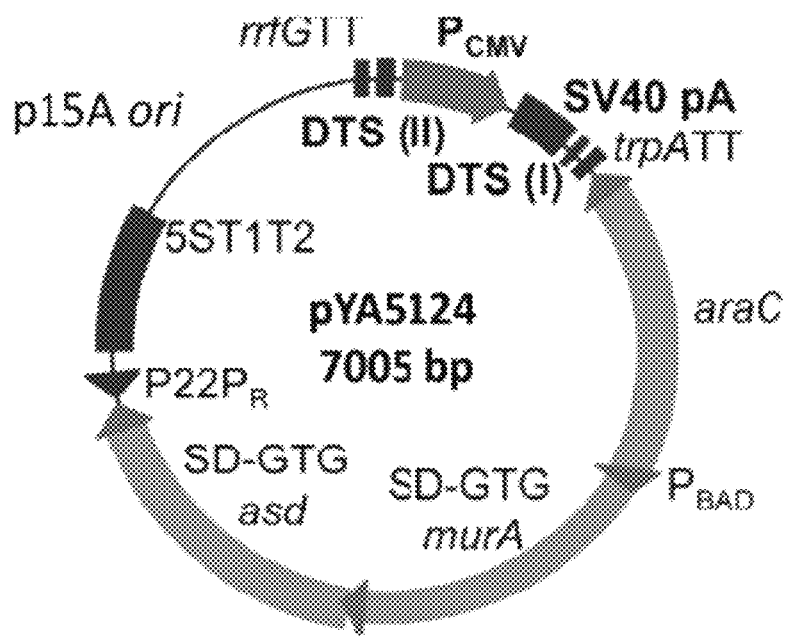
Figure 22C:
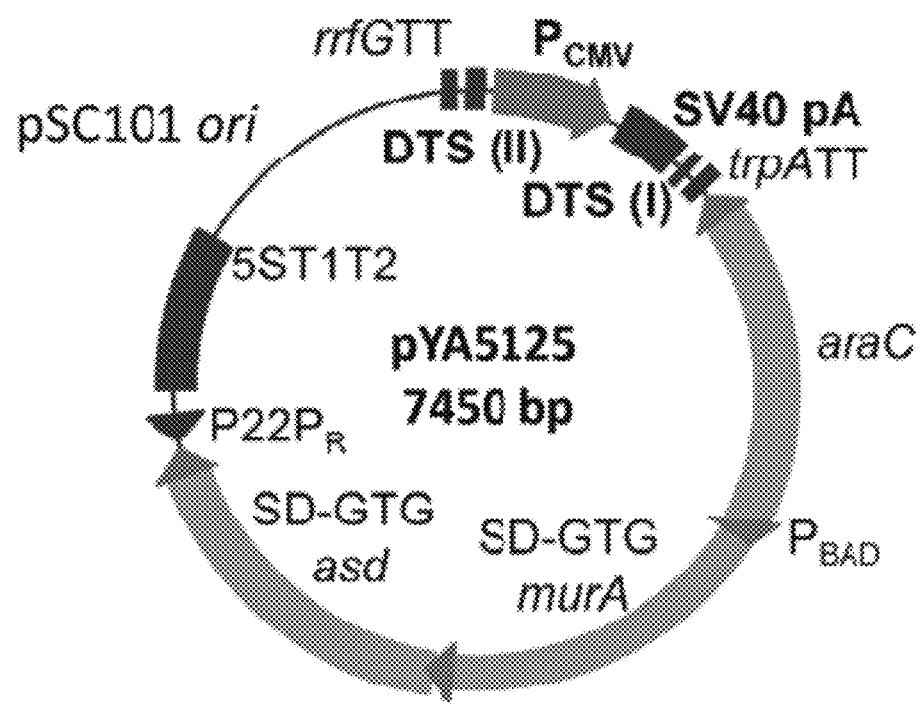

FIG. 22 depicts plasmid maps of pYA4545 derivatives (A) pYA5123, (B) pYA5124, and (C) pYA5125.

Figure 23A:
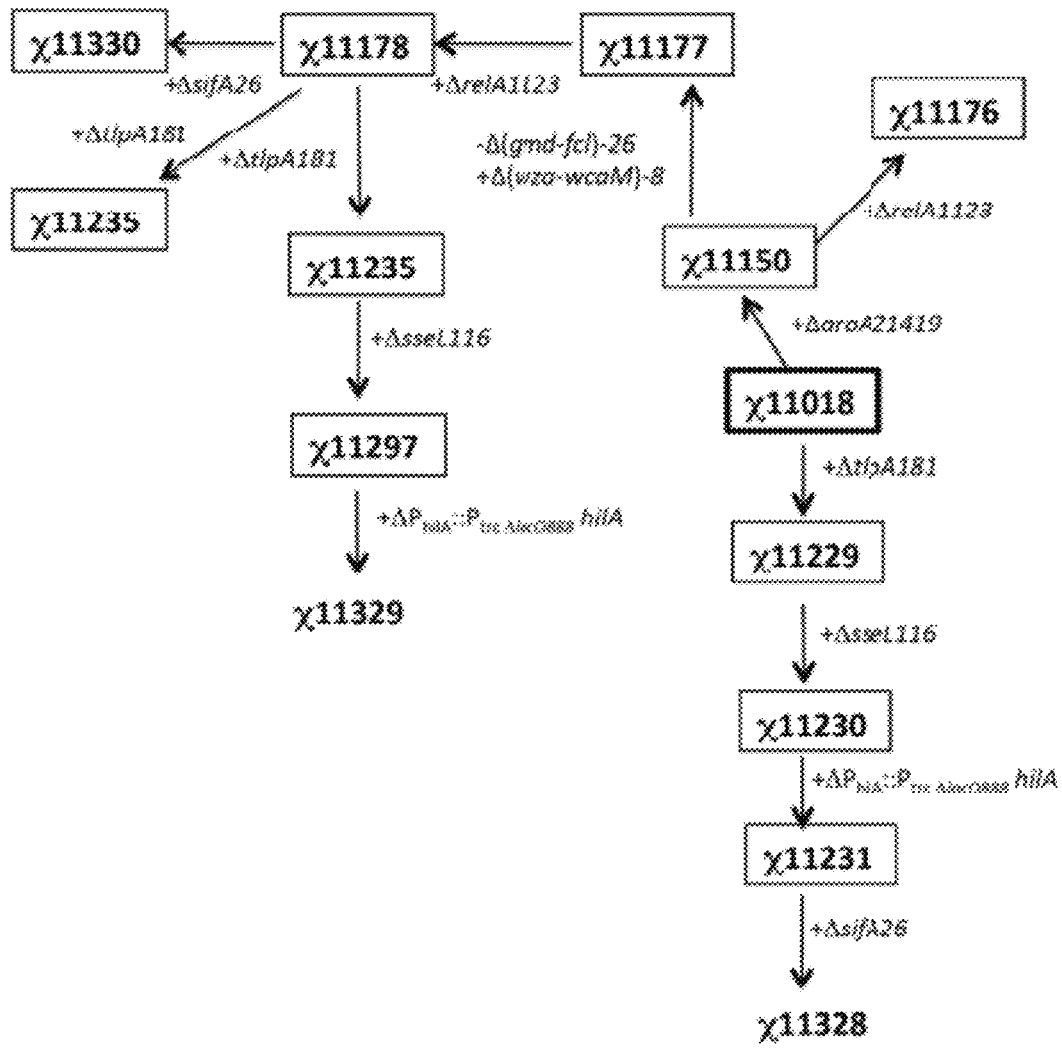
Figure 23B:
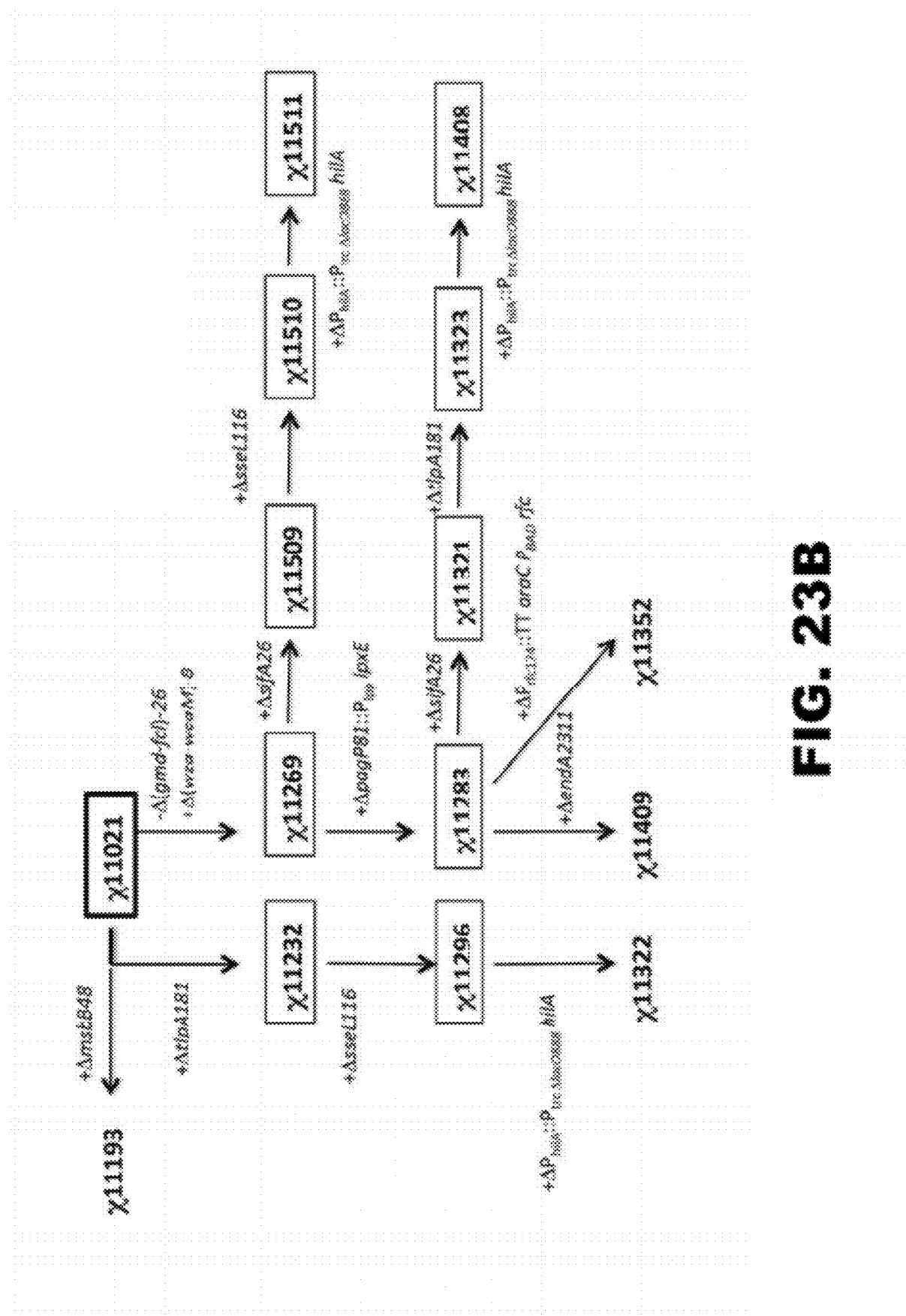

FIG. 23 depicts an illustration of the strain family trees (A) χ11018 and (B) χ11021.

DETAILED DESCRIPTION OF THE INVENTION

The present invention provides a recombinant bacterium that may be used to elicit an immune response from a host. In particular, the bacterium may be used to elicit a cellular immune response by delivering one or more heterologous antigens to the cytosol of a host cell, or delivering a nucleic acid(s) encoding one or more heterologous antigens to the nucleus of a host cell for synthesis of the heterologous antigen. Advantageously, the recombinant bacterium is capable of delaying bacterium-induced host programmed cell death to ensure delivery and/or synthesis of the heterologous antigen. Generally speaking, the bacterium is capable of invading a host cell better than a wild-type bacterium of the same strain, but the bacterium is typically avirulent and is capable of regulated lysis to confer biocontainment. The invention also provides a vaccine comprising a recombinant bacterium of the invention, and methods of eliciting an immune response comprising administering a recombinant bacterium of the invention to a host.

I. Recombinant Bacterium

A recombinant bacterium of the invention typically belongs to the Enterobaceteriaceae. The Enterobacteria family comprises species from the following genera: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. In certain embodiments, the recombinant bacterium is typically a pathogenic species of the Enterobaceteriaceae. Due to their clinical significance, *Escherichia coli, Shigella, Edwardsiella, Salmonella, Citrobacter, Klebsiella, Enterobacter, Serratia, Proteus, Morganella, Providencia* and *Yersinia* are considered to be particularly useful. In other embodiments, the recombinant bacterium may be a species or strain commonly used for a vaccine.

Some embodiments of the instant invention comprise a species or subspecies of the *Salmonella* genera. For instance, the recombinant bacterium may be a *Salmonella enterica* serovar. In an exemplary embodiment, a bacterium of the invention may be derived from *S. Typhimurium, S. typhi, S. paratyphi, S. gallinarum, S. enteritidis, S. choleraesius, S. arizona*, or *S. dublin*.

A recombinant bacterium of the invention derived from *Salmonella* may be particularly suited to use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant *Salmonella* for oral immunization stimulates all three branches of the immune system, which is particularly important for immunizing against infectious disease agents that colonize on and/or invade through mucosal surfaces.

A bacterium of the invention may comprise one or more mutations as detailed below. In particular, a bacterium may comprise one or more mutations to increase invasiveness (section (a) below), one or more mutations to allow endosomal escape (section (b) below), one or more mutations to reduce bacterium-induced host programmed cell death (section (c) below), one or more mutations to induce lysis of the bacterium (section (d) below), one or more mutations to express a nucleic acid encoding an antigen (section (e) below), one or more mutations to attenuate the bacterium (section (f) below), and/or one or more mutations to enhace the performance of the bacterium as a vaccine (section (g) below).

(a) Hyper-Invasiveness

A recombinant bacterium of the invention may also be hyper-invasive. As used herein, "hyper-invasive" refers to a bacterium that can invade a host cell more efficiently than a wild-type bacterium of the same strain. Invasion may be determined by methods known in the art, e.g. CFUs/g of tissue. In some embodiments, a recombinant bacterium may be capable of increased invasion of M cells. Generally speaking, such a bacterium may comprise a mutation that increases expression of hilA. For instance, the promoter of hilA may be mutated to enable constitutive expression of hilA. A non-limiting example may include a $\Delta P_{hilA}::P_{trc\Delta lacO}$ hilA mutation, such as $\Delta P_{hilA}::P_{trc\Delta lacO888}$ hilA. Such a mutation replaces the wild-type hilA promoter with the $P_{trc}$ promoter that lacks the lacO operator sequence. This allows constitutive expression of hilA, even when lacI is expressed. Alternatively, deletion of the lrp nucleic acid sequence may be used to increase hilA expression.

(b) Endosomal Escape

A recombinant bacterium of the invention may be capable of escaping the endosomal compartment of the host cell. Escape from the endosome typically facilitates transfer of a nucleic acid vaccine vector to the nucleus for transcription. Escape may also facilitate delivery of an antigen to the cytosol of the host cell. A recombinant bacterium may escape from the endosome immediately after invasion of the host cell, or alternatively, may delay escape. Methods of detecting escape from the endosomal compartment are well known in the art, and may include microscopic analysis.

In one embodiment, a recombinant bacterium capable of escaping the endosomal compartment comprises a mutation that alters the functioning of SifA. For instance, sifA may be mutated so that the function of the protein encoded by sifA is altered. Non-limiting examples include a mutation that deletes sifA ($\Delta$sifA). Such a mutation allows escape from the endosome upon host-cell invasion. Another example is a $\Delta P_{sifA}::TT$ araC $P_{BAD}$ sifA mutation, which allows delayed escape. Since arabinose is absent in host tissues the expression of the sifA gene ceases and no SifA protein is synthesized such that the amount decreases with each round of bacterial cell division thereby allowing escape from the endosome. Similar delayed escape mutations may be constructed using other regulatable promoters, such as from the xylose or rhamnose regulatory systems.

In another embodiment, a recombinant bacterium capable of escaping the endosomal compartment may comprise a mutation that causes the expression of nucleic acid sequences such as tlyC or pld from *Rickettsiae prowazekii*. The expression may be regulated by an inducible promoter. For instance, the bacterium may comprise an araC $P_{BAD}$ tlyC or an araC $P_{BAD}$ pld mutation. In some embodiments, a bacterium may comprise a sifA mutation and a mutation that causes the expression of tlyC or pld.

(c) Reduced Bacterium-Induced Host Programmed Cell Death

Programmed cell death of a host cell invaded by a bacterium of the invention is likely to diminish the transcription of a nucleic acid sequence comprising a nucleic acid vaccine vector delivered by the bacterium. Consequently, in some embodiments, a recombinant bacterium of the invention may be capable of reducing bacterium-induced host programmed cell death compared to a wild-type bacterium of the same strain. Non-limiting examples of bacterium-induced host programmed cell death may include apoptosis and pyroptosis. Methods of detecting and measuring bacterium-induced host programmed cell death are known in the art.

In one embodiment, a bacterium of the invention capable of reducing bacterium-induced host programmed cell death may comprise a mutation affecting the pathway inducing apoptosis/pyroptosis. Non-limiting examples of such a mutation may include mutations in a deubiquitinase nucleic acid sequence, such as sseL, and/or mutations in a temperature-sensing protein nucleic acid sequence, such as tlpA. For instance, a bacterium may comprise a $\Delta$sseL mutation, a $\Delta$tlpA mutation, or both mutations. In another embodiment, a bacterium may completely lack flagella.

(d) Lysis

In another embodiment, a recombinant bacterium of the invention is capable of regulated lysis. Lysis of the bacterium within the host cell may release a bolus of antigen, or alternatively, may release a nucleic acid vaccine vector for transcription by the host cell. Lysis also provides a means of biocontainment. For additional biocontainment mechanisms, see section (f) below.

In some embodiments, a recombinant bacterium capable of regulated lysis may comprise a mutation in a required constituent of the peptidoglycan layer of the bacterial cell wall. For instance, the bacterium may comprise a mutation in a nucleic acid sequence encoding a protein involved in muramic acid synthesis, such as murA. It is not possible to alter murA by deletion, however, because a $\Delta$murA mutation is lethal and can not be isolated. This is because the missing nutrient required for viability is a phosphorylated muramic acid that cannot be exogenously supplied since enteric bacteria cannot internalize it. Consequently, the murA nucleic acid sequence may be altered to make expression of murA dependent on a nutrient (e.g., arabinose) that can be supplied during the growth of the bacterium. For example, the alteration may comprise a $\Delta P_{murA}::TT$ araC $P_{BAD}$ murA deletion-insertion mutation. During in vitro growth of the bacterium, this type of mutation makes synthesis of muramic acid dependent on the presence of arabinose in the growth medium. During growth of the bacterium in a host, however, arabinose is absent. Consequently, the bacterium is non-viable and/or avirulent in a host unless the bacterium further comprises at least one extrachromosomal vector comprising a nucleic acid sequence, that when expressed, substantially functions as murA. Recombinant bacteria with a $\Delta P_{murA}::TT$ araC $P_{BAD}$ murA deletion-insertion mutation grown in the presence of arabinose exhibit effective colonization of effector lymphoid tissues after oral vaccination prior to cell death due to cell wall-less lysing.

Similarly, in various embodiments a recombinant bacterium may comprise the araC $P_{BAD}$ c2 cassette inserted into the asdA nucleic acid sequence that encodes aspartate semialdehyde dehydrogenase, a necessary enzyme for DAP synthesis, a required component of the peptidoglycan layer of the bacterial cell wall. The chromosomal asdA nucleic acid sequence is typically inactivated to enable use of plasmid vectors encoding the wild-type asdA nucleic acid sequence in the balanced-lethal host-vector system. This allows stable maintenance of plasmids in vivo in the absence of any drug resistance attributes that are not permissible in live bacterial vaccines.

In one embodiment, ΔasdA27::TT araC $P_{BAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{BAD}$ c2 has the 1104 base-pair asdA nucleic acid sequence deleted (1 to 1104, but not including the TAG stop codon) and the 1989 base-pair fragment containing T4 ipIII TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA.

In exemplary embodiments, the bacterium may comprise a mutation in the murA nucleic acid sequence encoding the first enzyme in muramic acid synthesis and the asdA nucleic acid sequence essential for DAP synthesis. By way of non-limiting example, these embodiments may comprise the chromosomal deletion-insertion mutations ΔasdA19::TT araC $P_{BAD}$ c2 or ΔasdA27::TT araC $P_{BAD}$ c2 and Δ$P_{murA7}$::TT araC $P_{BAD}$ murA or Δ$P_{murA12}$::TT araC $P_{BAD}$ murA or Δ$P_{murA25}$::TT araC $P_{BAD}$ murA. This host-vector grows in LB broth with 0.1% L-arabinose, but is unable to grow in or on media devoid of arabinose since it undergoes cell wall-less death by lysis.

Bacterium that comprise these mutations also comprise a plasmid that contains a nucleic acid sequence that substitutes for murA and asdA. This allows the bacterium to grow in permissive environments, e.g. when arabinose is present. For instance plasmid vector pYA3681 (FIG. 10) contains the murA nucleic acid sequence (with altered start codon sequences to decrease translation efficiency) under the control of an araC $P_{BAD}$ promoter. The second nucleic acid sequence under the direction of this promoter is the asdA nucleic acid sequence (with altered start codon sequences to decrease translation efficiency). The P22 $P_R$ promoter is in the anti-sense direction of both the asdA nucleic acid sequence and the murA nucleic acid sequence. The P22 $P_R$ is repressed by the C2 repressor made during growth of the strain in media with arabinose (due to the ΔasdA::TT araC $P_{BAD}$ c2 deletion-insertion). However C2 concentration decreases due to cell division in vivo to cause $P_R$ directed synthesis of anti-sense mRNA to further block translation of asdA and murA mRNA. The araC $P_{BAD}$ sequence is also not from E. coli B/r as originally described but represents a sequence derived from E. coli K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asdA nucleic acid sequence does not replace the chromosomal asdA mutation since they have a deleted sequence in common. Additionally, the E. coli murA nucleic acid sequence was used in the plasmid instead of using the Salmonella murA nucleic acid sequence. In addition to being fully attenuated, this construction exhibits complete biological containment. This property enhances vaccine safety and minimizes the potential for vaccination of individuals not intended for vaccination.

One of skill in the art will recognize that other nutrients besides arabinose may be used in the above mutations. By way of non-limiting example, xylose, mannose, and rhamnose regulatory systems may also be used.

In some embodiments of the invention, the recombinant bacterium may further comprise araBAD and araE mutations to preclude breakdown and leakage of internalized arabinose such that asdA and murA nucleic acid sequence expression continues for a cell division or two after oral immunization into an environment that is devoid of external arabinose. Additionally, a bacterium may comprise a mutation in a protein involved in GDP-fucose synthesis to preclude formation of colonic acid. Non-limiting examples of such a mutation include Δ(gmd-fcl). A bacterium may also comprise a mutation like ΔrelA that uncouples cell wall-less death from dependence on protein synthesis.

Lysis of the bacterium will typically release lipid A, an endotoxin. So, a bacterium of the invention may comprise a mutation that reduces the toxicity of lipid A. Non-limiting examples may include a mutation that causes synthesis of the mono-phosphoryl lipid A. This form of lipid A is non-toxic, but still serves as an adjuvant agonist.

Alternatively, a recombinant bacterium of the invention may comprise a lysis sytem disclosed in Kong et al., (2008) PNAS 105:9361 or US Patent Publication No. 2006/0140975, each of which is hereby incorporated by reference in its entirety.

(e) Antigen Expression

A recombinant bacterium of the invention may express or deliver one or more nucleic acids that encode one or more antigens. For instance, in one embodiment, a recombinant bacterium may be capable of the regulated expression of a nucleic acid sequence encoding an antigen. In another embodiment, a recombinant bacterium may comprise a nucleic acid vaccine vector. In yet another embodiment, a recombinant bacterium may comprise an eight unit viral cassette. Each of the above embodiments is described in more detail below. Other means of expressing or delivering one or more nucleic acids that encode one or more antigens are known in the art.

In one embodiment, the antigen is an Eimeria antigen. For instance, non-limiting examples of Eimeria antigens may include EASZ240, EAMZ250, TA4, EtMIC2, or SO7. In another embodiment, the antigen may be a viral antigen. For example, the antigen may be an influenza antigen. Non-limiting examples of influenza antigens may include M2e, nucleoprotein (NP), hemagglutinin (HA), and neuraminidase (NA). Antigens may be fused to a protein to enhance antigen processing within a host cell. For instance, an antigen may be fused with SopE, SptP, woodchuck hepatitis core antigen, or HBV core antigen. Additional examples of antigens may be found in sections i., ii., and iii. below and in the Examples.

Antigens of the invention may be delivered via a type 2 or a type 3 secretion system. For more details, see the Examples.

i. Regulated Expression

The present invention encompasses a recombinant bacterium capable of the regulated expression of at least one nucleic acid sequence encoding an antigen of interest. Generally speaking, such a bacterium comprises a chromosomally integrated nucleic acid sequence encoding a repressor and a vector. Each is discussed in more detail below.

A. Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA nucleic acid sequence.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

1. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid sequence encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli* if the recombinant bacterium is from the genus *Salmonella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

2. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system which has been shown to work as a strong promoter induced by the addition of low levels of arabinose (5). The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC-araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium*

P$_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid sequence encodes MalT, a positive regulator of four maltose-responsive promoters (P$_{PQ}$, P$_{EFG}$, P$_{KBM}$, and P$_{S}$). The combination of malT and a mal promoter creates a tightly regulated expression system that has been shown to work as a strong promoter induced by the addition of maltose (6). Unlike the araC-P$_{BAD}$ system, malT is expressed from a promoter (P$_{T}$) functionally unconnected to the other mal promoters. P$_{T}$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as P$_{KBM}$, and the portion of the malEFG-malKBM promoter that mediates expression of the malEFG nucleic acid sequence, and that is controlled by the malT nucleic acid sequence product, is referred to herein as P$_{EFG}$. Full induction of P$_{KBM}$ requires the presence of the MalT binding sites of P$_{EFG}$. For use in the vectors and systems described herein, a cassette with the malT nucleic acid sequence and one of the mal promoters may be used. This cassette is referred to herein as malT-P$_{mal}$. In the presence of maltose, the MalT protein is a positive regulatory element that allows expression from P$_{mal}$.

In still other embodiments, the promoter may be sensitive to the level of rhamnose in the environment. Analogous to the araC-P$_{BAD}$ system described above, the rhaRS-P$_{rhaB}$ activator-promoter system is tightly regulated by rhamnose. Expression from the rhamnose promoter (P$_{rha}$) is induced to high levels by the addition of rhamnose, which is common in bacteria but rarely found in host tissues. The nucleic acid sequences rhaBAD are organized in one operon that is controlled by the P$_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the P$_{rhaRS}$ promoter and activates the production of RhaR and RhaS. RhaS together with L-rhamnose in turn binds to the P$_{rhaBAD}$ and the P$_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC P$_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the P$_{rhaBAD}$ promoter. In some embodiments, the rhaRS-P$_{rhaB}$ activator-promoter cassette from E. coli K-12 strain may be inserted into vector pCR 2.1 to result in plasmid pYA5081.

In still other embodiments, the promoter may be sensitive to the level of xylose in the environment. The xylR-P$_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-P$_{BAD}$ system described above, the xylR-P$_{xylAB}$ and/or xylR-P$_{xylFGH}$ regulatory systems may be used in the present invention. In these embodiments, xylR P$_{xylAB}$ xylose interacting with the XylR protein activates transcription of nucleic acid sequences operably-linked to either of the two P$_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

3. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid sequence encoding an antigen of interest, and is substantially not synthesized in a non-permissive environment, thereby allowing expression of the nucleic acid sequence encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

4. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

B. Vector

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host. In certain embodiments, however, the promoter may also be regulated by a plasmid encoded repressor.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

1. Antigen

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against or reduces the persistence of the pathogen in the host. For example, a protective antigen from a pathogen, such as *Mycobacterium*, may induce an immune response that helps to ameliorate symptoms associated with *Mycobacterium* infection or reduce the morbidity and mortality associated with infection with the pathogen. The use of the term "protective" in this invention does not necessarily require that the host is completely protected from the effects of the pathogen.

Antigens may be from bacterial, viral, mycotic and parasitic pathogens, and may be designed to protect against bacterial, viral, mycotic, and parasitic infections, respectively. Alternatively, antigens may be derived from gametes, provided they are gamete specific, and may be designed to block fertilization. In another alternative, antigens may be tumor antigens, and may be designed to decrease tumor growth. It is specifically contemplated that antigens from organisms newly identified or newly associated with a disease or pathogenic condition, or new or emerging pathogens of animals or humans, including those now known or identified in the future, may be expressed by a bacterium detailed herein. Furthermore, antigens for use in the invention are not limited to those from pathogenic organisms. Immunogenicity of the bacterium may be augmented and/or modulated by constructing strains that also express sequences for cytokines, adjuvants, and other immunomodulators.

Some examples of microorganisms useful as a source for antigen are listed below. These may include microoganisms for the control of plague caused by *Yersinia pestis* and other *Yersinia* species such as *Y. pseudotuberculosis* and *Y. enterocolitica*, for the control of gonorrhea caused by *Neisseria gonorrhoea*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Erysipelothrix rhusiopathiae*, *Neisseria meningitidis*, *Mycoplasma pneumoniae* and other *Mycoplasma*-species, *Hemophilus influenza*, *Bordetella pertussis*, *Mycobacterium tuberculosis*, *Mycobacterium leprae*, other *Bordetella* species, *Escherichia coli*, *Streptococcus equi*, *Streptococcus pneumoniae*, *Brucella abortus*, *Pasteurella hemolytica* and *P. multocida*, *Vibrio cholera*, *Shigella* species, *Borrellia* species, *Bartonella* species, *Heliobacter pylori*, *Campylobacter* species, *Pseudomonas* species, *Moraxella* species, *Brucella* species, *Francisella* species, *Aeromonas* species, *Actinobacillus* species, *Clostridium* species, *Rickettsia* species, *Bacillus* species, *Coxiella* species, *Ehrlichia* species, *Listeria* species, and *Legionella pneumophila* are additional examples of bacteria within the scope of this invention from which antigen nucleic acid sequences could be obtained. Viral antigens may also be used. Viral antigens may be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. In one embodiment, the antigen is an influenza antigen. Antigens may also be derived from pathogenic fungi, protozoa and parasites. For instance, by way of non-limiting example, the antigen may be an *Eimeria* antigen, a *Plasmodium* antigen, or a *Taenia solium* antigen.

Certain embodiments encompass an allergen as an antigen. Allergens are substances that cause allergic reactions in a host that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual hosts will vary for any particular allergen. It is possible to induce tolerance to an allergen in a host that normally shows an allergic response. The methods of inducing tolerance are well-known and generally comprise administering the allergen to the host in increasing dosages.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tenus toxin fragment C, CT-B, LT-B and hepatitis virus B core are particularly useful for these purposes, although other epitope presentation systems such as hepatitis B virus and woodchuck hepatitis virus cores are well known in the art.

In further embodiments, a nucleic acid sequence encoding an antigen of the invention may comprise a secretion signal. In other embodiments, an antigen of the invention may be toxic to the recombinant bacterium.

2. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

3. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art.

ii. Eight Unit Viral Vector

A single expression vector capable of generating an attenuated virus from a segmented genome has been developed. An auxotrophic bacterial carrier can carry and deliver this expression vector into in vitro cultured cells, resulting in the recovery of virus, either attenuated or non-attenuated. Advantageously, the expression vector is stable in bacteria at 37° C., and produces higher titers of virus than traditional multi-vector systems when transfected into eukaryotic cells.

The expression vector generally comprises a plasmid having at least two types of transcription cassettes. One type of transcription cassette is designed for vRNA production. The other type of transcription cassette is designed for the production of both vRNAs, and mRNAs. As will be appreciated by a skilled artisan, the number of transcription cassettes, and their placement within the vector relative to each other, can and will vary depending on the segmented virus that is produced. Each of these components of the expression vector is described in more detail below.

The expression vector may be utilized to produce several different segmented and nonsegmented viruses. Viruses that may be produced from the expression vector include positive-sense RNA viruses, negative-sense RNA viruses and double-stranded RNA (ds-RNA) viruses.

In one embodiment, the virus may be a positive-sense RNA virus. Non-limiting examples of positive-sense RNA virus may include viruses of the family Arteriviridae, Caliciviridae, Coronaviridae, Flaviviridae, Picornaviridae, Roniviridae, and Togaviridae. Non-limiting examples of positive-sense RNA viruses may include SARS-coronavirus, Dengue fever virus, hepatitis A virus, hepatitis C virus, Norwalk virus, rubella virus, West Nile virus, Sindbis virus, Semliki forest virus and yellow fever virus.

In one embodiment, the virus may be a double-stranded RNA virus. Non-limiting examples of segmented double-stranded RNA viruses may include viruses of the family Reoviridae and may include aquareovirus, blue tongue virus, coltivirus, cypovirus, fijivirus, idnoreovirus, mycoreovirus, orbivirus, orthoreovirus, oryzavirus, phytoreovirus, rotavirus and seadornavirus.

In yet another embodiment, the virus may be a negative-sense RNA virus. Negative-sense RNA viruses may be viruses belonging to the families Orthomyxoviridae, Bunyaviridae, and Arenaviridae with six-to-eight, three, or two negative-sense vRNA segments, respectively. Non-limiting examples of negative-sense RNA viruses may include thogotovirus, isavirus, bunyavirus, hantavirus, nairovirus, phlebovirus, tospovirus, tenuivirus, ophiovirus, arenavirus, deltavirus and influenza virus.

In another aspect, the invention provides an expression vector capable of generating influenza virus. There are three known genera of influenza virus: influenza A virus, influenza B virus and influenza C virus. Each of these types of influenza viruses may be produced utilizing the single expression vector of the invention.

In one exemplary embodiment, the expression vector is utilized to produce Influenza A virus. Influenza A viruses possess a genome of 8 vRNA segments, including PA, PB1, PB2, HA, NP, NA, M and NS, which encode a total of ten to eleven proteins. To initiate the replication cycle, vRNAs and viral replication proteins must form viral ribonucleoproteins (RNPs). The influenza RNPs consist of the negative-sense viral RNAs (vRNAs) encapsidated by the viral nucleoprotein, and the viral polymerase complex, which is formed by the PA, PB1 and PB2 proteins. The RNA polymerase complex catalyzes three different reactions: synthesis of an mRNA with a 5' cap and 3' polyA structure essential for translation by the host translation machinery; a full length complementary RNA (cRNA), and of genomic vRNAs using the cRNAs as a template. Newly synthesized vRNAs, NP and, PB1, PB2 and PA polymerase proteins are then assembled into new RNPs, for further replication or encapsidation and release of progeny virus particles. Therefore, to produce influenza virus using a reverse genetics system, all 8 vRNAs and mRNAs that express the viral proteins (NP, PB1, PB1 and PA) essential for replication must be synthesized. The expression vector of the invention may be utilized to produce all of these vRNAs and mRNAs.

The expression vector may also be utilized to produce any serotype of influenza A virus without departing from the scope of the invention. Influenza A viruses are classified into serotypes based upon the antibody response to the viral surface proteins hemagglutinin (HA or H) encoded by the HA vRNA segment, and neuraminidase (NA or N) encoded by the NA vRNA segment. At least sixteen H subtypes (or serotypes) and nine N subtypes of influenza A virus have been identified. New influenza viruses are constantly being produced by mutation or by reassortment of the 8 vRNA segments when more than one influenza virus infects a single host. By way of example, known influenza serotypes may include H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7 serotypes.

A. Vector

The expression vector of the invention comprises a vector. As used in reference to the eight unit viral vector, "vector" refers to an autonomously replicating nucleic acid unit. The present invention can be practiced with any known type of vector, including viral, cosmid, phasmid, and plasmid vectors. The most preferred type of vector is a plasmid vector. As is well known in the art, plasmids and other vectors may possess a wide array of promoters, multiple cloning sequences, and transcription terminators.

The vector may have a high copy number, an intermediate copy number, or a low copy number. The copy number may be utilized to control the expression level for the transcription cassettes, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori. In an alternative embodiment, a low copy number vector may be utilized. For example, a low copy number vector may have one or at least two, three, four, five, six, seven, eight, nine, or ten copies per bacterial cell. A non-limiting example of low copy number vector may be a vector comprising the pSC101 ori. In an exemplary embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

The vector may further comprise a selectable marker. Generally speaking, a selectable marker encodes a product that the host cell cannot make, such that the cell acquires resistance to a specific compound or is able to survive under specific conditions. For example, the marker may code for an antibiotic resistance factor. Suitable examples of antibiotic resistance markers include, but are not limited to, those coding for proteins that impart resistance to kanamycin, spectomycin, neomycin, geneticin (G418), ampicillin, tetracycline, and chlorampenicol. The selectable marker may code for proteins that confer resistance to herbicides, such as chlorsulfuron or phosphinotricin acetyltransferase. Other appropriate selectable markers include the thymidine kinase (tk) and the adenine phosphoribosyltransferase (apr) genes, which enable selection in tk- and apr-cells, respectively, and the dihydrofloate reductase (dhfr) genes that confer resistance to methotrexate or trimethoprim. In still other cases, the vector might have selectable Asd+, Murk+, AroA+, DadB+, Alr+, AroC+, AroD+, IlvC+ and/or IlvE+ when the expression vector is used in a balanced-lethal or balanced-attenuation vector-host system when present in and delivered by carrier bacteria.

In some embodiments, the vector may also comprise a transcription cassette for expressing non-viral reporter proteins. By way of example, reporter proteins may include a fluorescent protein, luciferase, alkaline phosphatase, beta-galactosidase, beta-lactamase, horseradish peroxidase, and variants thereof.

In some embodiments, the vector may also comprise a DNA nuclear targeting sequence (DTS). A non-limiting example of a DTS may include the SV40 DNA nuclear targeting sequence. In other embodiments, the vector may also comprise an artificial binding site for a transcriptional factor, such as NF-κB and/or AP-2 (SEQ ID NO: 1: GGGGACTTTCCGGGGACTTTCCTCCC CACGCGGGGGACTTTCCGC-CACGGGCGGGGACTTTCCGGGGACTTTCC). Transcription factor NF-κB is found in almost all animal cell types. Salmonella infection stimulates the expression NF-κB rapidly, and binding affinity of N F-κB members to their DNA-binding sites (κB sites) is high and the translocation of NF-κB-DNA complex into the nucleus is rapid (minutes). The plasmid DNA with κB sites allows newly synthesized NF-κB to bind to the plasmid DNA in the cytoplasm and transport it to the nucleus through the protein nuclear import machinery. Depending on their position relative to the trans-gene, the binding sites could also act as transcriptional enhancers that further increase gene expression levels. The SV40 DTS, NF-κB, and AP-2 binding sequence facilitate nuclear import of the plasmid DNA, and this facilitates transcription of genetic sequences on the vector.

B. Transcription Cassettes for vRNAs Expression

The expression vector comprises at least one transcription cassette for vRNA production. Generally speaking, the transcription cassette for vRNA production minimally comprises a PolI promoter operably linked to a viral cDNA linked to a PolI transcription termination sequence. In an exemplary embodiment, the transcription cassette may also include a nuclear targeting sequence. The number of transcription cassettes for vRNA production within the expression vector can and will vary depending on the virus that is produced. For example, the expression vector may comprise two, three, four, five, six, seven, or eight or more transcription cassettes for vRNA production. When the virus that is produced is influenza, the vector typically will comprise four transcription cassettes for vRNA production.

The term "viral cDNA", as used herein, refers to a copy of deoxyribonucleic acid (cDNA) sequence corresponding to a vRNA segment of an RNA virus genome. cDNA copies of viral RNA segments may be derived from vRNAs using standard molecular biology techniques known in the art (see, e.g., Sambrook et al. (1989) "Molecular Cloning: A Laboratory Manual," 2nd Ed., Cold Spring Harbor Laboratory Press, Cold Spring Harbor, and Knipe et al (2006) "Virology", Fifth Edition, Lippincott Williams & Wilkins; edition). In some embodiments, the cDNA may be derived from a naturally occurring virus strain or a virus strain commonly used in vitro. In other embodiments, the cDNA may be derived synthetically by generating the cDNA sequence in vitro using methods known in the art. The natural or synthetic cDNA sequence may further be altered to introduce mutations and sequence changes. By way of example, a naturally occurring viral sequence may be altered to attenuate a virus, to adapt a virus for in vitro culture, or to tag the encoded viral proteins.

The selection of promoter can and will vary. The term "promoter", as used in reference to a viral cassette, may mean a synthetic or naturally derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The promoters may be of viral, prokaryotic, phage or eukaryotic origin. Non-limiting examples of promoters may include T7 promoter, T3 promoter, SP6 promoter, RNA polymerase I promoter and combinations thereof. In some embodiments, the promoters may be different in each transcription cassette. In preferred embodiments, the promoters may be the same in each transcription cassette. In preferred alternatives of this embodiment, the promoters may be RNA polymerase I (Pol I) promoters. In an exemplary alternative of this embodiment, the promoters may be human Pol I promoters. In another exemplary alternative of this embodiment, the promoters may be chicken Pol I promoters.

The promoter may be operably linked to the cDNA to produce a negative-sense vRNA or a positive-sense cRNA. In an exemplary alternative of this embodiment, the promoter may be operably linked to the cDNA to produce a negative-sense vRNA.

The transcription cassette also includes a terminator sequence, which causes transcriptional termination at the end of the viral cDNA sequence. By way of a non-limiting example, terminator sequences suitable for the invention may include a Pol I terminator, the late SV40 polyadenylation signal, the CMV polyadenylation signal, the bovine growth hormone polyadenylation signal, or a synthetic polyadenylation signal. In some embodiments, the terminators may be different in each transcription cassette. In a preferred embodiment, the terminators may be the same in each transcription cassette. In one alternative of this embodiment, the Pol I terminator may be a human Pol I terminator. In an exemplary embodiment, the terminator is a murine Pol I terminator. In an exemplary alternative of this embodiment, the terminator sequence of the expression cassettes may be a truncated version of the murine Pol I terminator.

To function properly during replication, vRNAs transcribed from the transcription cassettes generally have precise 5' and 3' ends that do not comprise an excess of non-virus sequences. Depending on the promoters and terminators used, this may be accomplished by precise fusion to promoters and terminators or, by way of example, the transcription cassette may comprise ribozymes at the ends of transcripts, wherein the ribozymes cleave the transcript in such a way that the sequences of the 5' and 3' termini are generated as found in the vRNA.

As will be appreciated by a skilled artisan, when the expression vector produces influenza virus, the expression vector may comprise at least one transcription cassette for vRNA production. The transcription cassette may be selected from the group consisting of (1) a Pol I promoter operably linked to an influenza virus HA cDNA linked to a Pol I transcription termination sequence; (2) a Pol I promoter operably linked to an influenza virus NA cDNA linked to a Pol I transcription termination sequence; (3) a Pol I promoter operably linked to an influenza virus M cDNA linked to a Pol I transcription termination sequence; and (4) a PolI promoter operably linked to an influenza virus NS cDNA linked to a Pol I transcription termination sequence. The expression vector may comprise at least 2, 3, or 4 of these transcription cassettes. In an exemplary embodiment, the expression vector will also include either one or two different nuclear targeting sequences (e.g., SV40 DTS and an artificial binding sequence for a transcriptional factor such as NF-κB and/or AP-2).

In an exemplary embodiment when the expression vector produces influenza virus, the expression vector will comprise four transcription cassettes for vRNA production. The transcription cassettes for this embodiment will comprise (1) a Pol I promoter operably linked to an influenza virus HA cDNA linked to a Pol I transcription termination sequence; (2) a Pol I promoter operably linked to an influenza virus NA cDNA linked to a Pol I transcription termination sequence; (3) a Pol I promoter operably linked to an influenza virus M cDNA linked to a PolI transcription termination sequence; and (4) a PolI promoter operably linked to an influenza virus NS cDNA linked to a PolI transcription termination sequence. In an exemplary embodiment, the expression vector will also include either one or two different nuclear targeting sequences (e.g., SV40 DTS and an artificial binding sequence for a transcriptional factor such as NF-κB and/or AP-2).

C. Transcription Cassettes for vRNA and mRNA Expression

The expression vector comprises at least one transcription cassette for vRNA and mRNA production. Typically, the transcription cassette for vRNA and mRNA production minimally comprises a Pol I promoter operably linked to a viral cDNA linked to a Pol I transcription termination sequence, and a PolII promoter operably linked to the viral cDNA and a PolII transcription termination sequence. In an exemplary embodiment, the transcription cassette will also include a nuclear targeting sequence. The number of transcription cassettes for vRNA and mRNA production within the expression vector can and will vary depending on the virus that is produced. For example, the expression vector may comprise two, three, four, five, six, seven, or eight or more transcription cassettes for vRNA and mRNA production. When the virus that is produced is influenza, the expression cassette typically may comprise four transcription cassettes for vRNA and mRNA production.

The viral cDNA, Pol I promoter and Pol I terminator suitable for producing vRNA is as described above in section (e) iiB.

For mRNA production, each transcription cassette comprises a Pol II promoter operably linked to cDNA and a Pol II termination sequence. Non-limiting examples of promoters may include the cytomegalovirus (CMV) promoter, Rous sarcoma virus (RSV) promoter, simian virus 40 (SV40) early promoter, ubiquitin C promoter or the elongation factor 1 alpha (EF1α) promoter. In some embodiments, the promoters may be different in each transcription cassette. In preferred embodiments, the promoters may be the same in each transcription cassette. In preferred alternatives of this embodiment, the promoters may be the CMV Pol II promoter.

Each transcription cassette also comprises a Pol II terminator sequence. By way of non-limiting example, terminator sequences suitable for the invention may include the late SV40 polyadenylation signal, the CMV polyadenylation signal, the bovine growth hormone (BGH) polyadenylation signal, or a synthetic polyadenylation signal. In some embodiments, the terminators may be different in each transcription cassette. In a preferred embodiment, the terminators may be the same in each transcription cassette. In an exemplary embodiment, the terminator is a BGH polyadenylation signal. In an exemplary alternative of this embodiment, the terminator sequence of the expression cassettes may be a truncated version of the BGH polyadenylation signal.

To function properly in initiating vRNA replication, mRNAs transcribed from the transcription cassettes may contain signals for proper translation by the host cell translation machinery. Most cellular mRNAs transcribed from a PolII promoter are capped at the 5' end and polyadenylated at the 3' end after transcription to facilitate mRNA translation. However, some cellular mRNAs and many viral mRNAs encode other sequences that facilitate translation of the mRNA in the absence of a 5' cap structure or 3' polyA structure. By way of example, some cellular mRNAs and viral mRNAs may encode an internal ribosomal entry site (IRES), which could functionally replace the 5' cap. By way of another example, some mRNAs and viral mRNAs may encode an RNA structure, such as a pseudoknot, at the 3' end of the mRNA, which could functionally replace the 3' polyA. In an exemplary embodiment, the mRNAs transcribed from the transcription cassettes are capped at the 5' end and polyadenylated at the 3' end.

As will be appreciated by a skilled artisan, when the expression vector produces influenza virus, the expression vector may comprise at least one transcription cassette for vRNA and mRNA production. The transcription cassette may be selected from the group consisting of (1) a PolI promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a PolI transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a Pol II promoter operably linked to the NP cDNA and a Pol II transcription termination sequence. The expression vector may comprise at least 2, 3, or 4 of these transcription cassettes. In an exemplary embodiment, the expression vector will also include either one or two different nuclear targeting sequences (e.g., SV40 DTS or an artificial binding sequence for a transcriptional factor such as NF-κB and/or AP-2).

In an exemplary embodiment when the expression vector produces influenza virus, the expression vector will comprise four transcription cassettes for vRNA and mRNA production. The transcription cassettes for this embodiment will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a Pol I transcription termination sequence and a PolII promoter operably linked to the NP cDNA and a Pol II transcription termination sequence. In an exemplary embodiment, each expression plasmid construct will also include either one or two different nuclear translocation signals (e.g., SV40 DTS or an artificial binding sequence for a transcriptional factor such as NF-κB and/or AP-2).

D. Exemplary Expression Vectors

In an exemplary iteration of the invention, a single expression vector will comprise all of the genomic segments necessary for the production of influenza virus in a host cell. As detailed above, for the production of influenza virus HA, NA, NS, and M vRNA must be produced and PA, PB1, PB2, and NP vRNA and mRNA must be produced. For this iteration, the expression vector will comprise four transcription cassettes for vRNA production and four transcription cassettes for vRNA and mRNA production. The four cassettes for vRNA production will comprise (1) a Pol I promoter operably linked to an influenza virus HA cDNA linked to a Pol I transcription termination sequence; (2) a Pol I promoter operably linked to an influenza virus NA cDNA linked to a PolI transcription termination sequence; (3) a Pol I promoter operably linked to an influenza virus M cDNA linked to a Pol I transcription termination sequence; and (4) a Pol I promoter operably linked to an influenza virus NS cDNA linked to a PolI transcription termination sequence. The four transcription cassettes for vRNA and mRNA production will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a PolII transcription termination sequence; and (4) a Pol I promoter operably linked to an influenza virus NP cDNA linked to a Pol I transcription termination sequence and a Pol II promoter operably linked to the NP cDNA and a PolII transcription termination sequence. The expression vector will preferably also include either one or two different nuclear translocation signals (e.g., SV40 DTS or an artificial binding sequence for a transcriptional factor such as NF-κB and/or AP-2). In an exemplary embodiment, the vector is a plasmid. The plasmid will generally be a low or intermediate copy number plasmid.

The arrangement and direction of transcription cassettes within the single expression vector relative to each other can and will vary without departing from the scope of the invention. It is believed, however, without being bound by any particular theory that arrangement of transcription cassettes in pairs of vRNA cassettes and vRNA and mRNA cassettes is preferable because it may reduce the degree of recombination and as a result, yield an expression vector with increased genetic stability.

It is also envisioned that in certain embodiments, influenza genomic segments may be produced from more than a single expression vector without departing from the scope of the invention. The genomic segments may be produced, for example, from 2, 3, or 4 or more different expression vectors. In an iteration of this embodiment, NS, and M vRNA, and PA, PB1, PB2, and NP vRNA and mRNA are produced from a single expression vector. For this iteration, the expression vector will comprise two transcription cassettes for vRNA production and four transcription cassettes for vRNA and mRNA production. The two transcription cassettes for vRNA production will comprise (1) a PolI promoter operably linked to an influenza virus M cDNA linked to a Pol I transcription termination sequence; and (2) a Pol I promoter operably linked to an influenza virus NS cDNA linked to a Pol I transcription termination sequence. The four transcription cassettes for vRNA and mRNA production will comprise (1) a Pol I promoter operably linked to an influenza virus PA cDNA linked to a Pol I transcription termination sequence and a Pol II promoter operably linked to the PA cDNA and a Pol II transcription termination sequence; (2) a Pol I promoter operably linked to an influenza virus PB1 cDNA linked to a Pol I transcription termination sequence and a Pol II promoter operably linked to the PB1 cDNA and a Pol II transcription termination sequence; (3) a Pol I promoter operably linked to an influenza virus PB2 cDNA linked to a Pol I transcription termination sequence and a Pol II promoter operably linked to the PB2 cDNA and a Pol II transcription termination sequence; and (4) a Pol I promoter operably linked to an influenza virus NP cDNA linked to a PolI transcription termination sequence and a Pol II promoter operably linked to the NP cDNA and a Pol II transcription termination sequence. The expression of HA vRNA and NA vRNA may be from a single expression vector that comprises two transcription cassettes comprising (1) a PolI promoter operably linked to an influenza virus HA cDNA linked to a PolI transcription termination sequence; and (2) a PolI promoter operably linked to an influenza virus NA cDNA linked to a Pol I transcription termination sequence. Alternatively, expression of HA vRNA and NA vRNA may be from two separate expression vectors.

In some embodiments, restriction digestion sites may be placed at convenient locations in the expression vector. By way of example, restriction enzyme sites placed at the extremities of the cDNAs may be used to facilitate replacement of cDNA segments to produce a desired reassortment or strain of the virus. By way of another example, restriction enzyme sites placed at the extremities of the transcription cassettes may be used to facilitate replacement of transcription cassettes to produce a desired reassortment or strain of the virus. Suitable, endonuclease restriction sites include sites that are recognized by restriction enzymes that cleave double-stranded nucleic acid. By way of non-limiting example, these sites may include AarI, AccI, AgeI, Apa, BamHI, BglI, BglII, BsiWI, BssHI, BstBI, ClaI, CviQI, DdeI, DpnI, DraI, EagI, EcoRI, EcoRV, FseI, FspI, HaeII, HaeIII, HhaI, HincII, HindIII, HpaI, HpaII, KpnI, KspI, MboI, MfeI, NaeI, NarI, NcoI, NdeI, NgoMIV, NheI, NotI, PacI, PhoI, PmlI, PstI, PvuI, PvuII, SacI, SacII, SalI, SblI, SmaI, SpeI, SphI, SrfI, StuI, TaqI, TfiI, TliI, XbaI, XhoI, XmaI, XmnI, and ZraI. In an exemplary alternative of this embodiment, the restriction enzyme site may be AarI.

iii. Nucleic Acid Vaccine Vector

A recombinant bacterium of the invention may encompass a nucleic acid vaccine vector. Such a vector is typically designed to be transcribed in the nucleus of the host cell to produce mRNA encoding one or more antigens of interest. To increase performance, a nucleic acid vaccine vector should be targeted to the nucleus of a host cell, and should be resistant to nuclease attack.

In one embodiment of the invention, a nucleic acid vaccine vector may be targeted to the nucleus using a DNA nuclear targeting sequence. Such a sequence allows transcription factors of the host cell to bind to the vector in the cytoplasm and escort it to the nucleus via the nuclear localization signal-mediated machinery. DNA nuclear targeting sequences are known in the art. For instance, the SV40 enhancer may be used. In particular, a single copy of a 72-bp element of the SV40 enhancer may be used, or a variation thereof. The SV40 enhancer may be used in combination with the CMV immediate-early gene enhancer/promoter.

Additionally, DNA binding sites for eukaryotic transcription factors may be included in the vaccine vector. These sites allow transcription factors such as NF-κB and AP-2 to bind to the vector, allowing the nuclear location signal to mediate import of the vector to the nucleus.

A nucleic acid vaccine vector of the invention may also be resistant to eukaryotic nuclease attack. In particular, the polyadenalytion signal may be modified to increase resistance to nuclease attack. Suitable polyadenylation signals that are resistanct to nuclease attack are known in the art. For instance, the SV40 late poly A signal may be used. Alternatively, other poly A adenylation signal sequences could be derived from other DNA viruses known to be successful in infecting avian and/or mammalian species.

A bacterium comprising a nucleic acid vaccine vector may also comprise a mutation that eliminates the periplasmic endonuclease I enzyme, such as a ΔendA mutation. This type of mutation is designed to increase vector survival upon the vector's release into the host cell.

(f) Attenuation

In each of the above embodiments, a recombinant bacterium of the invention may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gastrointestinal tract (in the case of *Salmonella*) and induce immune responses is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of lymphoid tissues before the recombinant bacterium is regulated to display the attenuated phenotype.

In one embodiment, a recombinant bacterium may be attenuated by regulating LPS O-antigen. In other embodiments, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asdA, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asdA. Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

Other means of attenuation are known in the art.

i. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be necessary to synthesize a component of the cell wall of the bacterium, or may itself be a necessary component of the cell wall such as the protein encoded by murA. In still other embodiments, the protein may be listed in Section i above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid sequence encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta$araBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as $\Delta$araBAD23, which prevents use of arabinose retained in the cell cytoplasm at the time of oral immunization, and/or $\Delta$araE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in section (e).

In some embodiments, more than one modification may be performed to optimize the attenuation of the bacterium.

For instance, at least one, two, three, four, five, six, seven, eight or nine modifications may be performed to optimize the attenuation of the bacterium. In various exemplary embodiments of the invention, the SD sequences and/or the start codons for the fur and/or the phoPQ virulence nucleic acid sequences may be altered so that the production levels of these nucleic acid products are optimal for regulated attenuation.

(g) Other Mutations

A bacterium may further comprise additional mutations. Such mutations may include the regulation of serotype-specific antigens, those detailed below.

i. Regulated Expression of a Nucleic Acid Sequence Encoding at Least One Serotype-Specific Antigen Generally speaking, a recombinant bacterium of the invention is capable of the regulated expression of a nucleic acid sequence encoding at least one serotype-specific antigen. As used herein, the phrase "serotype-specific antigen" refers to an antigen that elicits an immune response specific for the bacterial vector serotype. In some embodiments, the immune response to a serotype-specific antigen may also recognize closely related strains in the same serogroup, but in a different, but related, serotype. Non-limiting examples of serotype-specific antigens may include LPS O-antigen, one or more components of a flagellum, and Vi capsular antigen. In some embodiments, the expression of at least one, at least two, at least three, or at least four nucleic acid sequences encoding a serotype-specific antigen are regulated in a bacterium of the invention.

The phrase "regulated expression of a nucleic acid encoding at least one serotype-specific antigen" refers to expression of the nucleic acid sequence encoding a serotype-antigen such that the bacterium does not substantially induce an immune response specific to the bacterial vector serotype. In one embodiment, the expression of the serotype-specific antigen is eliminated. In another embodiment, the expression is substantially reduced. In yet another embodiment, the expression of the serotype-specific antigen is reduced in a temporally controlled manner. For instance, the expression of the serotype-specific antigen may be reduced during growth of the bacterium in a host, but not during in vitro growth.

The expression of a nucleic acid sequence encoding a *Salmonella* serotype-specific antigen may be measured using standard molecular biology and protein and carbohydrate chemistry techniques known to one of skill in the art. As used herein, "substantial reduction" of the expression of a nucleic acid sequence encoding a serotype-specific antigen refers to a reduction of at least about 1% to at least about 99.9% as compared to a *Salmonella* bacterium in which no attempts have been made to reduce serotype-specific antigen expression. In one embodiment, the expression of a nucleic acid sequence encoding a serotype-specific antigen is reduced by 100% by using a deletion mutation. In other embodiments of the invention, the expression of a nucleic acid sequence encoding a serotype-specific antigen is reduced by at least about 99.9%, 99.5%, 99%, 98%, 97%, 96%, 95%, 94%, 93%, 92%, 91% or 90%. In yet other embodiments of the invention, the expression of a nucleic acid sequence encoding a serotype-specific antigen is reduced by at least about 89%, 88%, 87%, 86%, 85%, 84%, 83%, 82%, 81% or 80%. In still other embodiments of the invention, the expression of a nucleic acid sequence encoding a serotype-specific antigen is reduced by at least about 75%, 70%, 65%, 60%, 55%, or 50%. In additional embodiments, the expression of a nucleic acid sequence encoding a serotype-specific antigen is reduced by at least about 45%, 40%, 35%, 30%, 25%, or 20%. In yet additional embodiments, the expression of a nucleic acid sequence encoding a serotype-specific antigen is reduced by at least about 15%, 10%, 5%, 4%, 3%, 2% or 1%.

Methods of regulating expression of a nucleic acid sequence encoding at least one serotype-specific antigen are discussed in detail below, and in the examples.

A. Regulating the Expression of a Nucleic Acid Sequence Encoding LPS O-Antigen

In one embodiment, the expression of a nucleic acid sequence encoding the serotype-specific antigen LPS O-antigen is regulated by mutating the pmi nucleic acid sequence, which encodes a phosphomannose isomerase needed for the bacterium to interconvert fructose-6-P and mannose-6-P. In some instances, the bacterium comprises a Δpmi mutation, such as a Δpmi-2426 mutation. A bacterium comprising a Δpmi-2426 mutation, grown in the presence of mannose, is capable of synthesizing a complete LPS O-antigen. But non-phosphorylated mannose, which is the form required for bacterial uptake, is unavailable in vivo. Hence, a bacterium comprising a Δpmi-2426 mutation loses the ability to synthesize LPS O-antigen serotype specific side chains after a few generations of growth in vivo. The LPS that is synthesized comprises a core structure that is substantially similar across many diverse *Salmonella* serotypes. This results in a bacterium that is capable of eliciting an immune response against at least two *Salmonella* serotypes without substantially inducing an immune response specific to the serotype of the bacterial vector.

A bacterium of the invention that comprises a Δpmi mutation may also comprise other mutations that ensure that mannose available to the bacterium during in vitro growth is used for LPS O-antigen synthesis. For instance, a bacterium may comprise a Δ(gmd-fcl)-26 mutation. This mutation deletes two nucleic acid sequences that encode enzymes for conversion of GDP-mannose to GDP-fucose. This ensures that mannose available to the bacterium during in vitro growth is used for LPS O-antigen synthesis and not colanic acid production. Similarly, a bacterium may comprise the Δ(wcaM-wza)-8 mutation, which deletes all 19 nucleic acid sequences necessary for colanic acid production, and also precludes conversion of GDP-mannose to GDP-fucose.

In addition to regulating LPS O-antigen synthesis with mannose, the synthesis of LPS O-antigen may be regulated by arabinose, which is also absent in vivo. For instance, a bacterium may comprise the mutation $\Delta P_{rfc}$::TT araC $P_{BAD}$ rfc. (P stands for promoter and TT stands for transcription terminator.) The rfc nucleic acid sequence is necessary for the addition of O-antigen subunits, which typically comprise three or four sugars, in a repeat fashion. When the rfc nucleic acid sequence is absent, only one O-antigen repeat subunit is added to the LPS core polysaccharide. Normally, the serotype-specific O-antigen contains some 50 or so repeats of the O-antigen subunit, catalyzed by the enzyme encoded by the rfc nucleic acid sequence. In the case of a bacterium comprising the $\Delta P_{rfc}$::TT araC $P_{BAD}$ rfc deletion-insertion mutation, expression of the rfc nucleic acid sequence is dependant on the presence of arabinose that can be supplied during in vitro growth of the strain, but that is absent in vivo. Consequently, rfc expression ceases in vivo, resulting in the cessation of assembly of the O-antigen repeat structure. This reduces the bacterium's ability to induce an immune response against the serotype-specific O-antigen.

Another means to regulate LPS O-antigen expression is to eliminate the function of galE in a recombinant bacterium of the invention. The galE nucleic acid sequence encodes an enzyme for the synthesis of UDP-Gal, which is a substrate for LPS O-antigen, the outer LPS core and colanic acid. Growth of a bacterium comprising a suitable galE mutation in the presence of galactose leads to the synthesis of O-antigen and the LPS core. Non-phosphorylated galactose is unavailable in vivo, however, and in vivo synthesis of UDP-Gal ceases, as does synthesis of the O-antigen and the LPS outer core. One example of a suitable galE mutation is the Δ(galE-ybhC)-851 mutation.

In certain embodiments, a bacterium of the invention may comprise one or more of the Δpmi, $\Delta P_{rfc}$::TT araC $P_{BAD}$ rfc, and ΔgalE mutations, with or without a Δ(gmd-fcl)-26 or Δ(wcaM-wza)-8 mutation. Such a combination may yield a recombinant bacterium that synthesizes all components of the LPS core and O-antigen side chains when grown in vitro (i.e. in the presence of suitable concentrations of mannose, arabinose and galactose), but that ceases to synthesize the LPS outer core and O-antigen in vivo due to the unavailability of free unphosphorylated mannose, arabinose or galactose. Also, a recombinant bacterium with the inability to synthesize the LPS outer core and/or O-antigen is attenuated, as the bacterium is more susceptible to killing by macrophages and/or complement-mediated cytotoxicity. Additionally, a bacterium with the inability to synthesize the LPS outer core and O-antigen in vivo, induces only a minimal immune response to the serotype-specific LPS O-antigen.

The regulated expression of one or more nucleic acids that enable synthesis of LPS O-antigen allows a recombinant bacterium of the invention to be supplied with required sugars such as mannose, arabinose and/or galactose during in vitro growth of the bacterium, ensuring complete synthesis of the LPS O-antigen. This is important, because the presence of the O-antigen on the recombinant bacterium cell surface is indispensable for the strain to invade and colonize lymphoid tissue, a necessary prerequisite for being immunogenic. In vivo, LPS O-antigen synthesis ceases due to the unavailability of the free unphosphorylated sugars. Consequently, the recombinant bacterium is attenuated, becoming more susceptible to complement-mediated cytotoxicity and macrophage phagocytosis. Also, when LPS O-antigen synthesis ceases, the LPS core is exposed. The core is a cross-reactive antigen with a similar structure in all *Salmonella* serotypes. In addition, when LPS O-antigen synthesis ceases, any cross-reactive outer membrane proteins expressed by the recombinant bacterium are exposed for surveillance by the host immune system.

B. The Expression of a Nucleic Acid Sequence Encoding a Component of a Flagellum In one embodiment, the expression of a nucleic acid encoding a serotype-specific component of a flagellum is regulated by mutating the nucleic acid that encodes FljB or FliC. For instance, a bacterium of the invention may comprise a ΔfljB217 mutation. Alternatively, a bacterium may comprise a ΔfliCI80 mutation. The ΔfljB217 mutation deletes the structural nucleic acid sequence that encodes the Phase II flagellar antigen whereas the ΔfliCI80 mutation deletes the 180 amino acids encoding the antigenically variable serotype-specific domain of the Phase I FliC flagellar antigen. The portion of the flagellar protein that interacts with TLR5 to recruit/stimulate innate immune responses represents the conserved N and C-terminal regions of the flagellar proteins and this is retained and expressed by strains with the ΔfliCI80 mutation. In addition, the ΔfliCI80 mutation retains the CD4-dependent T-cell epitope. It should be noted, that expression of the Phase I flagellar antigen and not the Phase II flagellar antigen potentiates *S. Typhimurium* infection of mice. *S. Typhimurium* recombinant bacteria with the Δpmi-2426, ΔfljB2I7 and ΔfliC180 mutations, when grown in the absence of mannose, are not agglutinated with antisera specific for the B-group O-antigen or the *S. Typhimurium* specific anti-flagellar sera. These recombinant bacteria are also non-motile since the FliC180 protein that is synthesized at high levels is not efficiently incorporated into flagella. When these recombinant bacteria are evaluated using HEK293 cells specifically expressing TLR5, the level of NF-κB production is about 50% higher than when using a ΔfliB217 F1iC+ strain that assembles flagellin into flagella and exhibits motility (there is no NF-κB production by the control ΔfljB217 ΔfliC2426 strain with no flagella). Similarly, recombinant bacteria with the Δ(galE-ybhC)-851, ΔfljB217 and ΔfliC180 mutations, when grown in the absence of galactose, are not agglutinated with antisera specific for the B-group O-antigen or the *S. Typhimurium* specific anti-flagellar sera. These bacteria are also non-motile.

In some embodiments, a bacterium may comprise both a ΔfljB217 and a ΔfliC2426 mutation. Such a bacterium will typically not synthesize flagella, and hence, will not be motile. This precludes interaction with TLR5 and up-regulation of NF-κB production. Such a bacterium will reduce bacterial-induced host programmed cell death.

C. The Expression of a Nucleic Acid Sequence Encoding the Vi Capsular Antigen

Certain *Salmonella* strains, such as *S. Typhi* and *S. Dublin*, express the Vi capsular antigen. This antigen is serotype-specific, inhibits invasion, and acts to suppress induction of a protective immune response. Consequently, when a recombinant bacterium of the invention is derived from a strain comprising the Vi capsular antigen, one or more nucleic acids encoding the Vi capsular antigen will be deleted such that the Vi capsular antigen is not synthesized. Even though synthesis and display of the Vi capsular antigen on the *Salmonella* cell surface interferes with invasion and suppresses induction of immunity, the purified Vi antigen can be used as a vaccine to induce protective immunity against infection by Vi antigen displaying *S. Typhi* and *S. Dublin* strains.

ii. Eliciting an Immune Response Against at Least Two *Salmonella* Serotypes

A recombinant bacterium of the invention may be capable of eliciting an immune response against at least two *Salmonella* serotypes. This may be accomplished, for instance, by eliminating the serotype-specific LPS O-antigen side chains as discussed above. The remaining LPS core will elicit an immune response, inducing the production of antibodies against the LPS core. Since this LPS core is substantially identical in the several thousand *Salmonella enterica* serotypes, the antibodies potentially provide immunity against several diverse *Salmonella enterica* serotypes, such as Typhimurium, Heidelberg, Newport, Infantis, Dublin, Virchow, Typhi, Enteritidis, Berta, Seftenberg, Ohio, Agona, Braenderup, Hadar, Kentucky, Thompson, Montevideo, Mbandaka, Javiana, Oranienburg, Anatum, Paratyphi A, Schwarzengrund, Saintpaul, and Munchen.

In addition, the elimination of the LPS O-antigen provides the host immune system with better access to the outer membrane proteins of the recombinant bacterium, thereby enhancing induction of immune responses against these outer membrane proteins. In some embodiments, as described below, the outer membrane proteins may be upregulated to further enhance host immune responses to these proteins. Non-limiting examples of outer membrane proteins include proteins involved in iron and manganese uptake, as described below. Iron and manganese are essential nutrients for enteric pathogens and the induction of antibodies that inhibit iron and manganese uptake in effect starves the pathogens, conferring protective immunity on the host. Additionally, since these proteins are homologous among the enteric bacteria, such host immune responses provide immunity against multiple *Salmonella enterica* serotypes as well as to other enteric bacterial pathogens such as strains of *Yersinia, Shigella* and *Escherichia*. As evidence of this, the attenuated *S. Typhimurium* vaccine vector strain not expressing any *Yersinia* antigen is able to induce significant protective immunity to high doses of orally administered *Y. pseudotuberculosis*.

The elicited immune response may include, but is not limited to, an innate immune response, a mucosal immune response, a humoral immune response and a cell-mediated immune response. In one embodiment, Th2-dependent mucosal and systemic antibody responses to the enteric antigen(s) are observed. Immune responses may be measured by standard immunological assays known to one of skill in the art. In an exemplary embodiment, the immune response is protective.

iii. Reduction in Fluid Secretion

In some embodiments, a recombinant bacterium of the invention may be modified so as to reduce fluid secretion in the host. For instance, the bacterium may comprise the ΔsopB1925 mutation. Alternatively, the bacterium may comprise the ΔmsbB48 mutation. In another alternative, the bacterium may comprise both the ΔsopB1925 mutation and the ΔmsbB48 mutation iv. Biological Containment Under certain embodiments, a live recombinant bacterium may possess the potential to survive and multiply if excreted from a host. This leads to the possibility that individuals not electing to be immunized may be exposed to the recombinant bacterium. Consequently, in certain embodiments, a recombinant bacterium of the invention may comprise one or more mutations that decrease, if not preclude, the ability of *Salmonella* vaccines to persist in the GI tract of animals.

In another embodiment, a recombinant bacterium of the invention may comprise one or more of the Δ(gmd fcl)-26 or Δ(wcaM-wza)-7, ΔagfBAC811, Δ($P_{agfD}$ agfG)-4, Δ(agfC-agfG)-999, ΔbcsABZC2118 or ΔbcsEFG2319 and Δ(yshA-yihW)-157 mutations that block synthesis of colanic acid, thin aggregative fimbriae (i.e., curli), cellulose and extracellular polysaccharide, respectively, all of which contribute to biofilm formation. In addition, the mutation ΔyhiR36 that prevents use of DNA as a nutrient, Δ(shdA-ratB)-64, ΔmisL2 and ΔbigA3 that encode four proteins that enable *Salmonella* to adhere to host extracellular matrix proteins and ΔackA233 that blocks use of acetate, may be used as a means for biological containment. Likewise, inclusion of mutations that block use of the sugars fucose and ribose such as ΔfucOR8 and Δrbs-19 will reduce ability of vaccine strains to persist in the intestinal tract. In exemplary embodiments, a recombinant bacterium comprising a biological containment mutation is not adversely affected in its virulence.

In some embodiments, the recombinant bacterium may comprise a method of regulated delayed lysis in vivo that prevents bacterial persistence in vivo and survival if excreted. These chromosomal mutations may include: Δ(gmd fcl)-26 or Δ(wcaM-wza)-8 that precludes synthesis of colanic acid that can protect cells undergoing cell wall-less death from lysing completely, ΔagfBAC811 that blocks synthesis of thin aggregative fimbriae (curli) that are critical for biofilm formation to enable persistent colonization on bile stones in the gall bladder, ΔasdA27::TT araC $P_{BAD}$ c2 insertion-deletion mutation to impose a requirement for the peptidoglycan constituent DAP and Δ$P_{murA12}$::TTaraC $P_{BAD}$ murA or the improved Δ$P_{murA25}$::TTaraC $P_{BAD}$ murA insertion-deletion mutation as a conditional-lethal mutation blocking synthesis of the peptidoglycan constituent muramic acid. The latter two mutations are typically complemented by a regulated delayed lysis plasmid vector such as pYA3681 or the improved pYA4763 that has an arabinose-dependent expression of asdA and murA genes. A recombinant bacterium comprising such mutations grows normally in the presence of arabinose. In vivo, however, the bacterium ceases to express any nucleic acids encoding the Asd and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring biological containment.

In some embodiments, a recombinant bacterium may comprise a mutation that blocks the recycling of cell wall peptidoglycan to ensure lysis occurs. For instance, a bacterium may comprise an ampG mutation, an ampD mutation or a nagE mutation, or two or three of these mutations.

v. Crp Cassette

In some embodiments, a recombinant bacterium of the invention may also comprise a Δ$P_{crp}$::TT araC $P_{BAD}$ crp deletion-insertion mutation. Since the araC $P_{BAD}$ cassette is dependent both on the presence of arabinose and the binding of the catabolite repressor protein Crp, a Δ$P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated or constructed that synthesize a Crp protein that is not dependent on cAMP to regulate transcription from $P_{BAD}$. Two such alterations in the crp gene have been made with amino acid substitution mutations T127I, Q170K and L195R to result in the crp-70 gene modification and with amino acid substitutions I112L, T127I and A144T to result in the crp-72 gene modification. Both constructions have been made with araC $P_{BAD}$ to yield the Δ$_{crp70}$::TT araC $P_{BAD}$ crp-70 and Δ$P_{crp72}$::TT araC $P_{BAD}$ crp-72 deletion-insertion mutations. In both cases, synthesis of the Crp protein induced by arabinose is insensitive to the addition of glucose. This strategy may also be used in other systems responsive to Crp, such as the systems responsive to rhamnose and xylose described above.

(h) Exemplary Bacterium

In an exemplary embodiment, a bacterium may comprise one or more mutations to increase invasiveness (section (a) above), one or more mutations to allow endosomal escape (section (b) above), one or more mutations to reduce bacterium-induced host programmed cell death (section (c)

above), one or more mutations to induce lysis of the bacterium (section (d) above), one or more mutations to express a nucleic acid encoding an antigen (section (e) above), one or more mutations to attenuate the bacterium (section (f) above), and one or more mutations to enhace the performance of the bacterium as a vaccine (section (g) above).

II. Vaccine Compositions and Administration

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by Paul, W E, Stites D et. al. and Ogra PL. et. al. Mucosal immunity is also described by Ogra PL et. al.

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention In still another embodiment, a recombinant bacterium of the invention may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Construction of S. Typhimurium Vaccine Strains with Regulated Delayed In Vivo Lysis after Colonization of Effector Lymphoid Tissues in Order to Release Antigens In Vivo and Confer Complete Biological Containment We have developed a system after much effort that is dependant on the presence of arabinose for viability. The *S. Typhimurium* strain has mutations that preclude synthesis of diaminopimelic acid (DAP) (an unique essential constituent of the peptidoglycan layer of the cell wall) and make synthesis of muramic acid (another unique constituent of peptidoglycan) dependent on the presence of arabinose. In the absence of DAP and arabinose, cells undergo cell wall-less death and lyse. These two mutations are complemented by a plasmid vector that has the asdA and murA genes necessary for synthesis of DAP and muramic acid, respectively, with expression of these genes dependant on a tightly regulated araC $P_{BAD}$ activator-promoter cassette and the presence of arabinose. Expression of the asdA and murA genes is turned off by both absence of arabinose and activation of a promoter that synthesizes anti-sense asdA and murA mRNA to block translation of residual asdA and murA mRNAs. The strain also possesses a deletion mutation to eliminate synthesis of the colanic acid capsule that is capable of protecting cells with defective cell walls from lysing, a relA mutation that dissociates continuation of growth from a dependence on continued protein synthesis (to result in complete lysis) and two mutations that alter arabinose uptake, retention and utilization. The later mutation precludes deleterious acidification of growth media by metabolism of arabinose.

When this host-vector is used to orally immunize mice, the bacteria attach to the GALT, invade and by growth colonize the mesenteric lymph node and spleen. With each cell division the amounts of the Asd and MurA enzymes decrease by half and ultimately become insufficient to maintain cell wall synthesis resulting in cell lysis with release of cell contents. We have constructed $Asd^+$ $MurA^+$ regulated lysis plasmid vectors with pSC101 ori, p15A ori, pBR ori and pUC ori such that the regulated delayed lysis vaccine strains will undergo varying numbers of cell divisions from few to many, respectively, in vivo prior to lysis. Since lysis liberates lipid A, which is an endotoxin, we have engineered strains to synthesize the mono-phosphoryl lipid A, which is non toxic and yet serves as an adjuvant agonist of both murine and human TLR4. The regulated delayed lysis vectors have also been constructed with the LacI regulatable promoter $P_{trc}$ and we have inserted genes for various protective antigens with or without sequences encoding one of a diversity of type 2 secretion systems (T2SS) that can export antigen out of vaccine cells prior to lysis with liberation of a bolus of antigen. When using this system, we include a ΔrelA::TT araC $P_{BAD}$ lacI TT deletion-insertion mutation so that growth of the strain in the presence of arabinose causes synthesis of LacI to initially repress synthesis of protein antigens encoded by sequences under the control of $P_{trc}$. As a consequence of cell division in vivo during colonization of lymphoid tissues, LacI becomes diluted and expression of $P_{trc}$ controlled genes commences with synthesis of the protective antigen to stimulate induction of immune responses. In all cases the regulated delayed lysis phenotype is totally attenuating with no persistence of vaccine cells in vivo and no survival of vaccine cells if excreted. This regulated delayed lysis system has been described by Kong et al. (2008. Regulated programmed lysis of recombinant *Salmonella* in host tissues to release protective antigens and confer biological containment. Proc. Natl. Acad. Sci. USA 105:9361-9366) and Curtiss and Kong (US Patent 2006/0140975).

Example 2

Delivery of Woodchuck Hepatitis Core Particle Influenza M2e Fusion by Recombinant Attenuated *Salmonella* Vaccine (RASV) with Regulated Delayed Attenuation and Regulated Delayed Lysis Phenotypes The highly conserved ectodomain of the influenza M2 protein (M2e) has been shown to provide broad-spectrum protection against multiple influenza subtypes. With the recent emergence of influenza A subtypes like H5N1 that are capable of causing human disease, it becomes imperative to design a vaccine that induces cross protective immunity.

Thus, we incorporated the highly immunogenic conserved M2e epitopes from both human and avian influenza into the core antigen of woodchuck hepatitis virus (WHcAg). We also did comparative studies using the less manipulatable HBV core and delivered the WHV and WHV core-M2e fusions on pBR ori and pUC ori vectors from *Salmonella* vaccine strains with and without regulated delayed lysis. Strains with regulated delayed lysis and employing pUC ori lysis vectors induced the highest antibody titers (log 2 14 to 16), but were not totally protective in mice challenged with high doses of influenza virus. However, with low dose challenges there was survival to challenge with a modest lessening of weight loss after challenge. Thus, delivery of the human and avian M2e antigens will contribute to a modest level of protection that should be influenza strain non-specific but will be insufficient and thus inadequate as a stand-alone vaccine. Our results are thus similar to results obtained by others.

Figure 1:
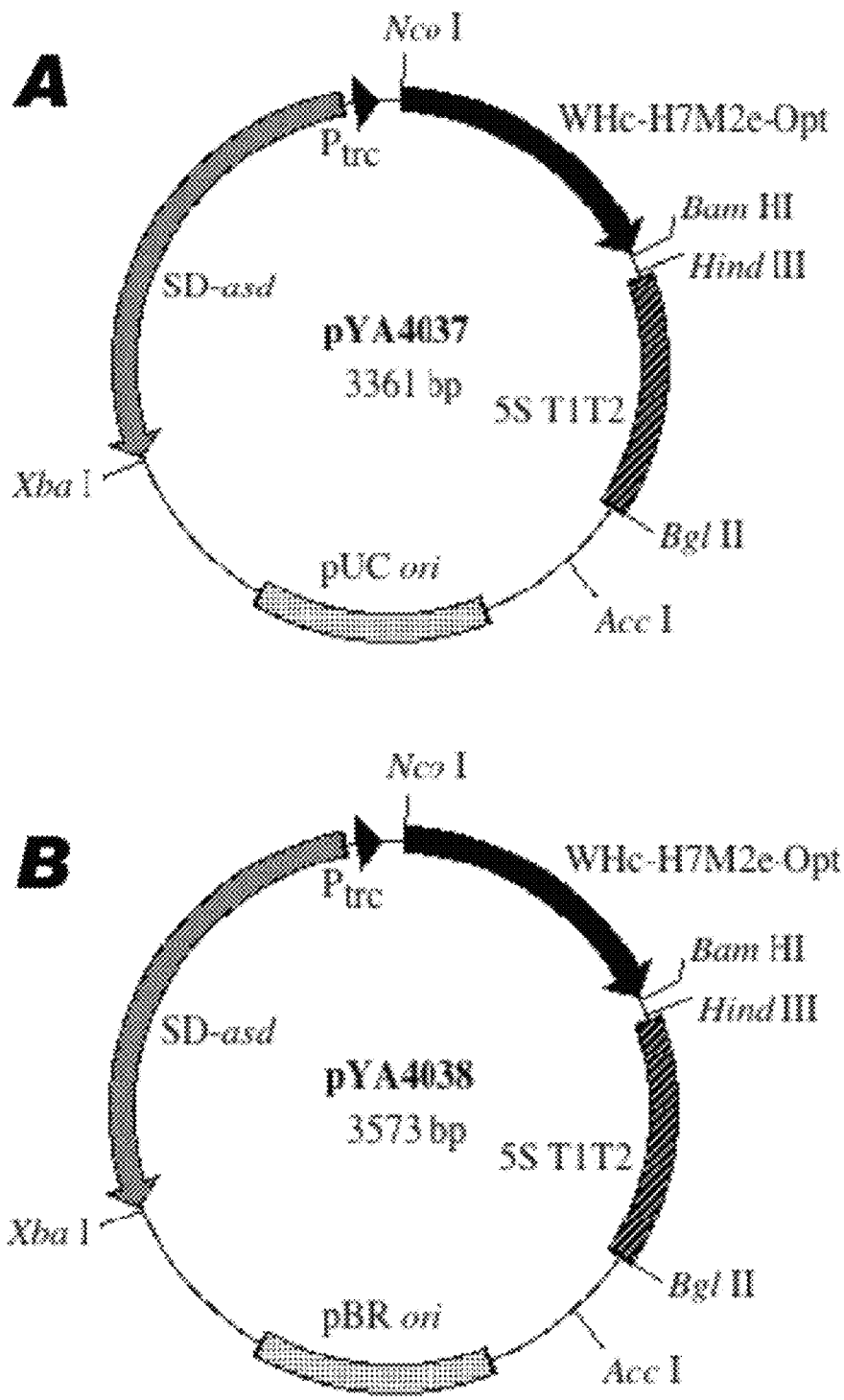
FIG. 1 depicts plasmid maps of (A) pYA4037, (B) pYA4038, and (C) pYA3664. The 569 bp WHc-H7M2e-opt fusion fragment flanked by NcoI and BamHI on either sides is in control of the $P_{trc}$-5S T1T2 promoter-terminator unit in Asd+ vectors pYA4037 and pYA4038 and in control of $P22P_R$-5S T1T2 promoter-terminator unit in pYA3664 to finally yield a ~20 kDa fusion protein.
Figure 1C:
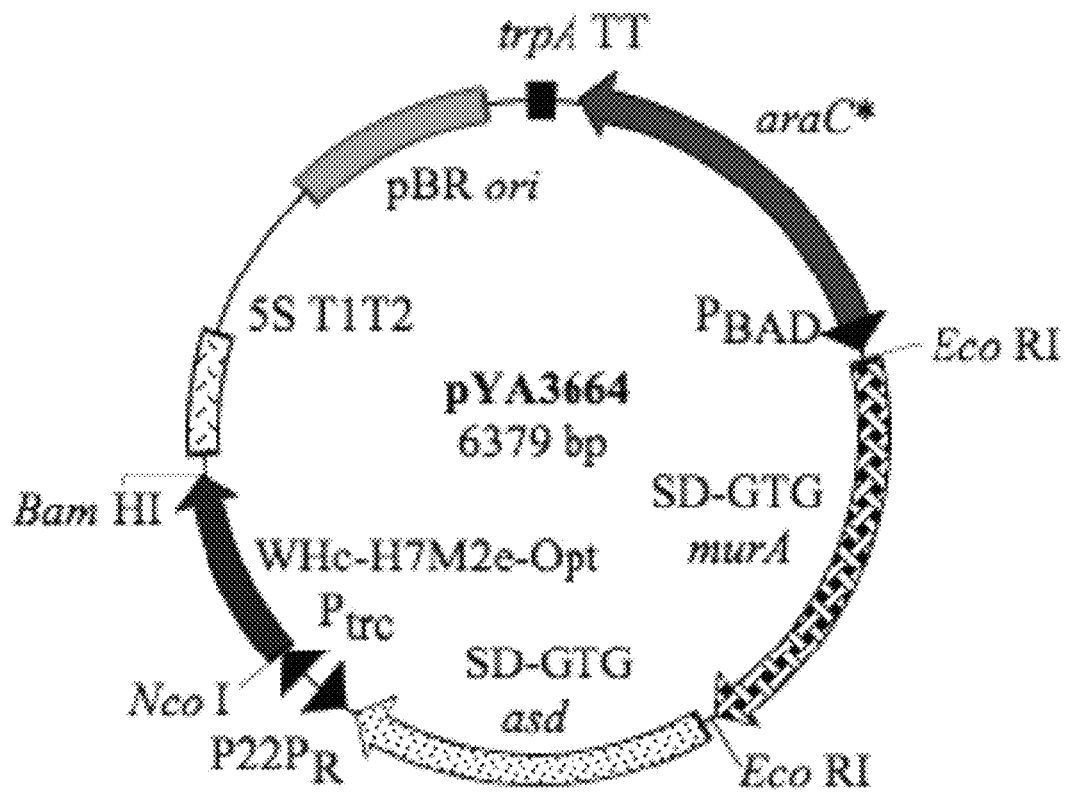

To construct RASVs, the codon optimized WHc-M2e fusion construct (569 bp) was individually ligated into three vectors in order to determine optimal expression conditions. The gene encoding the fusion protein was cloned into the Asd$^+$ expression vectors pYA3341 (pUC ori), pYA3342 (pBR ori) and the lysis vector pYA3681 (pBR ori) to yield plasmids pYA4037, pYA4038 and pYA3664, respectively (FIG. 1). Plasmids were transformed into appropriate *S. Typhimurium* strains to yield χ8025(pYA4037), χ8025 (pYA4038), and χ8888(pYA3664).

To investigate the immunogenicity of the WHc-M2e fusions delivered by RASV, we compared the immunogenicity of strains χ8025(pYA4037) and χ8888(pYA3664) in mice orally immunized on days 1 and 21. Serum IgG responses to M2e, the woodchuck hepatitis virus core particle and purified *S. Typhimurium* LPS were measured by ELISA. All of the vaccinated groups had significantly (P<0.01) higher anti-M2e titers than mice immunized with the vector control strain χ8025(pYA3342) and BSG control mice. Mice immunized with strain χ8888(pYA3664) achieved significantly higher anti-M2e titers than those immunized with χ8025(pYA4037) at all three time points (P<0.01) (FIG. 2A).

Figure 2:
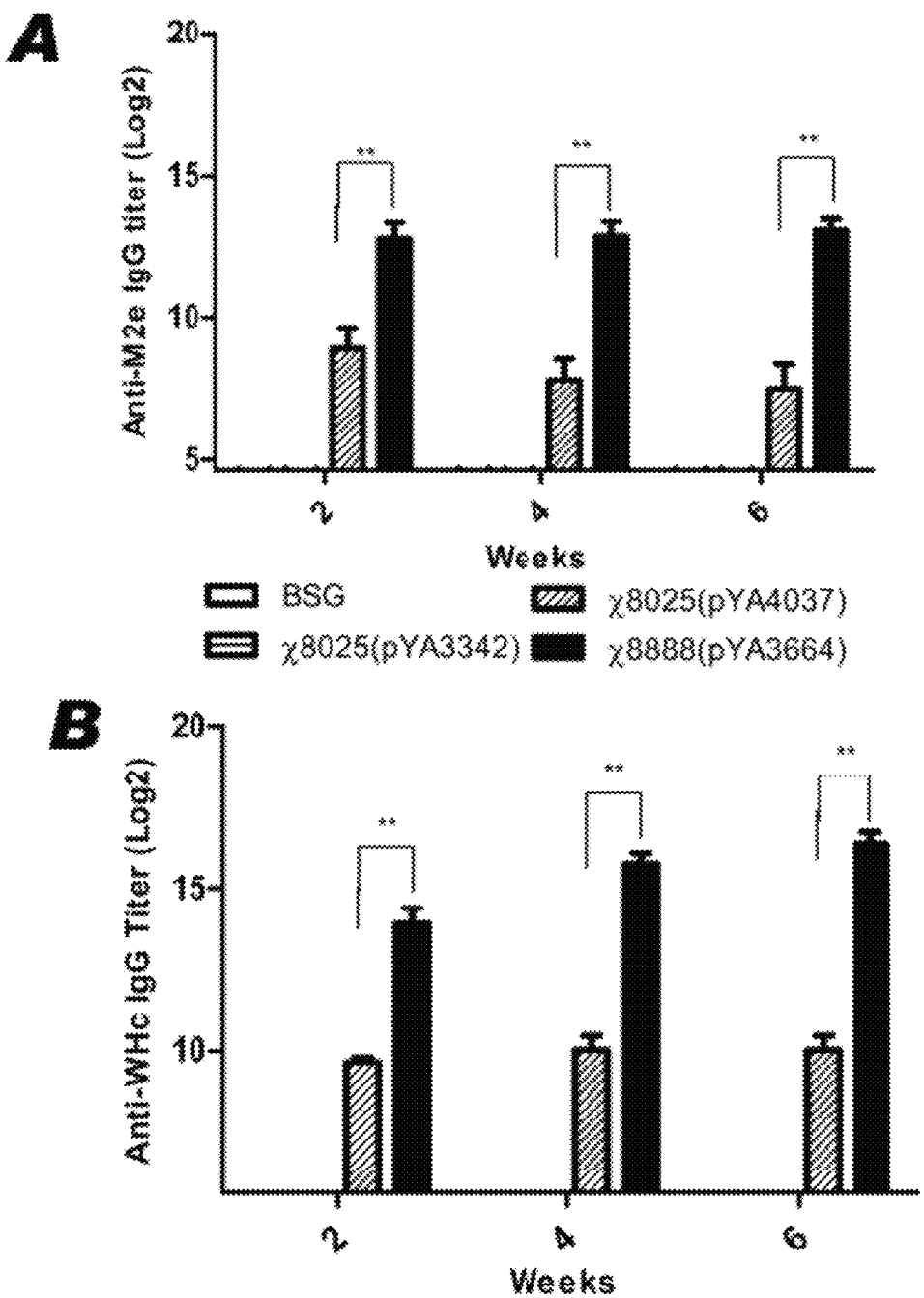
FIG. 2 depicts graphs of the induction of IgG to (A) M2e peptide, (B) woodchuck hepatitis core and (C) purified *Salmonella Typhimurium* LPS after oral immunization of mice with recombinant attenuated *Salmonella* expressing WHc-M2e cores. Data presented here are representative data of two independent experiments and are the geometric mean±SE of 10 mice. ** P<0.01
Figure 2C:
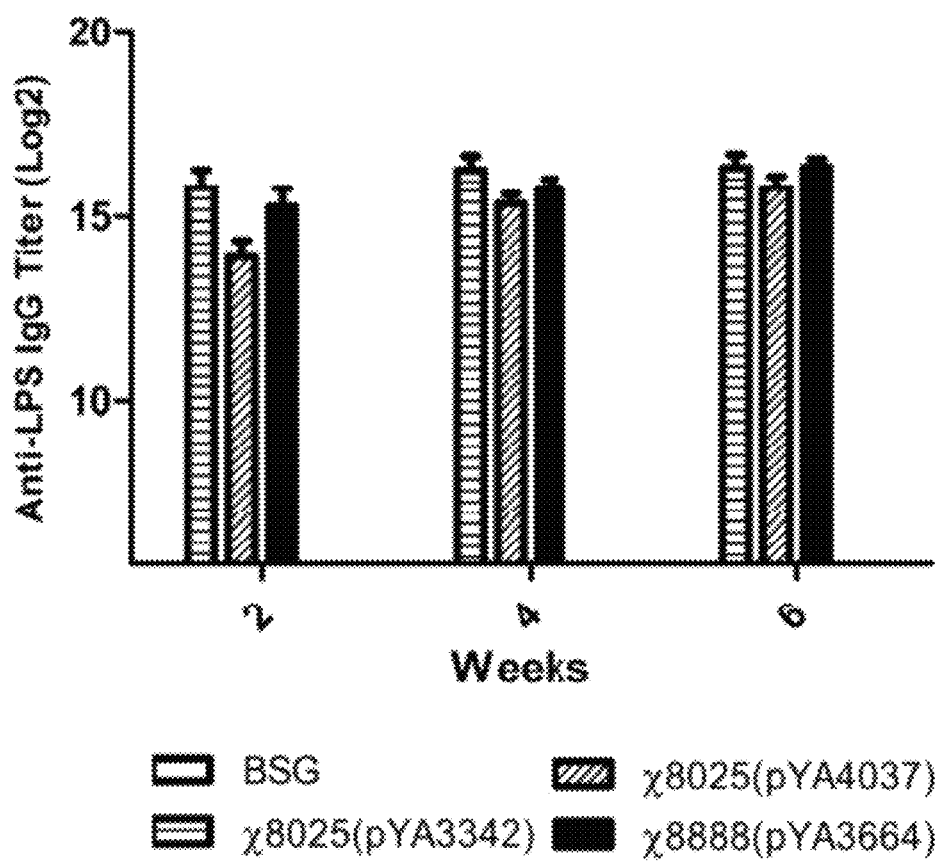

Similar results were seen with regards to the antibody response to WHc particles (FIG. 2B). All of the vaccinated groups had significantly (P<0.01) higher titers than mice immunized with the vector control strain χ8025(pYA3342) and BSG control mice. Mice immunized with strain χ8888 (pYA3664) achieved higher anti-WHc titers than those immunized with χ8025(pYA4037) at all three time points (P<0.01). In contrast, LPS titers did not significantly differ between any *Salmonella* vaccinated group (FIG. 2C) (P>0.05). These results indicate that the WHc-M2e fusion protein delivered by strain χ8888 exhibiting regulated delayed lysis in vivo induced higher antibody titers in mice than when delivered by the non-lysing strain χ8025. Additionally, since the anti-LPS IgG responses in all groups, including the vector control, were not significantly different this difference is most likely due to more efficient delivery of the antigen rather than a difference in fitness between the strains.

Figure 3:
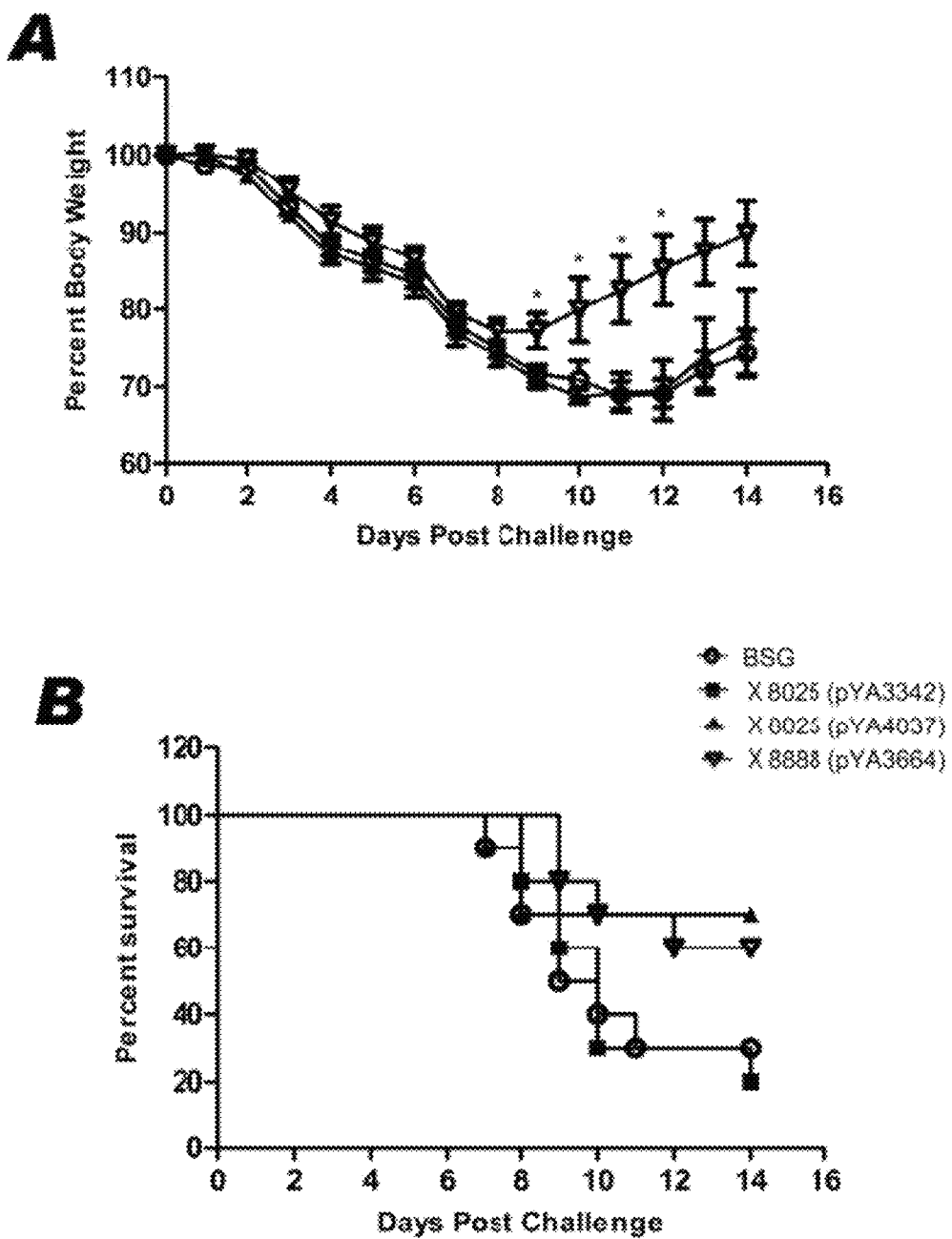
FIG. 3 depicts graphs of the weight loss after challenge of immunized mice with (A) 1×10³ $TCID_{50}$ of rWSN M2 avian virus, and (B) Mortality curve after challenge with 1×10⁴ $TCID_{50}$ rWSN M2 avian virus. * P<0.05. Data presented here are mean±SE of 10 mice.

To determine whether the RASV delivered WHc-M2e fusions provided protection against influenza, we challenged immunized mice with either 1×10$^3$ or 1×10$^4$ TCID$_{50}$ of rWSN M2 avian. At the low dose challenge we observed weight loss in all groups through day 8 post-infection. On days 8 through 12 the groups vaccinated with χ8888 (pYA3664) had significantly higher (P>0.05) average weight than the other groups, signifying an earlier recovery from infection than the BSG control, vector control or χ8025(pYA4037) groups (FIG. 3A). At the high challenge dose we observed no difference in average weight throughout the 14 days period and the survival rates were 70% and 60% for χ8025(pYA4037) and χ8888(pYA3664), respectively (FIG. 3B). The BSG and vector control groups had survival rates of 30% and 20% respectively (FIG. 3B). In summary, lower dose groups receiving χ8888(pYA3664) had a more rapid recovery in body weight compared to both χ8025(pYA4037) and the controls, whereas at a higher dose groups receiving either vaccine had a relatively higher rate of survival as compared to the controls. We also systematically made constructs for WHV core delivery of M2e and NS1 epitopes. We have completed fusions of the C-terminal portion of influenza virus NS1 epitopes from A/Udorn/72 (H3N2) with the Woodchuck hepatitis virus (WHV) core either alone at the spike; or with the M2e at the spike and NS1 at the C-terminus in derivatives of the Asd$^+$ vectors pYA3342 (pBR ori) and pYA3681 (pBR ori with arabinose controlled murA and asd genes for a delayed lysis phenotype) with both codon optimization and non optimized configuration. Insertion of NS1 epitope at the spike of codon optimized and non-optimized WHC in pYA3342 resulted in pYA4447 and pYA4448, while the non-codon optimized construct in pYA3681 created pYA4496. Insertion of NS1 at the C-terminus with M2e at the spike of codon-optimized and non-codon optimized WHC in pYA3342 gave pYA4444 and pYA4445, while the non-codon optimized construct in pYA3681 gave pYA4448. The vector control, pYA4469, was constructed by eliminating the M2e sequence from pYA4058 and re-ligating. Each of these vectors were tested for monomer formation by SDS-PAGE and western blots, core formation by electron microscopy and plasmid stability for over 50 generations. The newer *Salmonella* strains mentioned previously, χ9505 (Δpmi Δ(gmd-fcl) ΔP$_{fur}$::TT araC P$_{BAD}$ fur ΔP$_{crp}$::TT araC P$_{BAD}$ crp ΔasdA::TT araC P$_{BAD}$ c2 ΔaraE ΔaraBAD ΔrelA::araC P$_{BAD}$ lacI TT ΔendA) and lysis strain χ9447 (Δpmi Δ(gmd-fcl) ΔP$_{fur}$::TT araC P$_{BAD}$ fur ΔP$_{crp}$::TT araC P$_{BAD}$ crp ΔasdA::TT araC P$_{BAD}$ c2 ΔaraE ΔaraBAD ΔrelA::araC P$_{BAD}$ lacI TT ΔP$_{murA}$::TT araC P$_{BAD}$ murA ΔendA) were assessed for their abilities to invade into human intestinal epithelial cells (Int-407), and were used to immunize mice with the above derivatives of pYA3342 and pYA3681. Blood drawn at the 4$^{th}$ and 6$^{th}$ weeks post vaccination was tested for the presence of antibodies against NS1, M2e, WHC and LPS. Mice were challenged with 10$^6$ TCID$_{50}$ of the A/Udorn/72 strain of influenza virus 7 weeks post vaccination. The results indicated that mice immunized with the C-terminus of the NS1 peptide are capable of conferring protection against weight loss after viral challenge. This means that the NS1 epitope is a promising candidate for inclusion in our final vaccine construction.

Example 3

Construction of *S. Typhimurium* Vaccine Strains with the Regulated Delayed Lysis Phenotype to Release DNA Vaccine Vectors Encoding Influenza HA and NA Antigens Another initial objective was to develop the regulated delayed lysis vector system to deliver to the cytosol a DNA vaccine encoding influenza HA and NA antigens that would be synthesized by the immunized animal host. It was this objective that motivated most of our effort to develop the regulated delayed lysis system. Initially, we construct a DNA vaccine vector with all the attributes of the regulated delayed lysis vector described above but possessing a CMV promoter to enable expression of cloned genes encoding protective HA and NA antigens in eukaryotic cells. Although modest results were obtained in inducing antibodies to influenza antigens, we soon realized the necessity to make more substantial improvements in the vector system. We have further improved our DNA vaccine vector by using a repeated DNA nuclear targeting sequence/enhancer (from SV40) and observed rapid import of the vector into the host nucleus as measured by the expression of a GFP reporter. We then added recognition sequences for the binding of transcriptional factors, such as NF-κB and AP-2, and improved the plasmid stability by replacing the nuclease sensitive poly adenylation encoding sequence with one from a DNA virus selected during evolution to withstand activities of host DNases. All these changes significantly improved expression when the DNA vaccine vector with a GFP reporter was used to transfect several different avian, murine and human cell lines in culture. The resulting DNA vaccine vector thus has the regulated delayed lysis multi-component cassette (having the same elements described above), the optimized eukaryotic expression system (in place of the bacterial expression system) and a high-copy number pUC ori. The resulting DNA vaccine vector pYA4545 has been engineered to specify synthesis of several different influenza HA antigens from avian (H3, H5 and H7) and mammalian (H1 and H3) influenza viruses. These have been constructed with and without C-terminal SopE fusions to hopefully facilitate ubiquination and targeting to the proteosome for MHC class I presentation.

Example 4

Delivery of a Eight-Unit One-Plasmid Expression System by an Engineered Salmonella Vaccine Strain with a Regulated Delayed Lysis System to Enable Synthesis of Influenza Virus in Eukaryotic Cells and in Immunized Animals As part of our ongoing attempts to develop a DNA vaccine against influenza virus, we constructed a novel eight-unit single plasmid system that expresses all the viral RNAs and internal proteins to generate influenza virus in cultured cells. An obvious application of this technology, if successful, would be to deliver the expression plasmid using a Salmonella bacterium with all the attributes discussed above for DNA vaccine delivery into host cells of an immunized animal host. Upon successful colonization followed by invasion of cells within the host, the recombinant Salmonella strain would undergo programmed regulated delayed lysis releasing the cytoplasmic contents along with the expression plasmid construct into the cytosol. We identified three essential factors that needed to be considered to achieve our goal: a) expression of virus from a minimal number of plasmid constructs, b) a suitable recombinant attenuated Salmonella strain that would invade the host lymphoid tissue and also delay apoptosis/pyroptosis events to enable plasmid delivery in the cytosol, and c) successful entry of the plasmid construct into the host cell nucleus for transcription of viral cDNA. We have now developed a more comprehensive expression-plasmid system to generate influenza virus. We used influenza A/WSN/1 virus in our studies. By use of reverse genetics in conjunction with a dual promoter system, we constructed a 23.61 kb plasmid (pYA4519) with a p15A ori. The plasmid is designed to transcribe vRNA from cDNA fragments of M, NS, NA, NP, PA, PB2, PB1, NP and HA of influenza virus, each under the control of the PolI unit (chicken polymerase I promoter and murine terminator) and mRNA of the viral polyermase complex (PA, PB1, PB2) as well as the nucleoprotein (NP), each under the control of the PolII unit (cytomegalovirus promoter and bovine growth hormone poly-adenylation sequence). The polymerase complex and the nucleoprotein associate with the vRNAs to form the ribonucleoproteins (RNPs) that are minimal critical units for the transcription and replication of vRNAs. As a means to measure viral cDNA expression from the plasmid we used a reporter gene (mcherry), and confirmed successful expression of mcherry upon transfection of the plasmid into cultured chicken embryo fibroblasts (CEFs). We improved the nuclear import efficiency of the eight-unit plasmid by adding the promoter/enhancer region of simian virus 40 (SV40) and NF-κB binding sequence. These improved plasmid constructs were delivered into a co-culture of CEFs and MDCK using the carrier S. Typhimurium χ9834 (ΔasdA-33 Δalr-3 ΔdadB4 ΔrecA62, a genotype that leads to cell wall-less lysis) and successful influenza virus generation was observed by measuring hemagglutination and by quantitating virus production from the cell cultures. These data indicated that our novel eight-unit single plasmid expression system to generate influenza virus was successful and with the current knowledge available in employing the right Salmonella strains for DNA vaccine delivery, we are confident of developing a vaccine to immunize chickens against influenza infection.

Our plasmid construct can facilitate the design of a much simpler approach to develop influenza vaccine seeds using a "1+2" approach (as opposed to the currently used "2+6" approach), where the first plasmid (such as pYA4562 with deletion of HA and NA cassettes) provides the 6 segments of influenza viral genome from either the high productive strain PR8 (A/PR/8/34) or the cold-adapted strain (e.g. A/AA/6/60) and the other two plasmids provide HA and NA elements of the epidemic strain. Alternatively, the HA and NA segments of the model virus strain can be replaced with those of the epidemic strain (in our expression vector) to generate influenza virus from a single plasmid. We validated this expectation by constructing a plasmid (derivative of our improved pYA4562 vector) encoding an attenuated virus. We chose the influenza A virus (A/chicken/TX/167280-4/02(H5N3)) for this purpose. This virus is an isolate from White Leghorns chickens and belongs to a low pathogenic avian influenza virus. The viral HA segment Tx02HA) shares homology with low pathogenic virus and hence makes an ideal challenge strain. Based on these considerations, a Tx02HA expression cassette CPI-Tx02HA-MTI was constructed to replace the WSN HA cassette in pYA4519 to obtain plasmid pYA4693. Delivery of this plasmid into the host (by an appropriate bacterial carrier) yielded an avian influenza virus of low pathogenicity suitable for immunization of poultry. This reconstruction with substitution of the HA gene only took one week. In other applications, the sequence encoding the influenza virus can be modified to attenuate the strain's ability to cause disease symptoms without eliminating or adversely altering its immunogenicity, such that the immunized bird (animal) develops protective immunity against influenza virus. For more details, see Zhang, X., W. Kong, S. Ashraf, R. Curtiss III. 2009. A "one-plasmid" system to generate influenza virus in cultured chicken cells for potential use in influenza vaccine. J. Virol. 83:9296-9303.

Example 5

Improvements in Balanced-Lethal Host-Vector Systems

To eliminate use of plasmid vectors with non-permitted drug resistance genes and to stabilize plasmid vectors in RASV strains in vivo, we developed a balanced-lethal host-vector system. This balanced-lethal host-vector system is based on the structure of peptidoglycan, which makes up the rigid layer of the bacterial cell wall. Peptidoglycan consists of a crystal lattice structure made up of the two amino-sugars N-acetylglucosamine (GlcNAc) and N-acetylmuramic acid (MurNAc). MurNAc is cross-linked via the four amino acids L- and D-alanine, D-glutamic acid and mesodiaminopimelic acid (DAP). The asdA gene encodes aspartyl semi-aldehyde dehydrogenase which is essential in the conversion of L-aspartate to DAP. Without this gene and its product the structure fails to crosslink and falls apart resulting in lysis of the bacterial cell. We have deleted the asdA gene in our strains and inserted it into our vectors. This makes our vaccine strains absolutely dependent upon the presence of a vector containing the wild-type asd gene and serves to maintain the vector inside the host strain. Since overexpression of this gene, which results from expressing it on a high copy number plasmid such as those with a pUC origin of replication (ori), also attenuates the strain we modified the Shine-Dalgarno (SD) sequence for lower expression.

Example 6

Progress in Achieving Regulated Delayed Attenuation

Pathogenic bacteria may be attenuated by mutation so that upon infection, host disease symptomology is not elicited. Most means of attenuation, however, make live vaccine strains more suceptible than wild-type strains to environmental stresses encountered after inoculation into the animal or human host. Consequently, fewer bacteria survive to colonize the GALT, NALT and/or BALT with a reduction in effective immunogenicity of the vaccine. Thus these attenuation mechanisms hyperattenuate the vaccine, precluding the candidate vaccine from either reaching or persisting in lymphoid tissues to a sufficient extent or duration to permit induction of a protective immune response against the wild-type pathogen of interest. Thus in attenuating bacteria, particularly enteric bacteria, one must balance the bacteria's ability to survive in very stressful environments and invade the Gut Associated Lymphoid Tissue (GALT) with its ability to cause disease in the host. We have therefore developed two means to achieve a regulated delayed attenuation phenotype so that vaccine strains, at the time of immunization, exhibit nearly wild-type attributes for survival and colonization of lymphoid tissues and after five to ten cell divisions become avirulent. The first strategy makes use of pmi mutants that lack the phosphomannose isomerase needed to interconvert fructose-6-P and mannose-6-P. Therefore strains with the Δpmi mutation grown in the presence of mannose synthesize a complete LPS O-antigen but lose LPS O-antigen side chains after about seven generations of growth in medium devoid of mannose or in tissues since non-phosphorylated mannose, required for uptake to synthesize O-antigen, is unavailable. To ensure that all mannose provided to the vaccine during growth prior to immunization is directed at LPS O-antigen synthesis as well as prevent colonic acid production, we include the Δ(gmd-fcl) mutation that deletes two genes that encode enzymes for conversion of GDP-mannose to GDP-fucose and thus prevents synthesis of colanic acid that could protect lysing bacteria from death. This mutation does not alter the attenuation, tissue-colonizing ability or immunogenicity of a strain with the Δpmi mutation alone. RASV strains with the Δpmi mutation induce higher antibody titers to the expressed protective antigen than to LPS. Our second strategy uses a system for regulated delayed lysis in vivo that provides a means for both attenuation and biological containment. For more details, see Curtiss, R. III., X. Zhang, S. Y. Wanda, H. Y. Kang, V. Konjufca, Y. Li, B. Gunn, S. Wang, G. Scarpellini, and I. S. Lee. 2007. Induction of host immune responses using *Salmonella*-vectored vaccines, p. 297-313 In K. A. Brogden, F. C. Minion, N. Cornick, T. B. Stanton, Q. Zhang, L. K. Nolan, and M. J. Wannemuehler (eds.). Virulence Mechanisms of Bacterial Pathogens, 4$^{th}$ ed., ASM Press, Washington, D.C.; and Curtiss, R. III, S. Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect. Immun. 77:1071-1082.

Example 7

Figure 4:
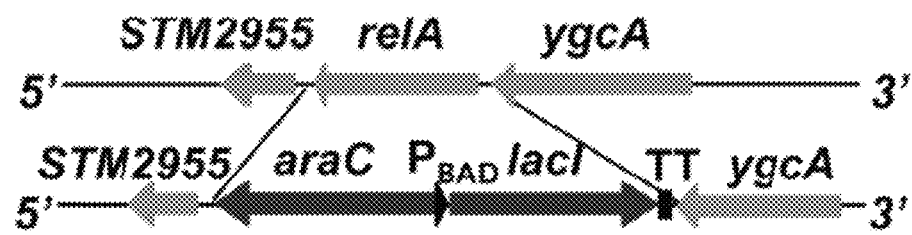
FIG. 4 depicts an illustration of chromosomal deletion-insertion mutations. (A) deletion of 2247 bp (relA-12 to relA-2235) and inserted 2429 bp of araC $P_{BAD}$ lacI. (B)
Figure 4:
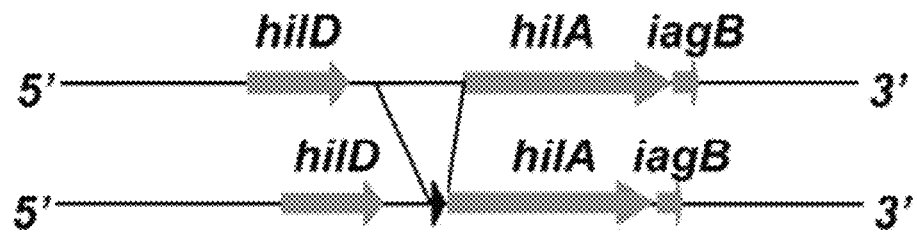

Construction of RASV Strains to Exhibit Regulated Delayed Synthesis of Cloned Genes Over-synthesis of protective antigens, which may be necessary to induce protective immunity to diverse enteric pathogens by RASV strains, can reduce colonizing ability and thus immunogenicity. It was for this and other reasons that Chatfield et al. proposed the use of the nirB promoter that is more active anaerobically than aerobically in accord with a more likely in vivo anaerobic environment (e.g. lower intestine). The $P_{trc}$ promoter that we have used in our lysis system is constitutive under most environments but is more transcriptionally active both anaerobically and aerobically than the nirB promoter. To enable controlled expression by the LacI regulatable $P_{trc}$, we generated the optimized ΔrelA:: araC $P_{BAD}$ lacI TT insertion-deletion mutation (FIG. 4A) (P stands for promoter, TT stands for transcriptional terminator. The cloning of a sequence encoding a protective antigen under $P_{trc}$ control enables the regulated delayed antigen synthesis to facilitate vaccine strain colonization since growth of the vaccine strain in LB broth with 0.2% arabinose causes synthesis of LacI due to the ΔrelA::araC $P_{BAD}$ lacI TT deletion-insertion mutation. This technology has been improved to increase expression of the lacI gene 40-fold by changing the SD sequence from AGGG to AGGA, the lacI start codon from GTG to ATG and by changing lacI codons to maximize translation efficiency in *Salmonella*. No antigen burden effect was seen in mice immunized with the vaccine strains that includes a regulated delayed antigen synthesis system, and those vaccine strains induce greater antibody response to the synthesized protective antigen. For more details, see Curtiss, R. III., W. Xin, Y. Li, W. Kong, S. Y. Wanda, B. M. Gunn, and S. Wang. 2010. New technologies in using recombinant attenuated *Salmonella* vaccine vectors. Crit. Rev. Immunol. 30:255-270.

Two other attributes of the regulated delayed lysis strain have been improved by additional genetic modifications. First, we wanted to improve the efficiency with which the strain invaded into a diversity of cells within an immunized individual. Two solutions have been accomplished. We discovered and recently reported that the leucine binding protein Lrp is a repressor of the hilA gene and other *Salmonella* pathogenicity island 1 (SPI-1) genes encoding the invasion phenotype discovered by Galan and Curtiss 20 years ago. Deletion of the lrp gene thus causes an elevated constitutive expression of invasion genes and significantly enhances the induction of hightened immune responses most noticeable sooner after oral immunization than seen when using isogenic Lrp$^+$ strains. The second means has been to construct and evaluate strains in which we replaced the hilA gene promoter with a modified P$_{trc}$ promoter in which we deleted the sequence recognized by the LacI repressor as described further below. This was necessary since we over express an arabinose regulated lacI gene during growth of vaccine strains to give the regulated delayed protective antigen synthesis phenotype that enhances effective colonization of lymphoid tissues. The *S. Typhimurium* strain χ9971 carrying this mutation for constitutive expression of hilA was able to invade and replicate in human intestinal Int-407 cells and colonize in mouse tissues in significantly greater numbers than the wild-type strain.

The second strain improvement was due to the fact that invasive *Salmonella* induce pyroptosis/apoptosis in a fraction of infected macrophages, and is described in Example 9 below.

Example 8

Construction of Hyper-Invasive Strains for Efficient Delivery of Protective Antigens, DNA Vaccine Vector, and Eight-Unit One-Plasmid System Two major mechanisms of bacterial uptake in the gut have been described. In the first, microfold (M) cells in the gut serve to transport fluids, nutrients and bacteria, including pathogens, such as *Salmonella*, that have learned to exploit this cell type. The second mechanism is mediated by dendritic cells scattered throughout the intestinal epithelium that snatch bacteria from the lumen by extending their dendrites into it. The expression of genes required for invasion of M cells is tightly regulated by environmental conditions and a variety of regulatory genes. The hilA (hyper-invasion locus) regulator encodes an OmpR/ToxR family transcriptional regulator that activates the expression of invasion genes in response to both environmental and genetic regulatory factors. The regulation of hilA expression is a key point for controlling expression of the invasive phenotype. The known positive regulators of hilA include csrAB, sirAIbarA, pstS, hilCIsirCIsprA, fis, and hilD, and the known negative regulators include pag, Ion, hha, etc. To improve M cell mediated *Salmonella* invasion, we constructed four different versions of hilA promoter region by replacing its native promoter with P$_{trc}$ (which ensures constitutive expression of hilA) or by introducing various mutations in it to alter the level of hilA expression. Firstly, we replaced the hilA promoter with the P$_{trc}$ promoter that lacks the operator lacO sequence to enable constitutive synthesis of HilA even when the lacI gene in the host strain is expressed. This creates a ΔP$_{hilA}$::P$_{trcΔlacO888}$ hilA deletion-insertion mutation. The resulting strain is χ9971. Secondly, the downstream AT track sequence that is recognized by the nucleoid-associated protein H-NS to silence hilA gene expression, was deleted from the hilA gene promoter region of *S. Typhimurium* UK-1 to create ΔP$_{hilA}$::P$_{hilA255}$ hilA deletion-insertion mutation. The resulting strain is χ9973. Third, both upstream and downstream AT track sequences were deleted from the hilA gene promoter region of *S. Typhimurium* UK-1 to create ΔP$_{hilA}$::P$_{hilA256}$ hilA deletion-insertion mutation. The resulting strain is χ9974. The *S. Typhimurium* strains χ9973 and χ9974 colonize in mouse tissues in significantly greater numbers than the wild-type strain when mice are immunized intranasally. The *S. Typhimurium* strain χ9971 (ΔP$_{hilA}$::P$_{trcΔlacO888}$ hilA) (FIG. 4B) was able to invade and replicate in human intestinal Int-407 cells (MOI 50:1) and colonize in mouse tissues in significantly greater numbers than the wild-type strain (FIG. 5 and FIG. 6) when mice are immunized orally. We inserted ΔP$_{hilA}$::P$_{trcΔlacO888}$ hilA deletion-insertion mutation into *S. Typhimurium* vaccine strains displaying regulated delayed lysis phenotype to allow sufficient delivery of protective antigen, DNA vaccine and eight-unit one-plasmid expression system.

Example 9

Reduction of *Salmonella*-Induced Host Cell Pyroptosis/Apoptosis to Increase the Efficiency of a DNA Vaccine Delivered by *Salmonella*

Invasive *Salmonella* has been reported to induce pyroptosis/apoptosis in a fraction of infected macrophages and this is likely to diminish the transcription of a DNA vaccine after trafficking to the nucleus. Macrophage infection by *Salmonella* triggers caspase-1-dependent proinflammatory programmed cell death, a recently recognized process termed pyroptosis, which is distinguished from other forms of cellular demise by its unique mechanism, features and inflammatory outcome. *Salmonella* expressing the SPI-1 T3SS and flagellin rapidly trigger caspase-1-dependent pyroptosis of infected macrophages. Strains harboring mutations in genes encoding the SPI-1 T3SS, including invA, invG, invJ, prgH, sipB, sipC, sipD and spaO are not cytotoxic. Meanwhile, caspase-1-mediated delayed macrophage death requires the SPI-2 T3SS, and mutations in the genes encoding the SPI-2 T3SS, or its regulators, render *Salmonella* unable to stimulate delayed cell death. SseL, a *Salmonella* deubiquitinase, is required for *Salmonella*-induced cytotoxicity of macrophages. *Salmonella* sseL mutant strains did not show a replication defect or induce altered levels of cytokine production upon infection of macrophages but were defective for the delayed cytotoxic effect. Another key component in triggering caspase-dependent host cell apoptosis is a large virulence-associated plasmid of *Salmonella*. The tlpA gene encoding a temperature-sensing protein TlpA, like the spy genes in *S. enterica* subspecies I, is located on the virulence plasmid. The tlpA and spvB are two of the most up-regulated genes in *Salmonella*-infected macrophages. A motif present in the tlpA promoter is also found in certain virulence-related genes, both on the virulence plasmid (spvA) and on the chromosome (prgH encoding PrgH and orgA encoding OrgA) of *Salmonella*. Both PrgH and OrgA strongly induce pyroptosis/apoptosis in *Salmonella*-infected macrophage. We therefore deleted the tlpA gene and demonstrated that a strain with this mutation significantly increased ability to invade and replicate in Int-407 cells and colonize mouse tissues in significantly greater numbers than the wild-type strain. Since the *Salmonella*-induced pyroptosis/apoptosis may interfere with the ability of a DNA vaccine to traffic to the nucleus of host cells to be transcribed leading to antigen synthesis and modification in the cytoplasm, we have investigated the means reducing *Salmonella*-induced host cell pyroptosis/apoptosis to determine whether this enhances efficacy of DNA vaccine delivery. Four mutat strains (χ9923: ΔtlpA181; χ9924: ΔsseL116; χ9925: ΔsipB178; and χ9926: ΔspvB177) have been constructed to reduce bacterial-induced apoptosis of the host cell. The S. Typhimurium strains χ9923 (ΔtlpA181) and χ9924 (ΔsseL116) significantly increased the ability of invasion and replication in Int-407 (FIG. 6), and colonized in mouse tissues in significantly greater numbers than the wild-type strain, although they have similar LD$_{50}$ values in comparison with the wild-type strain when mice immunized orally. We constructed S. Typhimurium strains with both ΔtlpA181 and ΔsseL116 mutations. An S. Typhimurium strain with inactivation of the sseL and tlpA genes invades and replicates in cultured cells better than single mutants. We also constructed an S. Typhimurium strain with the constitutive expression of hilA and inactivation of the sseL or tlpA genes. In addition, the S. Typhimurium triple mutant that lacks sseL and tlpA as well as consitutively expresses hilA was also constructed. All these mutations described above were introduced into the lysis system host strains and we are currently evaluating the efficiency of the protective antigen, eight-unit one-plasmid expression system and DNA vaccine delivery by lysis system host strains with those mutations. We will also test other means to reduce/delay pyroptosis/apoptosis such as determining whether using a strain with total absence of flagella enhances vaccine efficacy. Based on these discoveries, we have constructed two sets of S. Typhimurium strains (FIGS. 23A and B) for multiple antigens or/and DNA vaccine delivery. These strains may be applied to develop and evaluate future vaccines.

Example 10

Construction and Evaluation of RASV Strains for Type II or/and Type III Secretion System Delivery of Eimeria Antigens We constructed and evaluated RASV strains to deliver an antigen directly into the cell cytoplasm of the immunized host and into the MHC class I antigen-processing pathway, using the Salmonella type III secretion system (T3SS), for induction of CMI and antigen-specific cytotoxic T-lymphocyte responses in particular. The T3SS, a needle-shaped organelle of Salmonella consisting of over 20 structural or secreted proteins, is critically important during the intestinal phase of infection. The T3SS enables Salmonella to inject its effector proteins into the cytoplasm of the host cell and modulate its cellular functions and signal transduction pathways. To accomplish this goal, Eimeria genes encoding the sporozoite antigen EASZ240 and the merozoite antigen EAMZ250 were fused to the S. Typhimurium effector protein gene sptP in the parental pYA3653 vector, yielding pYA3657 and pYA3658, respectively. Attenuated Salmonella strain χ8879 (ΔphoP ΔsptP::xylE ΔasdA) harboring pYA3657 or pYA3658 were used to orally immunize day-of-hatch chicks and colonization of the bursa, spleen, and liver was observed. In vitro experiments show that the EASZ240 antigen is secreted into the culture supernatant via the T3SS and that it is delivered into the cytoplasm of Int-407 cells by the T3SS. In vivo experiments indicate that both humoral and cell-mediated immune responses were induced in chickens vaccinated with a recombinant attenuated S. Typhimurium vaccine, which led to significant protection against Eimeria challenge. In order to diversify the repertoire of induced immune responses against Eimeria, we also developed RASVs against avian coccidiosis to deliver Eimeria species antigens via the type 3 secretion system (T3SS) and the type 2 secretion system (T2SS) of Salmonella. In contrast to the T3SS, the T2SS has been shown to induce Th1/Th2 immune responses with antibody titers to heterologous antigens that rival the antibody titers to lipopolysaccharide, a Salmonella antigen. For antigen delivery via the T3SS, the E. tenella gene encoding sporozoite antigen SO7 was cloned downstream of the translocation domain of the S. Typhimurium sopE gene in the parental pYA3868 and pYA3870 vectors to generate pYA4156 and pYA4157. These plasmids were introduced into RASV strain χ8879 (ΔphoP ΔsptP::xylE ΔasdA). The vector pYA4184 was constructed for delivery of the SO7 antigen via the T2SS. The SO7 protein was toxic to Salmonella when larger amounts were synthesized; thus, the synthesis of this protein was placed under the control of the LacI repressor, whose synthesis in turn was dependent on the amount of available arabinose in the medium. The pYA4184 vector was introduced into host strain χ9242 (ΔphoP ΔasdA ΔaraBAD ΔrelA::araC P$_{BAD}$ lacI TT (TT is the T4ipIII transcription terminator). In addition to SO7, for immunization and challenge studies we used the EAMZ250 antigen of E. acervulina, which was previously shown to confer partial protection against E. acervulina challenge when it was delivered via the T3SS. Immunization of chickens with a combination of the SO7 and EAMZ250 antigens delivered via the T3SS induced superior protection against E. acervulina challenge. In contrast, chickens immunized with SO7 that was delivered via the T2SS of Salmonella were better protected against E. tenella challenge infection.

Example 11

Host Strain Modification to Enable Immediate or Regulated Delayed Escape from the Endosome Compartment into the Cytosol Salmonella invasion into host cells generally results with the bacterium residing in an endosomal compartment, often termed the Salmonella-containing vacuole. The release of a DNA vaccine due to programmed lysis of a Salmonella cell within this endosome would be unlikely to stimulate a strong immune response due to difficulties that the DNA vaccine molecule would encounter in getting to the nucleus for transcription of the protective antigen-encoding gene. We have solved this problem through the deletion of sifA. The sifA gene encodes a Type III secreted effector protein that governs conversion of the Salmonella-containing vacuoles into filaments and inactivation of sifA leads to escape of Salmonella into the cytosol. We have therefore constructed a ΔsifA mutation that immediately upon invasion into a host cell permits Salmonella to exit the endosome and rapidly multiply in the cytoplasm similar to the way Shigella escapes and then rapidly multiplies in the cytoplasm. We also have the ΔP$_{sifA}$::TT araC P$_{BAD}$ sifA deletion-insertion (FIG. 7), using the same arabinose promoter used previously to replace the original sifA promoter. This mutation enables a regulated delayed escape from the endosome so that lysis occurs in the cytoplasm of cells. We have investigated induction of antibody and antigen-dependent lymphocyte proliferation using delayed regulated lysis S. Typhimurium host strain χ8966 (χ8888 with deletion-insertion mutation ΔP$_{sifA}$::TT araC P$_{BAD}$ sifA) by delivering pYA3674 (pYA3650 encoding an E. acervulina sporozoite antigen) to chickens. Antigen-dependent lymphocyte proliferation was observed after immunization with χ8966 (pYA3674) (FIG. 8).

Example 12

Construction of *S. Typhimurium* Vaccine Strains with Regulated Expression of Genes for the Synthesis of Essential Components of the Peptidoglycan Layer of the Bacterial Cell Wall Enabling Regulated Delayed Lysis after Colonization of Effector Lymphoid Tissues in Order to Release Antigens In Vivo and Confer Complete Biological Containment To eliminate use of plasmid vectors with non-permitted drug resistance genes and to stabilize plasmid vectors in RASVs in vivo, over 20 years ago, we developed a balanced-lethal host-vector system using a vaccine host strain with deletion of the asdA gene to impose an obligate requirement for diaminopimelic acid (DAP) and a plasmid vector with the wild-type asdA gene. Diaminopimelic acid (DAP) and muramic acid are essential components of the peptidoglycan layer of the bacterial cell wall. The asdA gene encodes an enzyme essential for DAP synthesis and the murA gene encodes the first enzyme in muramic acid synthesis. We have devised a regulated lysis system using attenuated *S. Typhimurium* strains that for antigen delivery after colonization of host lymphoid tissues relies on using a more tightly regulated araC $P_{BAD}$ activator-promoter than the original sequence from *E. coli* B/r. This system is composed of two parts. The first component is *S. Typhimurium* strain χ8937 (ΔasdA::TT araC $P_{BAD}$ c2 $\Delta P_{murA}$::TT araC $P_{BAD}$ murA Δ(gmd-fcl) ΔrelA ΔendA) (FIG. 9), with deletions of asdA and arabinose-regulated expression of murA, two genes required for peptidoglycan synthesis and additional mutations to enhance complete lysis and antigen delivery. Unlike lethal asdA deletions, which can be overcome by the addition of DAP to the growth medium, murA deletions, also lethal, cannot be overcome by nutritional supplements. Therefore, a conditional-lethal murA mutation was created by replacing the chromosomal murA promoter with the araC $P_{BAD}$ activator-promoter. Although arabinose is present in plant foods, most is in a complex form such that growth of these strains in media made from chicken feed or mouse food is not possible unless there is supplementation with arabinose. A strain with the $\Delta P_{murA}$::TT araC $P_{BAD}$ murA deletion-insertion mutation undergoes about two cell divisions and then commences to lyse in media made of mouse or chicken feed or chicken breast meat. The Δ(gmd-fcl) mutation deletes genes encoding enzymes for GDP-fucose synthesis, thereby precluding the formation of colanic acid, a polysaccharide made in response to stress associated with cell wall damage. This mutation was included because we have observed that under some conditions, asdA mutants can survive if they produce copious amounts of colanic acid. Therefore, by deleting the genes required for colanic acid synthesis, we circumvent this possibility. The ΔrelA mutation uncouples cell wall-less death from dependence on protein synthesis to further ensure that the bacteria do not survive in vivo or after excretion and to allow for maximum antigen production in the face of amino acid starvation resulting from a lack of aspartate semi-aldehyde synthesis due to the asdA mutation. The second component is plasmid pYA3681 (FIG. 10), which encodes arabinose-regulated murA and asdA expression and C2-regulated synthesis of anti-sense asdA and murA mRNA transcribed from the P22 $P_R$ promoter with opposite polarity at the 3' end of the asdA gene. The translation efficiency was reduced for both murA and asdA genes by changing their start codon from ATG to GTG. An arabinose-regulated c2 gene is present in the chromosome due to the ΔasdA::TT araC $P_{BAD}$ c2 deletion-insertion. The cloning of a sequence encoding a protective antigen is under $P_{trc}$ control. Transcription terminators (TT) flank all of the domains for controlled lysis, replication and expression so that expression of a function in one domain does not affect the activities of another domain. As a safety feature, the plasmid asdA and murA gene sequences cannot replace the chromosomal asdA and murA mutations. χ8937(pYA3681) exhibits arabinose-dependent growth. Upon invasion of host tissues, an arabinose-free environment (FIG. 11), transcription of asdA, murA and c2 ceases and concentrations of their gene products decrease due to cell division. The drop in C2 concentration results in activation of $P_R$, driving synthesis of anti-sense mRNA to block translation of any residual asdA and murA mRNA. This host-vector grows in LB broth with 0.2% L-arabinose as well as the wild-type strain χ3761, but is unable to grow in or on media devoid of arabinose since it undergoes cell wall-less death by lysis. Vaccine strains with this regulated lysis system are totally avirulent at oral doses in excess of $10^9$ CFU to BALB/c mice and, by release of a bolus of protective antigen upon lysis, induce very good immune responses. These vectors are ideal for delivery of antigens that are difficult to secrete due to structural attributes. In addition, they provide complete biological containment with no persistence in vivo and no survival if excreted.

Example 13

Construction of *S. Typhimurium* Vaccine Strains with Regulated Lysis Phenotype in Order to Release DNA Vaccine Vector after Colonization of Effector Lymphoid Tissues In Vivo and Confer Complete Biological Containment A second host-vector system was devised that harbors a vector pYA3650 (FIG. 12A) with the same regulatory domain that contributes to the lysis phenotype and a eukaryotic expression promoter to use as DNA vaccine vectors for release in situ by regulated delayed cell lysis in vivo and to confer biological containment. Another beneficial feature of this vector is the presence of 15 immune enhancing CpG sequences in pYA3650. The *S. Typhimurium* host strain χ8888 has the ΔasdA::TT araC $P_{BAD}$ c2, $\Delta P_{murA}$:TT araC $P_{BAD}$ murA, Δ(gmd-fcl), ΔendA, ΔaraBAD and ΔaraE mutations. To deliver DNA vaccine vectors, we included a ΔendA mutation which eliminates the periplasmic endonuclease I enzyme, to increase plasmid survival upon its release into the host cell. The ΔaraBAD, which deletes the structural genes for catabolism of arabinose thereby preventing use of arabinose retained in the cell cytoplasm at the time of immunization, and ΔaraE, which deletes gene for arabinose transport and enhances retention of arabinose, mutations would preclude breakdown and leakage of internalized arabinose such that asdA and murA gene transcription on pYA3650 continue for a cell division or two after oral immunization. It should be emphasized, that all of the DNA vaccine host-vector constructions derived from χ8888 with pYA3650 are strictly arabinose-dependent for growth in liquid or on solid media. We have inserted the sequence encoding *E. acervulina* sporozoite antigen (EASZ 240) into DNA vaccine vector pYA3650 to yield pYA3674 (FIG. 12B). The vaccine strain χ8888 (pYA3674) has been characterized in vitro and in vivo for induction of immune responses in chicks and the antibody response against *E. acervulina* sporozoite antigen were very good using this DNA vaccine vector delivery system.

Example 14

Improved DNA Vaccine Vector to Enhance Plasmid Nuclear Import and Resistance to Attack from Eukaryotic Nucleases Although use of non-viral DNA vaccine vectors offers advantages, such as decreasing inflammatory responses, gene expression in vivo remains much lower than observed with their viral counterparts. One reason for such low expression is that bacterial plasmids, unlike many viruses, have not evolved mechanisms to target the nucleus in non-dividing cells and make use of the cell's protein synthesis machinery to produce the antigen of interest. Plasmid nuclear import is dependent on DNA nuclear targeting sequences (DTS) several of which have been identified. The DTS frequently contain transcription factor binding sites, which allow transcription factors to bind to the plasmid in the cytoplasm and escort it to the nucleus by the nuclear localization signal-mediated machinery. The SV40 enhancer, which is known to bind to over 10 distinct transcription factors, is an excellent DTS. The minimum requirement for this function is a single copy of a 72-bp element of the SV40 enhancer, in combination with the CMV immediate-early gene enhancer/promoter (CMV E/P). We have also investigated the other means to enhance import of the DNA vaccine vector into nuclei. The synthesis of eukaryotic transcription factors, e.g., NF-κB and AP-2, is stimulated by *Salmonella* infection. These transcription factors can bind to the non-viral DNA vaccine vectors, allowing the nuclear locating signal to mediate import of plasmid DNA into the nucleus. Nuclease degradation of DNA vaccine vectors after delivery and during trafficking to the nucleus is another barrier that leads to inefficient DNA vaccination. Homopurine-rich tracts in the bovine growth hormone polyadenylation signal (BGH poly A) were identified as labile sequences, and replacement of BGH poly A with SV40 late poly A has improved resistance to attack from eukaryotic nucleases. To increase the efficiency of our DNA vaccine vector system, we inserted the 72 bp DTS (I) of the SV40 enhancer into pYA3650 and replaced the BGH poly A with the SV40 late poly A to yield plasmid pYA4050. These modifications resulted in a substantial increase in the synthesis of EGFP (enhanced green fluororescent protein) from plasmid pYA4050 in multiple cell lines tested. The 72 bp DTS (I) of the SV40 enhancer and an artificial DNA binding sites (DTS (II)) of these eukaryotic transcription factors stated above, were inserted as DNA nuclear targeting sequences into pYA3650 (FIG. 12A). The artificial DNA binding sites can also function as an enhancer since it was inserted upstream of CMV E/P. We also replaced the BGH poly A with the SV40 late poly A in pYA3650 to yield pYA4545 (FIG. 13). DNA vaccine vector pYA4545 allows rapid nuclear import and high-level synthesis of the enhanced green fluorescent proteins (EGFP) in multiple tested cell lines (FIGS. 14A and B). One additional beneficial feature of pYA4545 is that it possesses 24 immune enhancing CpG motifs that should contribute to innate inflammatory responses in different animal hosts.

A dual function vector may be constructed that has the ability to synthesize the protective antigen in the bacterium and upon delivery of the DNA vaccine into the host, can also express the gene when under the eukaryotic promoter. The plasmid vector would hence carry two promoters for antigen expression both in *Salmonella* and in the vaccinated host cells. First, a codon optimized gene under the control of $P_{trc}$ promoter would encode a protective antigen in *Salmonella* and will be released into a vaccinated host upon programmed cell lysis of the bacterial carrier. Then, the (eukaryotic) $P_{CMV}$ promoter will direct synthesis of protective antigen encoded by a codon-optimized gene for efficient expression in the vaccinated host cells. The protective antigen released due to the lysis of *Salmonella* will often induce the neutralizing antibody responses to the pathogen, and the DNA vaccine released simultaneously will express the protective antigen in the vaccinated host.

Example 15

Rationale for Antigen Selection

Recent efforts to clone *Eimeria* spp. genes for use as potential recombinant vaccines were directed toward the goal of developing an alternative strategy for parasite control. A combination of antigen delivery strategies and use of multiple protective antigens could lead to generation of a more diverse immune response and possibly superior protection against challenge. Toward this end, many genes and proteins have been explored as potential vaccine candidates. A number of recombinant proteins have been used, often with mixed results, to vaccinate against avian coccidiosis. The SO7 antigen was described, to be located in the refractile body of *E. tenella* sporozoites. It is highly immunogenic and elicits a strong antibody response in birds during natural infections. Immunisation of 1-day-old chickens with recombinant SO7 induces a high degree of protection against challenge infections not only against *E. tenella*, but also against *Eimeria acervulina*, *Eimeria maxima* and *Eimeria necatrix*. Delivery of the SO7 antigen via attenuated *Salmonella* strains showed that there was induction of significant antibody titers (IgG and IgA) to this antigen in immunized chickens, although no cell-mediated immune responses or *Eimeria* challenge studies were described. We have delivered the SO7 antigen via the T3SS and T2SS of *Salmonella* that induce antigen specific humoral immune responses, and provide partial protection against challenge with *E. acervulina* and *E. tenella*. The SO7 antigen was also used as a candidate for the development of an anti-coccidial DNA-based vaccine. *E. tenella* TA4 is located on the surface of *E. tenella* sporozoites and is a target of the humoral immune response of infected chickens. Two monoclonal antibodies against TA4 inhibit the invasion of sporozoites in cell culture, an indication that TA4 is involved in host cell invasion and a potential target of protective immune responses. The EtMIC2 antigen of *E. tenella* is secreted from the host-parasite interface and is intimately involved in host-cell invasion. More recently, immunization of chickens in ovo with the EtMIC2 gene, or with recombinant protein expressed from the EtMIC2 gene, was shown to reduce oocyst output and prevent weight loss after challenge infection. These studies indicate that vaccines containing microneme proteins can be successfully used to reduce pathology caused by avian coccidiosis. Therefore, we will evaluate the antibody and protective immune responses against *Eimeria* of SO7, TA4 and EtMIC2 antigens delivered by using our newly developed technology.

Example 16

Complete Construction and Characterization of RASV Strains that Confer Biological Containment and are Capable for Antigen Delivery and DNA Vaccine Vector Delivery General Materials and Methods Bacterial strains, media and bacterial growth. RASV strains are derived from *S. Typhimurium* strain UK-1. LB broth and agar are used as complex media for propagation and plating of bacteria. Nutrient broth (Difco), which is devoid of arabinose and mannose, and Neidhardt minimal salts medium and agar will also be used. Bacterial growth is monitored spectrophotometrically and/or by plating.

Molecular and genetic procedures. Methods for DNA isolation, restriction enzyme digestion, DNA cloning and use of PCR for construction and verification of vectors are standard. DNA sequence analysis will be performed in the DNA Sequence Laboratory in the School of Life Sciences. All oligonucleotide and/or gene segment syntheses will be done commercially. Stabilization of mRNA to prolong its half-life will involve site-directed mutagenesis to "destroy" RNase E cleavage sites. Phage P22HTint will be used to transduce mutations of a selectable phenotype from one S. Typhimurium strain into other strains. Conjugational transfer of suicide vectors will be performed by standard methods. Construction of RASV Strain (Strain A) for Antigen Delivery.

We have starting strain S. Typhimurium χ11017 (ΔasdA:: TT araC $P_{BAD}$ c2 ΔmurA::TT araC $P_{BAD}$ murA Δ(gmd-fcl) ΔrelA::araC $P_{BAD}$ lacI TT Δpmi ΔaraBAD). This strain has the ΔasdA::TT araC $P_{BAD}$ c2 and the ΔmurA::TT araC $P_{BAD}$ murA deletion-insertion mutations both having the more tightly regulated araC $P_{BAD}$ activator-promoter to display the regulated lysis phenotype; the Δ(gmd-fcl) mutation and the ΔrelA::araC $P_{BAD}$ lacI TT deletion-insertion mutation to ensure that lysis occurs; the ΔrelA::araC $P_{BAD}$ lacI TT deletion-insertion mutation to confer regulated delayed synthesis of antigen to maximize in vivo antigen synthesis (FIG. 4A); the Δpmi mutation to provide a second means for attenuation to enhance safety and the ΔaraBAD mutation to prevent acid production from arabinose during growth and delay the processes of regulated antigen synthesis and regulated lysis. It should be noted that vaccine constructs are designed to enable synthesis of protective antigens by the Salmonella vaccine prior the onset of lysis. We will introduce the $\Delta P_{NA}::P_{trc\Delta lacO888}$ hilA mutation that results in a hyper-invasive phenotype (FIG. 4B) into χ11017 to yield strain A (ΔasdA::TT araC $P_{BAD}$ c2 ΔmurA::TT araC $P_{BAD}$ murA Δ(gmd-fcl) ΔrelA::araC $P_{BAD}$ lacI TT Δpmi ΔaraBAD $\Delta P_{hilA}::P_{trc\Delta lacO888}$ hilA) for E. tenella SO7 antigen delivery. Construction of RASV Strain (Strain B) for DNA Vaccine Delivery.

As with the antigen delivery system, we will systematically make constructs for DNA vaccine delivery. The S. Typhimurium strain B will have same genotype as strain A except the additional mutations described as following:

(1). Eliminate the periplasmic endonuclease I enzyme. We will include a ΔendA mutation which eliminates the periplasmic endonuclease I enzyme to increase plasmid survival upon its release into the host cell;

(2). Allow Salmonella to escape from the endosome. A ΔsifA mutation that enhances the ability of S. Typhimurium to exit the endosome will augment the desired immune response. However this mutation will lead to hyper-attenuation of the vaccine strain. We will thus include a $\Delta P_{sifA}::TT$ araC $P_{BAD}$ sifA deletion-insertion mutation (FIG. 7) to enable a regulated delayed release of Salmonella from the endosome after the vaccine has colonized multiple lymphoid tissues (Bursa, GALT, liver and spleen) to a high level;

(3). Reduce cytotoxicity. We will include ΔsseL and ΔtlpA mutations that reduce Salmonella-induced pyroptosis/apoptosis to allow Salmonella-infected cells to synthesize antigen directed by DNA vaccines, meanwhile to prevent the suppression of innate immune responses by bacterial infection.

Therefore, the strain B genotype will be: (ΔasdA::TT araC $P_{BAD}$ c2 $\Delta P_{murA25}$::TT araC $P_{BAD}$ murA Δ(gmd-fcl) ΔrelA:: araC $P_{BAD}$ lacI TT Δpmi ΔaraBAD $\Delta P_{hilA}::P_{trc\Delta lacO888}$ hilA ΔendA $\Delta P_{sifA}::TT_{araC}$ $P_{BAD}$ sifA ΔsseL ΔtlpA).

If necessary, we will also test other means to reduce/delay pyroptosis/apoptosis such as determining whether using a strain with total absence of flagella (deletion of fljB and fliC genes to eliminate the synthesis of flagellin) enhances DNA vaccine efficacy.

Strain Characterization.

We include multiple gene modifications in our strains. We take exquisite care in strain construction and do complete biochemical and genetic characterizations after every step in strain construction for stability of plasmid maintenance, integrity and antigen synthesis ability when strains are grown in the presence of arabinose and/or DAP over a 50 generation period. Moreover, we run an LPS gel to make sure we do not select rough variants. Our multiple mutant strains therefore grow at almost the same rate and to the same density as our wild-type parental strains when grown under permissive conditions. With many regulated functions, it is critical that strains commence to synthesize antigens and often deliver them prior to cell lysis to deliver a DNA vaccine. We have been using strains synthesizing βββ-galactosidase and/or GFP to monitor these events and have antibodies against protective antigens that can be used in western blot analyses on the timing of antigen synthesis when strains are deprived of arabinose. So far, antigen synthesis commences several divisions before lysis commences. We can, however, alter −35 and −10 RNA polymerase recognition and binding sites, SD sequences, and start codons to modulate up or down expression of genes for regulatory proteins or those to sustain cell integrity. We also evaluate vaccine strain stability, due to possible recombinational events, and to date have detected no problems. Motility tests and use of specific antisera for given flagellar antigens are used to reveal presence or absence of flagella. Presence of fimbrial adhesins will be assayed using agglutination of yeast and red blood cells in the presence and absence of mannose as a function of growth conditions, Congo red binding assays and by transmission electron microscopy (TEM) using negative staining with phosphotungstic acid. Metabolic attributes of candidate vaccine strains will be evaluated using API-20E tests.

Example 17

Complete Construction and Characterization of Plasmids to Specify the Regulated Delayed Lysis Phenotype and the E. tenella SO7 Antigen, to Specify the Regulated Delayed Lysis Phenotype as DNA Vaccines Encoding SO7, TA4 and EtMIC2 Antigens, Respectively Construction and Characterization of Lysis Vector to Specify Synthesis of the E. Tenella SO7 Antigen in Salmonella Prior to Lysis.

The S. Typhimurium strain A as constructed above is ready to receive a regulated delayed lysis vector specifying synthesis of a protective antigen encoded by genetic information from Eimeria. The cDNA sequence of the E. tenella gene SO7 (EMBL accession number X15898) will be obtained from plasmid pYA4184 bp polymerase chain reaction (PCR). This amplification will yield a PCR fragment spanning the coding region without the nucleic acids coding for the N-terminal signal peptide. The codons of SO7 antigen gene will be optimized so that all codons are those used by *Salmonella* for highly expressed genes. The codon optimized SO7 gene will be inserted into plasmid pYA3681 or into any of the plasmids obtained by modifying the copy number (pYA4589, pYA4594, and pYA4595) (FIGS. 21A, B, and C) or by changing the Shine-Dalgarno sequence (pYA4763) (FIG. 21D) so that SO7 antigen synthesis is controlled by the $P_{trc}$ promoter that is repressed by the LacI repressor synthesized by bacterial strains with the chromosomal ΔrelA::araC $P_{BAD}$ lacI TT insertion when grown with arabinose (FIG. 15A). Plasmid constructs will be verified by DNA sequencing. The ability to specify synthesis of proteins will be evaluated using gel electrophoresis and western blot analyses dependent on growth with or without arabinose (or by addition of IPTG).

Construction and Characterization of Lysis Vector to Function as DNA Vaccines Encoding *E. tenella* SO7, TA4 or EtMIC2 Antigen.

The cDNA sequence of the *E. tenella* gene SO7 (EMBL accession number X15898) will be obtained from plasmid pYA4184 bp PCR. The cDNA sequence of the *E. tenella* genes TA4 (EMBL accession number M21004) and EtMIC2 (GenBank accession number AF111839) will be obtained by PCR of reverse transcribed *E. tenella*-RNA. These amplifications yielded PCR fragments with Kozak translation initiation sequence and spanning the coding region of *E. tenella* genes SO7, TA4 and EtMIC2, respectively, without the nucleic acids coding for the N-terminal signal peptide. These fragments encoding SO7, TA4 and EtMIC2 antigen will be inserted into the improved DNA vaccine vector pYA4545 (FIG. 13), respectively. All DNA vaccine constructs (FIG. 15B, C and D) will be sequenced and copy numbers determined. The expression of each antigen in pYA4545 will be tested using EGFP fusions in cell lines. We will introduce pYA4545 constructs into the *S. Typhimurium* host strain B to evaluate our regulated delayed lysis system for DNA vaccine delivery against *Eimeria*.

Characterization of Experimental Vaccine Strains.

RASV strains will be fully characterized before immunization studies. All RASV strains will be evaluated for plasmid stability when strains are grown in the presence of arabinose and/or DAP over a 50 generation period and the number of cell doublings to commence recombinant antigen synthesis and assembly before onset of lysis when deprived of arabinose. We will monitor timing to commence lysis and verify that it is complete to yield no survivors. With many regulated functions, it is critical that strains commence to synthesize antigens prior to cell lysis. We will use strains synthesizing b-galactosidase or GFP to monitor release of antigen through lysis and will have specific serum for inserts that are used in western blot analyses to monitor the timing of antigen synthesis when strains are deprived of arabinose. The cell lysis, the hyper-invasive phenotype, the ability of *Salmonella* endosome escape and the reduced cytotoxicity of RASV strains will be tested using multiple cell lines. The ability of vaccine strains to attach to, invade into and survive in various macrophage and epithelial cell lines will be quantitated by well established methods that we have used routinely including use of primary chicken fibroblast cell lines. Nomarski interference and phase contrast microscopy are also used to make sure that vaccine strains with multiple genetic changes look healthy, an attribute necessary for invading cells in culture and colonizing lymphoid tissues in the immunized chicken.

Expected Outcomes.

RASV strain A harboring pYA3681 constructs will be hyper-invasive, exhibit regulated delayed attenuation, regulated delayed antigen synthesis and regulated delayed lysis to release antigen and to confer biological containment. In addition of these characters, RASV strain B harboring pYA4545 constructs will also exhibit reduced *Salmonella*-induced pyroptosis/apoptosis and have the ability to escape from the endosome of host cells to efficiently deliver improved DNA vaccine vectors.

Possible Alternatives.

The timing of *Salmonella* cell lysis to release synthesized antigen is critical for inducing desired immune responses. We have now constructed the regulated lysis vector pYA3681 derivatives, pYA4595, pYA4589 and pYA4594 with pSC101 ori, p15A ori and pUC ori, such that we can better vary the timing of lysis in vivo for release of a bolus of antigen. We will determine the levels and duration of vaccine strain persistence and the efficiency of SO7 antigen delivery. For DNA vaccine delivery, if the high copy number pYA4545 constructs are unstable in *Salmonella* strain B during infection, lower copy number plasmids of pYA4545 derivatives pYA5123 (pBR ori), pYA5124 (p15A ori), and pYA5125 (pSC101 ori) (FIGS. 22A, B, and C) have been constructed to overcome the problem; the precursor TA4 antigen synthesized after initiation of oocyst sporulation will be processed into a mature form. The TA4 antigen is composed of a 17 kDa (amino acid 24-181) subunit and an 8 kDa (amino acid 185-253) subunit, linked by a disulfide bond. If the full length of precursor synthesized by specified DNA vaccine vector sequences does not induce good immune response because of lacking post-translation modification, we will investigate whether insertion of the sequences encoding the TA4 antigen 17 kDa subunit and 8 kDa subunit with an internal ribosome entry site (IRES) in between will give better results. If any of the constructs induce immune responses, especially cellular immune responses, that are superior to the original host-vector constructs, we will conduct immunization-challenge studies.

Example 18

Evaluate the Abilities of the Different RASV Strains to Colonize Lymphoid Tissues in Chickens and Exhibit Biological Containment Attributes, to Induce Mucosal, Systemic and Cellular Immune Responses to *Eimeria* Antigens, and to Induce Protective Immunity to *Eimeria* Oocytes Challenge Evaluate the Abilities of RASV Strains to Colonize Lymphoid Tissues in Chickens and Exhibit Biological Containment Attributes.

After full in vitro characterization of the bacterial host strains and recombinant vectors, we will examine the ability of each recombinant host-vector combination to colonize intestinal epithelial cells, the bursa, and spleen. White leghorn chicks will be hatched in our animal facility from fertile eggs obtained from SPAFAS (Voluntown, Conn.). All birds will be housed in Horsefall units under ABSL-2 containment for vaccination. For infection of chicks, bacterial strains will be grown as standing overnight cultures and then diluted into pre-warmed LB with 0.1% arabinose and 0.5% mannose broth and grown with mild aeration on a rotary shaker, generally to an $OD_{600}$ of about 0.8. Cells will be sedimented by centrifugation and suspended in buffered saline with gelatin (BSG). Day-of hatch chicks will be orally immunized with $10^9$ CFU dose using a micropipette and food and water provided 30 min after immunization. A booster immunization will be given seven days later (in chicks deprived of food and water for 6 hours prior to immunization). We will determine the CFU recoverable per gram of tissue for each tissue and time, and will add mannose, arabinose and DAP to the recovery media to facilitate recovery of damaged cells. We do this for three chicks per vaccine strain at 3, 7, 11 and 18 days after immunization. These studies will also reveal the time for commencement of cell lysis of RASVs. Evaluate the Abilities of RASV Strains to Induce Mucosal, Systemic and Cellular Immunities to *Eimeria* Antigens.

The RASV strain A harboring pYA3681 specifying SO7 and the RASV strain B harboring pYA4545 encoding SO7, TA4 or EtMIC2, that are deemed to have satisfactory performance criteria as described above, will be analyzed for capacity to elicit appropriate immune responses to the respective *Eimeria* antigens. The growth of strains and the primary immunization will be as described above, and then boosted with the same dose at 1 week.

Antigen Preparation

We have or make purified His-tagged proteins from recombinant *E. coli* $\chi$7385 for all antigens specified by RASVs. $\chi$7385 has been engineered to avoid potential contamination of proteins by elimination of all appendage proteins and LPS O-antigen. *Salmonella* LPS O-antigen will be obtained commercially but we are now purifying LPS core and O-antigen components to also use in ELISAs. We have prepared an *S. Typhimurium* outer membrane protein (SOMP) fraction from $\chi$9424 that has been engineered to be unable to produce flagella, all in vitro-expressed pilus antigens, and LPS O-antigen and a heat killed extract of the wild-type *S. Typhimurium* UK-1 strain $\chi$3761. These antigens will be used as controls in western blots as well as for immunoassays as described below.

ELISA

Sera taken by wing vein bleeding at 3, 4 and 5 weeks after the boost will be tested by ELISA for SO7, TA4 or EtMIC2, as well as LPS and OMP specific IgG. In initial studies, sera will be pooled from all chicks in a group but in later studies with successful constructs, antibody titers will be monitored in individuals. We will employ a doubling dilution method with the end point titer being the dilution giving an $OD_{410}$ three times that for the reagent or unimmunized animal control. These methods have been described in previous manuscripts.

Delayed-Type Hypersensitivity (DTP) Reactions

DTH reactions will be determined in order to detect relevant cell-mediated immune responses. Purified *E. tenella* His-tagged antigens or *Salmonella* outer membrane proteins will be appropriately diluted in PBS and injected into the left wattle of the chicken. The right wattle will be injected with a similar amount of PBS and will serve as a control. Wattle swelling in response to injections, indicating a DTH response, will be determined by measuring the wattle thickness with a dial-metric caliper at 24, 48, and 72 hours post-injection. We have previously used a toe web assay for DTH in chickens as well.

Preparation of Lymphocytes

Three chickens from each group of non-immunized and immunized birds will be humanely euthanized at 7 and 28 days after the boost immunization to collected splenocytes. Splenic lymphocytes will be separated with a Ficoll-Hypaque density gradient. We will separate the lymphocytes into different populations by passing the cells through nylon wool columns. Unbound T cells and macrophages will be resuspended in RPMI 1640 with 10% chicken serum and incubated in tissue culture flasks for 3 h. After 3 h, the nonadherent T cells will be collected.

CTL Assays

CTL activity will be measured by the CytoTox96 nonradioactive cytotoxicity assay (Promega), which detects the stable cytosolic enzyme lactate dehydrogenase (LDH) when it is released from lysed cells. The assay will be performed as instructed by the manufacturer. Briefly, the primary chicken kidney cells, which served as the target cells, will be transfected with a Sindbis virus vector, expressing suitable antigen. Various amounts of effector T cells will be used immediately in the CTL assay. The remaining cells will be re-stimulated with the appropriate antigen for five to seven days prior to use in the CTL assay. Specific lysis of target cells by CTLs will be calculated according to the following formula: (LDH in the mixture of target and effector cells–LDH spontaneously released from target cells and effector cells/total LDH of target cells–LDH spontaneously released from target cells)×100. All assays will be performed in a quadruplicate set of wells.

Statistical Analysis:

All results will be analyzed using Duncans multi-range test from the SAS program to compare vaccine and control groups for statistical differences.

The constructs that show superior immune responses, especially cellular immune responses, will be used to conduct immunization-challenge studies.

Immunization and Challenge Studies (1). Titration of *Eimeria* oocysts. *E. acervulina* (Strain APU #12) and *E. tenella* (Strain WR-1) oocysts, that have been passaged in the lab for over 3 years and still retain fecundity and pathogenicity, will be propagated by fecal harvest from chickens infected with the respective strains. The oocysts will be purified by sucrose gradient centrifugation and suspended in sterilized water using standard procedures. Before an actual experimental challenge, the small-scale experiments will be performed on the batch of oocysts to be used. In general, groups of chickens will be inoculated with $3\times10^5$, $4\times10^5$ and $5\times10^5$ oocysts and then weight gain measured and intestinal lesions scored six days later. Data will be compared to those obtained from the non-infected controls. The purpose of this titration experiment is to ensure that the challenge dose will be high enough to depress weight gain by about 20% (typical weight loss observed under field conditions) and yet not too high to overwhelm immunity. The chickens in the experimental vaccine trial will then be challenged with an adequate dose in 1 ml water as determined by the titration trial using the same batch of oocysts.

Evaluate the Abilities of RASV Strains to Induce Protective Immunity to *Eimeria* Oocyst Challenge.

Three *Eimeria* oocyst challenge studies will be performed at the USDA/ARS Laboratories, Beltsville (Table 1). The chickens (Sexsal breed) will be purchased from the Hyline Hatchery in Pennsylvania. The advantage of this breed is that chicks can be sexed at hatch. For these experiments 1-day-old male chickens will be assigned randomly to appropriate groups with 21 chickens per group in Petersime starter chick cages and inoculated orally with $10^9$ CFU of RASV strains in 50 ml BSG. The second dose of RASV strains will be administered 1 week later. To measure protection against *Eimeria* oocyst challenge, body weight gain, feed conversion efficiency, and intestinal lesion will be recorded 1 week after *Eimeria* challenge (peak clinical signs). Serum from individual chickens will be tested by ELISA for antibodies to recombinant *Eimeria*, native *Eimeria*, and *Salmonella* surface antigens before and after challenge using standard procedures for recombinant and native proteins. A number of studies have found cross-reactivity of *Eimeria* antigens SO7, EtMIC2, and TA4 between different *Eimeria* species. Induction of cross-immunity by a single *Eimeria* antigen is highly desirable because it reduces the number of antigens required in a vaccine. Similar to live oocyst vaccines, which are a mixture of at least 3 *Eimeria* species, any recombinant vaccine would need to be cross-protective against *E. acervulina, E. maxima*, and *E. tenella* (the three major field species). Therefore, we will test RASV delivery of the *E. tenella* SO7 antigen to induce cross-protective immunity to *E. acervulina* oocyst challenge.

TABLE 1

Summary of vaccine strains and immunization-challenge plan

| Trials | | Vaccine strains and doses (CFU) of immunization at day 1 | Vaccine strains and doses of boost at day 7 | *Eimeria* species and oocyst doses of challenge at 4 weeks |
|---|---|---|---|---|
| Trial 1 | G*1 | BSG, 50 µl | BSG, 50 µl | H$_2$O, 1 ml |
| | G 2 | strain A (pYA3681**), 10$^9$ | strain B (pYA4545), 10$^9$ | *E. tenella*, 10$^5$ |
| | G 3 | strain A (pYA3681-SO7), 10$^9$ | strain A (pYA3681-SO7), 10$^9$ | *E. tenella*, 10$^5$ |
| | G 4 | strain B (pYA4545-SO7), 10$^9$ | strain B (pYA4545-SO7), 10$^9$ | *E. tenella*, 10$^5$ |
| | G 5 | strain A (pYA3681-SO7), 10$^9$ | strain B (pYA4545-SO7), 10$^9$ | *E. tenella*, 10$^5$ |
| | G 6 | strain B (pYA4545-SO7), 10$^9$ | strain A (pYA3681-SO7), 10$^9$ | *E. tenella*, 10$^5$ |
| Trial 2: groups, immunization and boost will be same with Trial 1 | | | | *E. acervulina*, 10$^5$ |
| Trial 3 | G 1 | BSG, 50 µl | BSG, 50 µl | H$_2$O, 1 ml |
| | G 2 | strain A (pYA3681**), 10$^9$ | strain B (pYA4545), 10$^9$ | *E. tenella*, 10$^5$ |
| | G 3 | strain A (pYA3681-SO7), 10$^9$ | strain B (pYA4545-TA4), 10$^9$ | *E. tenella*, 10$^5$ |
| | G 4 | strain A (pYA3681-SO7), 10$^9$ | strain B (pYA4545-EtMIC2), 10$^9$ | *E. tenella*, 10$^5$ |
| | G 5 | strain B (pYA4545-SO7), 10$^9$ | strain B (pYA4545-TA4), 10$^9$ | *E. tenella*, 10$^5$ |
| | G 6 | strain B (pYA4545-SO7), 10$^9$ | strain B (pYA4545-EtMIC2), 10$^9$ | *E. tenella*, 10$^5$ |

*Group,
**pYA3681 (or derivative)

Trial 1: Evaluating the ability of the RASV strain A harboring pYA3681 (or derivative) expressing *E. tenella* SO7 antigen and the RASV strain B harboring pYA4545 encoding *E. tenella* SO7 antigen to induce protective immunity to *E. tenella* oocyst challenge. The experimental groups and immunization-challenge experiment will be performed as indicated in Table 1. Three weeks after boost (when the animals are 4 weeks old), the chickens in groups G2 to G6 will be orally challenged with 10$^5$ *E. tenella* oocysts.

Trial 2: Evaluating the ability of the RASV strain A harboring pYA3681 (or derivative) and the RASV strain B harboring pYA4545 encoding *E. tenella* SO7 antigen to induce cross-protective immunity to *E. acervulina* oocyst challenge. The immunization groups, primary immunization and boost protocol will be same with Trial 1 (Table 1). Three weeks after boost (when the animals are 4 weeks old), the chickens in groups G2 to G6 will be orally challenged with 10$^5$ *E. acervulina* oocysts.

Trial 3: Evaluating the ability of the RASV strain A harboring pYA3681 (or derivative) and the RASV strain B harboring pYA4545 specifying *E. tenella* SO7 antigen in combination with other *E. tenella* antigens (TA4, EtMIC2) to induce protective immunity to *E. tenella* oocyst challenge. The experimental groups and immunization-challenge experiment will be performed as indicated in Table 1. Three weeks after boost (when the animals are 4 weeks old), the chickens in groups G2 to G6 will be orally challenged with 10$^5$ *E. tenella* oocysts.

Statistical Analysis.

All results will be analyzed using Duncans multi-range test from the SAS program to compare vaccine and control groups for statistical differences. A power analysis was conducted using typical data from a recent study in which mean and standard error of weight gain in the non-*Eimeria* challenge control group (mean of 3 sub-groups containing 7 chickens/subgroup) was equal to 450+30 grams, and mean and standard error of *Eimeria* challenge control group was equal to 360+30 grams. Please note that standard error varied between 10-30 grams, but 30 grams was used in the power analysis as the worst case scenario. The hypothesis being tested was as follows—Is there sufficient power (>80%) to show a significant difference (P<0.05) between vaccinated-*Eimeria* challenged and non-vaccinated, *Eimeria* challenged controls using the proposed experimental design (6 groups, 3 sub-groups per treatment, 7 chickens per subgroup) assuming that a 90 gram weight loss difference is relevant. The power analysis showed that ANOVA (Duncan's mult-range test) will detect a significant difference between the challenged control and all other treatment groups (a difference of 90 grams) with 85% power. Thus, the experimental design consisting of 6 groups, 3 sub-groups per treatment, 7 chickens per subgroup has sufficient power to distinguish a significant difference between non-vaccinated and vaccinated *Eimeria*-challenged groups.

Expected Outcomes

These studies will provide essential information on the abilities of RASV strains to deliver *Eimeria* protective antigen and DNA vaccines encoding *Eimeria* antigens to induce mucosal, systemic, cellular immunities to *Eimeria* antigens and protective immunity to *Eimeria* oocyst challenge, leading to finalize the vaccine strains that are able to prevent *Eimeria* infection of poultry.

Example 19

Construct and Characterize *Salmonella* pYA4545 DNA Vaccine Vector Derivatives Encoding Influenza HA (and NA)

We have constructed the RASV lysis strains χ9354 (ΔasdA::TT araC P$_{BAD}$ c2 ΔP$_{murA}$::TT araC P$_{BAD}$ murA ΔaraBAD ΔaraE ΔrelA Δ(gmd-fcl) ΔendA ΔsifA), χ11212 (χ9354 with ΔtlpA mutation), χ11213 (χ9354 with ΔsseL mutation), χ11214 (χ9354 with ΔP$_{hilA}$::P$_{trc \, \Delta lacO}$ hilA mutation), χ11215 (χ9354 with ΔtlpA and ΔsseL mutations), χ11216 (χ9354 with ΔtlpA and ΔP$_{hilA}$::P$_{trc \, \Delta lacO}$ hilA mutations), χ11217 (χ9354 with ΔsseL and ΔP$_{hilA}$::P$_{trc \, \Delta lacO}$ hilA mutations) and χ11218 (χ9354 with ΔtlpA, ΔsseL and ΔP$_{hilA}$::P$_{trc \, \Delta lacO}$ hilA mutations).

An improved DNA vaccine vector pYA4859 (pYA4545 expressing HA of influenza A/WSN/33 virus) delivering by χ11213, χ11214, χ11215, χ11216, χ11217 and χ11218 that induced high serum IgG responses to WSN HA in mice after oral immunization in comparison with those IgG responses induced by χ9354(pYA4859) (FIG. 16) and protected immunized mice from challenge with 100 LD$_{50}$ of rWSN virus (FIG. 17, FIG. 18 and FIG. 19).

We will construct a DNA vaccine co-expressing both HA and NA to compare its immunogenicity and protective efficacy with that expressing HA alone. To achieve high-level expression of HA, a codon-optimized cDNA sequence of the influenza A/WSN/33 HA gene was synthesized for maximized expression in mammalian cells, with Kozak translation initiation sequence and inserted into pYA4545 to yield DNA vaccine pYA4545 HA.

To construct a DNA vaccine co-expressing HA and NA, a synthesized codon-optimized cDNA sequence (with Kozak sequence) of mouse-adapted influenza strain B/Ann Arbor/4/55 NA genes preceded by an internal ribosome entry site (IRES) of the encephalomyocarditis virus will be inserted into pYA4545 HA. This will yield DNA vaccine vector pYA4545 HA-IRES-NA. We will introduce pYA4545 HA and pYA4545 HA-IRES-NA into RASV lysis strains with $\Delta sifA26$, $\Delta P_{hilA}::P_{trc\Delta lacO888}$ hilA, $\Delta tlpA181$ or/and $\Delta sseL116$ mutations, respectively, to evaluate the efficacy of DNA vaccine delivery in mice.

We will evaluate the effect on immune response and protection in mice from the lethal effect of influenza A/WSN/33 (for RASV lysis strain specifying pYA4545 HA) or influenza A/WSN/33 and B/Ann Arbor/4/55 (for RASV lysis strain harboring pYA4545 HA-IRES-NA). Fusion of the sequence encoding SopE2 to the C-terminal end of the HA (or NA) encoding sequence represents another possible improvement since the SopE2 protein is rapidly ubiquinated to facilitate protein trafficking to the proteosome for efficient class I presentation. We will test this prediction.

Example 20

Design and Construct an Optimized DNA Vaccine Encoding the HIV-1 Env and Gag Proteins with and without Added CpG Motifs for Interaction with TLR9 in the DNA Vaccine The expression of both the HIV-1 env and gag genes depends on the presence of the vital Rev protein. This dependence is, at least in part, due to the presence of negatively acting Rev-responsive element (RRE) sequences located within unspliced and partially spliced mRNAs. Rev shuttles between the nucleus and the cytoplasm and promotes the export of the subset of RRE-containing mRNAs. Rev-RRE interaction also results in increased stabilities of these mRNAs and their efficient polysomal loading. To achieve high-level Rev-independent expression of the env and gag genes in DNA vaccine vector pYA4545, the codon usage pattern will be first altered to conform to that used by highly expressed human genes. Further modifications will then be made to mutate the Tyr residue of the conserved tyrosine-based endocytosis motif in the cytoplasmic domain of Env to enhance surface display. In addition, the less efficient endogenous HIV leader sequence will be replaced by an optimal consensus sequence for the initiation of translation (GCCACCAUGG).

On the other hand, we will remove a possible residual RRE sequence previously identified in the gag-coding region to allow high-level Rev-independent gag expression. The sequence-modified env and gag genes will be inserted into pYA4545 as two independent genes regulated by the PCMV promoter and an internal ribosome entry site (IRES) of the encephalomyocarditis virus, respectively.

The pYA4545 vector encoding the optimized HIV-1 Clade B env and gag sequences is diagrammed in FIG. 20. The pYA4545 vector possesses 24 CpG sequences interacting with TLR9 in various animal species but no GACGTT sequence that is optimal for immune enhancement by interaction with TLR9 in mice. Although it is doubtful that addition of ODNs with optimal CpG sequences for mice will further augment immunity, we will test this possibility.

What is claimed is:

1. A recombinant *Salmonella* bacterium, wherein the bacterium comprises:
   (a) a mutation selected from the group consisting of a $\Delta P_{hilA}::P_{trc\Delta lacO}$ hilA mutation and a $\Delta P_{hilA}::P_{hilA}$ hilA mutation, wherein the $\Delta P_{hilA}::P_{hilA}$ hilA mutation comprises a mutation in the hilA promoter that reduces nucleoid-associated protein H-NS binding,
   (b) a $\Delta tlpA$ mutation and a $\Delta sseL$ mutation and, optionally at least one mutation selected from the group consisting of an ampG mutation, an ampD mutation, and a nagE mutation, and
   (c) at least one mutation selected from the group consisting of a tlyC mutation, a pld mutation, a $\Delta sifA$ mutation and a $\Delta P_{sifA}::TT$ araC $P_{BAD}$ sifA mutation.

2. The recombinant *Salmonella* bacterium of claim 1, wherein the bacterium lacks expression of sifA.

3. A recombinant *Salmonella* bacterium, wherein the bacterium is:
   (a) capable of regulated delayed attenuation,
   (b) capable of regulated delayed lysis, characterized by a $\Delta P_{murA}::TT$ araC $P_{BAD}$ murA mutation and a $\Delta asdA::TT$ araC $P_{BAD}$ c2 mutation,
   (c) capable of escape from a host endosomal compartment, characterized by at least one mutation selected from the group consisting of a tlyC mutation and a pld mutation, (d) capable of hyper-invasion, characterized by hilA operably linked to a constitutive promoter, and (e) capable of reducing bacterium-induced host programmed cell death, characterized by a ΔtlpA mutation and a ΔsseL mutation and, optionally, at least one mutation selected from the group consisting of an ampG mutation, an ampD mutation, and a nagE mutation.

4. The recombinant *Salmonella* bacterium of claim 3, wherein the programmed cell death is pyroptosis or apoptosis.

5. The recombinant *Salmonella* bacterium of claim 3, wherein the bacterium further comprises a DNA vaccine encoding a protective antigen.

6. The recombinant *Salmonella* bacterium of claim 5, wherein the DNA vaccine comprises a nucleic acid sequence encoding one or more bacterial, viral, protozoan, or fungal antigens.

7. The recombinant *Salmonella* bacterium of claim 5, wherein the DNA vaccine comprises a nucleic acid sequence encoding one or more influenza antigens.

8. The recombinant *Salmonella* bacterium of claim 3, wherein the bacterium further comprises a single vector for the production of influenza virus.

9. The recombinant *Salmonella* bacterium of claim 3, wherein the bacterium escapes from the host endosomal compartment before undergoing regulated lysis.

10. The recombinant *Salmonella* bacterium of claim 5, wherein the DNA vaccine comprises a repeated DNA nuclear targeting sequence and a nuclease resistant polyadenylation encoding sequence.

11. The recombinant *Salmonella* bacterium of claim 10, wherein the DNA vaccine comprises an artificial NF-kB recognition sequence and or an artificial AP-2 recognition sequence.

12. The recombinant *Salmonella* bacterium of claim 5, wherein the DNA vaccine comprises the vector pYA4545.

13. The recombinant *Salmonella* bacterium of claim 5, wherein the DNA vaccine comprises an influenza HA antigen-SopE C-terminal fusion.

14. The recombinant *Salmonella* bacterium of claim 3, wherein the bacterium further comprises the vector pYA3681.

15. The recombinant *Salmonella* bacterium of claim 1, wherein the bacterium comprises a ΔampG mutation, a ΔampD mutation, or a ΔnagE mutation.

16. The recombinant *Salmonella* bacterium of claim 10, wherein the nuclease resistant polyadenylation sequence is derived from a DNA virus capable of replicating in a eukaryote.

17. A recombinant *Salmonella* bacterium, wherein the bacterium is:

(a) capable of regulated delayed attenuation, (b) capable of regulated delayed lysis, characterized by $\Delta P_{murA}$::TT araC $P_{BAD}$ murA mutation and a ΔasdA:: TT araC $P_{BAD}$ c2 mutation, (c) capable of escape from a host endosomal compartment, characterized by at least one mutation selected from the group consisting of a tlyC mutation, a pld mutation, a ΔsifA mutation and $\Delta P_{sifA}$::TT araC $P_{BAD}$ sifA mutation, (d) capable of hyper-invasion, characterized by hilA operably linked to a constitutive promoter, and (e) capable of reducing bacterium-induced host programmed cell death, characterized by a ΔtlpA mutation and a ΔsseL mutation and, optionally, a mutation selected from the group consisting of an ampG mutation, an ampD mutation, and a nagE mutation.

18. The recombinant *Salmonella* bacterium of claim 3, wherein the hilA operably linked to a constitutive promoter is selected from the group consisting of $\Delta P_{hilA}$::$P_{trc\Delta lacO}$ hilA and $\Delta P_{hilA}$::$P_{hilA}$ hilA mutation, wherein the $\Delta P_{hilA}$::$P_{hilA}$ hilA mutation comprises a mutation in the hilA promoter that reduces nucleoid-associated protein H-NS binding.

19. The recombinant *Salmonella* bacterium of claim 17, wherein the hilA operably linked to a constitutive promoter is selected from the group consisting of a $\Delta P_{hilA}$::$P_{trc\Delta lacO}$ hilA mutation and a $\Delta P_{hilA}$::$P_{hilA}$ hilA mutation, wherein the $\Delta P_{hilA}$::$P_{hilA}$ hilA mutation comprises a mutation in the hilA promoter that reduces nucleoid-associated protein H-NS binding.

20. A recombinant *Salmonella* bacterium, wherein the bacterium is:

(a) capable of regulated delayed attenuation, (b) capable of regulated delayed lysis, characterized by a $\Delta P_{murA}$::TT araC $P_{BAD}$ murA mutation and a ΔasdA:: TT araC $P_{BAD}$ c2 mutation, (c) capable of escape from a host endosomal compartment, characterized by at least one mutation selected from the group consisting of a tlyC mutation, a pld mutation, a ΔsifA mutation and $\Delta P_{sifA}$::TT araC $P_{BAD}$ sifA mutation, and (d) capable of reducing bacterium-induced host programmed cell death, characterized by a ΔtlpA mutation and a ΔsseL mutation and, optionally, a mutation selected from the group consisting of an ampG mutation, an ampG mutation, and a nagE mutation.

21. A vaccine, the vaccine comprising the recombinant *Salmonella* bacterium of claim 20.

SEQUENCE LISTING

<160> NUMBER OF SEQ ID NOS: 1

<210> SEQ ID NO 1
<211> LENGTH: 74
<212> TYPE: DNA
<213> ORGANISM: Artificial Sequence
<220> FEATURE:
<223> OTHER INFORMATION: salmonella

<400> SEQUENCE: 1
ggggactttc cggggacttt cctccccacg cgggggactt tccgccacgg gcggggactt       60
tccggggact ttcc       74